US010485824B2

(12) United States Patent
Hedrick et al.

(10) Patent No.: US 10,485,824 B2
(45) Date of Patent: *Nov. 26, 2019

(54) CATIONIC POLYAMINES FOR TREATMENT OF VIRUSES

(71) Applicants:International Business Machines Corporation, Armonk, NY (US); AGENCY FOR SCIENCE, TECHNOLOGY AND RESEARCH, Singapore (SG); NATIONAL UNIVERSITY OF SINGAPORE, Singapore (SG)

(72) Inventors: James L. Hedrick, Pleasanton, CA (US); Ichiyama Koji, Singapore (SG); Naoki Yamamoto, Singapore (SG); Chuan Yang, Singapore (SG); Yi Yan Yang, Singapore (SG)

(73) Assignees: International Business Machines Corporation, Armonk, NY (US); Agency For Science, Technology And Research, Singapore (SG); National University of Singapore, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/610,692

(22) Filed: Jun. 1, 2017

(65) Prior Publication Data

US 2017/0266224 A1   Sep. 21, 2017

Related U.S. Application Data

(63) Continuation of application No. 14/605,228, filed on Jan. 26, 2015, now Pat. No. 9,682,100.

(51) Int. Cl.
*A61K 31/785* (2006.01)
*C08G 73/02* (2006.01)
*C12N 7/00* (2006.01)

(52) U.S. Cl.
CPC ........ *A61K 31/785* (2013.01); *C08G 73/0206* (2013.01); *C08G 73/0233* (2013.01); *C12N 7/00* (2013.01); *C12N 2710/10363* (2013.01); *C12N 2710/16663* (2013.01); *C12N 2760/16163* (2013.01); *C12N 2770/20063* (2013.01); *C12N 2770/24163* (2013.01); *C12N 2770/32363* (2013.01); *C12N 2770/36163* (2013.01); *Y02A 50/382* (2018.01); *Y02A 50/385* (2018.01)

(58) Field of Classification Search
CPC .............. A61K 31/785; C08G 73/0206; C08G 73/0233; C12N 7/00; C12N 2710/10363; C12N 2710/16663; C12N 2760/16163; C12N 2770/20063; C12N 2770/24163; C12N 2770/32363; C12N 2770/36163; Y02A 50/385

See application file for complete search history.

(56) References Cited

U.S. PATENT DOCUMENTS

| 8,318,856 B2 | 11/2012 | Oh et al. |
| 8,703,197 B2 | 4/2014 | Cheng et al. |
| 9,399,044 B2 | 7/2016 | Cheng et al. |
| 2004/0087024 A1 | 5/2004 | Bellocq et al. |
| 2004/0142474 A1 | 7/2004 | Mahato et al. |
| 2005/0031579 A1 | 2/2005 | Schluep |
| 2010/0291032 A1 | 11/2010 | Guenther |
| 2012/0021043 A1 | 1/2012 | Krampa et al. |
| 2014/0073048 A1 | 3/2014 | Cheng et al. |
| 2014/0080215 A1 | 3/2014 | Cheng et al. |
| 2014/0142166 A1 | 5/2014 | Ventura et al. |
| 2014/0256545 A1 | 9/2014 | Velev et al. |
| 2015/0342984 A1 | 12/2015 | Cheng et al. |

OTHER PUBLICATIONS

Aung et al., "Polyethylenimines (PEI) polymer functionalized with L-mannose moieties inhibits hepatitis B virus (HBV) entry into HepG2-hNTCP cells with negligible cellular toxicity", Abstract and Poster, International Hepatitis B Viruses Meeting: 2016, Soul, Korea, Sep. 21-24, 2016.
Carmon-Ribeiro, et al., "Cationic Antimicrobial Polymers and Their Assemblies", Int. J. Mol. Sci. 2013, 14, 9906-9946.
Farias, et al., "Effect of ammionium chloride on the multiplication of infectious pancreatic necrosis virus", Arch Virol (1988), 98, 155-162.
Lee, "Polyethylenimines (PEI) polymer functionalized with L-mannose moieties inhibits hepatitis B virus (HBV) entry into HepG2-hNTCP cells with negligible cellular toxicity", AASLD LiverLearning, abstract for presentation given Nov. 14, 2016.
Low, et al., "Early Dengue Infection and Outcome Study (EDEN)—Study Design and Preliminary Findings", Ann Acad Med Singapore 2006, 35, 783-789.

(Continued)

*Primary Examiner* — David J Blanchard
*Assistant Examiner* — Thurman Wheeler
(74) *Attorney, Agent, or Firm* — Michael R. Roberts

(57) ABSTRACT

Antiviral cationic polyamines were prepared by modifying polyethylenimines with N-acylating agents that introduce a side chain comprising one or more carbons and at least one alcohol hydroxy group. The cationic polyamines can have a linear or branched polyethylenimine backbone structure. Preferably, the cationic polyamines comprise pendant monosaccharide groups, which can be introduced via a cyclic carbonate comprising a pendant protected monosaccharide (e.g., mannose) group. The cationic polyamines can be active and selective against a broad spectrum of viruses at low concentrations, and are generally non-toxic.

22 Claims, 29 Drawing Sheets

(56) References Cited

OTHER PUBLICATIONS

Miller, et al., "The Mannose Receptor Mediates Dengue Virus Infection of Macrophages", PLoS Pathogens, 2008, vol. 4, e17, pp. 1-11
Pratt, et al., "Tagging alcohols with cyclic carbonate: a versatile equivalent of (meth)acrylate for ring-opening polymerizationt", Chem. Commun., 2008, 114-116.
Seow, et al., "Oxidation as a Facile Strategy to Reduce the Surface Charge and Toxicity of Polyethyleneimine Gene Carriers", Biomacromoleculees, 2013, 14, 2340-2346.
Spoden, et al., "Polyethylenimine is a Strong Inhibitor of Human Papillomavirus and Cytomegalovirus Infection", Antimicrobial Agents and Chemotherapy Antimicrob. Agents Chemother. 2012, 56, p. 75-82.
Tahara-Hanaoka et al., "Lentiviral vector—mediated transduction of murine CD34 hematopoietic stem cells", Experimental Hematology 30 (2002) 11-17.
USPTO, final office action dated Aug. 29, 2016, U.S. Appl. No. 14/605,228.
USPTO, non-final office action dated Mar. 28, 2016, U.S. Appl. No. 14/288,782.
USPTO, non-final office action dated Nov. 10, 2015, U.S. Appl. No. 14/605,228.
Anthony et al., "A Strategy to Estimate Unknown Viral Diversity in Mammals," mBio 4(5): e00598-13. doi:10.1128/mBio.00598-13; Published Sep. 3, 2013.
Barr et al., "Bacteriophage adhering to mucus provide a non-host-derived immunity," PNAS Jun. 25, 2013 110 (26) 10771-10776.
Bartlett et al., "Oncolytic viruses as therapeutic cancer vaccines," Molecular Cancer, 2013, 12, p. 103, Abstract.
IUCN, "IUCN Red List of Threatened Species. Version 2018-2", Published Jul. 6, 2018, downloaded Oct. 23, 2018 from http://www.iucnredlist.org/about/summary-statistics#TrendsInBiodiversityStatus); copyright International Union for Conservation of Nature and Natural Resources.
Naville et al., "Not so bad after all: retroviruses and long terminal repeat retrotransposons as a source of new genes in vertebrates," Clinical Microbiology and Infection, vol. 22 No. 4, Apr. 2016, p. 312-323.
NCBI, Complete genomes: Viruses (taxid 10239); downloaded on Oct. 5, 2018 from https://www.ncbi.nlm.nih.gov/genomes/GenomesGroup.cgi?taxid=10239; Listing of all viruses in the database.
NCBI, Complete genomes: Viruses (taxid 10239); downloaded on Oct. 5, 2018 from https://www.ncbi.nlm.nih.gov/genomes/GenomesGroup.cgi?taxid=10239; Listing of human viruses in the database.
NCBI, Complete genomes: Viruses (taxid 10239); downloaded on Oct. 5, 2018 from https://www.ncbi.nlm.nih.gov/genomes/GenomesGroup.cgi?taxid=10239; Listing of vertebrate viruses in the database.
Roossinck, "Move over bacteria! Viruses make their mark as mutualistic microbial symbionts", J Virol. Jul. 1, 2015; 89(13): 6532-6535.
Woolhouse et al., "Human viruses: discovery and emergence", Phil. Trans. R. Soc. B (2012) 367, 2864-2871.
Zimmer, "Mammals Made by Viruses", Discover Magazine, The Loom, Feb. 14, 2012; downloaded Oct. 5, 2018 from http://blogs.discovermagazine.com/loom/2012/02/14/mammals-made-by-viruses/.

CATIONIC POLYAMINES FOR TREATMENT OF VIRUSES

BACKGROUND

The invention relates to cationic polyamines for treatment of viral infections and methods thereof, and more specifically, to cationic modified polyethylenimines for anti-viral applications.

Treatment of viral infections continues to be elusive owing to the variance in virus structure (RNA, DNA, enveloped and non-enveloped viruses) together with their ability to rapidly mutate and acquire resistance. Viral diseases continue to be one of the leading causes of morbidity and mortality since ancient times. In recent years, viral infections have emerged as an eminent global public health problem mainly because of a rapid increase in human population, aging, climate change, and medical treatments that suppress the immune system, including irradiation therapy, anti-cancer chemotherapy and organ transplantation. For example, the worldwide outbreak of severe acute respiratory syndrome (SARS) in 2003, dengue fever, and bird flu (e.g., H1N1) outbreaks in Asia over the last two decades have imposed an enormous economic burden. More recently, several new viral pathogens like Nipah virus, Chikungunya virus (CHIKV), and mutated pandemic bird flu virus (e.g., H7N9) have been found in the human population. Consequently, significant effort has been directed to develop vaccines and anti-viral drugs to control and eradicate viral infections. However, the rapid mutation of viruses (especially flu virus), due to inherent genomic instability, makes vaccinations inefficient. Moreover, for many viral infections (e.g., dengue and Chikungunya viruses) there are no clinical drugs available. Since there are so many types and subtypes of pathogenic viruses that easily mutate to form drug-resistant strains, controlling them individually has not been possible.

Viruses can be classified into DNA and RNA viruses according to the genes they hold, as well as enveloped and non-enveloped viruses. This shows the complexity of the problem in attempting to design a general anti-viral agent. Most emerging and re-emerging viruses belong to the RNA type, including flavivirus family (e.g., dengue virus, or DENV), influenza, CHIKV, Enterovirus 71 (EV 71), and SARS Co-V. Many of these viruses exploit an endosomal pathway to infect cells. The low pH of the endosome allows introduction of viral genomes into cytoplasm. Furthermore, a number of enveloped viruses utilize anionic phosphatidylserine (PS)/TIM (T cell/transmembrane, immunoglobulin, and mucin) receptor binding and/or the apoptotic cell clearance pathway for entry to cells. This suggests that masking TIM receptors may provide new avenues for controlling viral infection.

Due to the existence of cationic and anionic regions on the viral surface, charged polymers potentially provide a means of exploiting electrostatic interactions to inhibit viral infections. However, attempts to prevent viral infections using anionic polymers (e.g., sulfated polysaccharides such as dextran, xylofuranan, ribofuranan and curdlan) to bind with cationic charges on the viral surface met limited success.

Heparin, extracted from animals, has strong activity against dengue virus, but has limited utility since it is an anti-coagulant.

Cationic polymers including cationic acrylate polymers, polyethylenimines and cationic poly(phenylene ethylene) polymers can also potentially interact with anionic groups of the viral surface by non-specific electrostatic interactions.

Polyethylenimines (PEIs) are polyamines that are commercially available in a broad range of molecular weights. The PEIs are formed as either linear (LPEI) or branched (BPEI) macromolecules. PEIs have found many applications in products, such as detergents, adhesives, water treatment agents, and cosmetics. Due to their ability to enter a cell through the cell membrane, PEIs have been utilized as drug carriers in biomedical applications. Polycationic PEIs can mediate gene transfer into mammalian cells in vitro and in vivo as a complex with DNA. However, cationic polymers such as linear polyethylenimine (PEI) exhibit high non-specific cytotoxicity towards mammalian cells and induce hemolysis. Moreover, the linear PEI is less water soluble than branched PEI.

A number of viral infections are pH-dependent, where low pH in the endosome is required for replication. Recently, niclosamide, an FDA approved anti-helminthic compound, was reported to prevent infections of pH-dependent viruses by neutralizing the endosomal pH. However, its highest selectivity was only ~24 against influenza virus (PR8) and human rhinovirus (HRV14). Ammonium chloride and chloroquine having pH neutralization ability were also reported to prevent viral infections, but they are highly toxic, limiting clinical applications.

An ongoing need exists for broad spectrum anti-viral agents that are non-hemolytic and that provide general and safe strategies to prevent viral infections. Anti-viral macromolecules with distinctive functional groups are needed to specifically bind to viral surface proteins as well as compete with viruses for immune cell/target cell binding to prevent infection.

SUMMARY

Accordingly, a method is disclosed, comprising:
treating a virus with a cationic polyamine, thereby forming a treated virus comprising the cationic polyamine bound by non-covalent interactions to the virus;
wherein:
i) the treated virus is less capable of entering a living mammalian cell and/or undergoing replication within a living mammalian cell compared to the untreated virus,
ii) the cationic polyamine comprises:
a plurality of non-charged N-acylated ethylenimine units of formula (1):

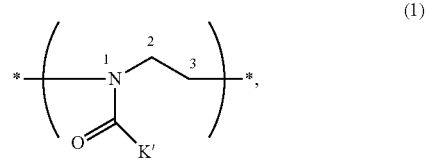

wherein each K' comprises at least one carbon and at least one alcohol hydroxyl group, and
a plurality of positive-charged secondary ethylenimine units of formula (3a):

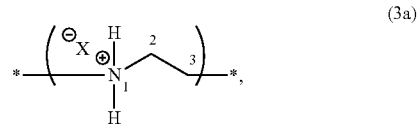

wherein the starred bond of the nitrogen is linked to a carbon and $X^\ominus$ is a negative-charged counterion bound by non-covalent association with the positive charged nitrogen, and iii) the cationic polyamine comprises the N-acylated ethylenimine units and the secondary ethylenimine units arranged in a random distribution and linked covalently head-to-tail, wherein nitrogen 1 of a given ethylenimine unit is linked to carbon 3 of a different ethylenimine unit.

Also disclosed is a method comprising:

treating a living mammalian cell with a cationic polyamine, thereby forming a treated cell comprising the cationic polyamine and the cell bound by non-covalent interactions;

wherein:

i) the treated cell has more resistance to a virus entering the treated cell and/or replicating within the treated cell compared to the untreated cell, ii) the cationic polyamine comprises:

a plurality of non-charged N-acylated ethylenimine units of formula (1):

$$\left( *-\underset{\underset{\underset{K'}{|}}{\underset{\|}{C}}}{\overset{2}{\underset{1}{N}}}-\overset{3}{\phantom{N}}-* \right) \quad (1)$$

wherein each K' comprises at least one carbon and at least one alcohol hydroxyl group, and a plurality of positive-charged secondary ethylenimine units of formula (3a):

$$\left( *-\overset{\overset{\ominus}{X} \overset{H}{\underset{\underset{H}{|}}{\overset{\oplus}{N}}}}{\phantom{N}}\overset{2}{\phantom{N}}\overset{3}{\phantom{N}}-* \right) \quad (3a)$$

wherein the starred bond of the nitrogen is linked to a carbon, and $X^\ominus$ is a negative-charged counterion bound by non-covalent association with the positive charged nitrogen, and iii) the cationic polyamine comprises the N-acylated ethylenimine units and the secondary ethylenimine units arranged in a random distribution and linked covalently head-to-tail, wherein nitrogen 1 of a given ethylenimine unit is linked to carbon 3 of a different ethylenimine unit.

Another method is disclosed, comprising:

administering to a patient infected with a virus a therapeutically effective amount of a cationic polyamine, thereby inhibiting and/or preventing replication of the virus;

wherein:

i) the cationic polyamine comprises:

a plurality of non-charged N-acylated ethylenimine units of formula (1):

$$\left( *-\underset{\underset{\underset{K'}{|}}{\underset{\|}{C}}}{\overset{2}{\underset{1}{N}}}-\overset{3}{\phantom{N}}-* \right) \quad (1)$$

wherein each K' comprises at least one carbon and at least one alcohol hydroxyl group, and a plurality of positive-charged secondary ethylenimine units of formula (3a):

$$\left( *-\overset{\overset{\ominus}{X} \overset{H}{\underset{\underset{H}{|}}{\overset{\oplus}{N}}}}{\phantom{N}}\overset{2}{\phantom{N}}\overset{3}{\phantom{N}}-* \right) \quad (3a)$$

wherein the starred bond of the nitrogen is linked to a carbon, and $X^\ominus$ is a negative-charged counterion bound by non-covalent association with the positive charged nitrogen, and ii) the cationic polyamine comprises the N-acylated ethylenimine units and the secondary ethylenimine units arranged in a random distribution and linked covalently head-to-tail, wherein nitrogen 1 of a given ethylenimine unit is linked to carbon 3 of a different ethylenimine unit.

The above-described and other features and advantages of the present invention will be appreciated and understood by those skilled in the art from the following detailed description, drawings, and appended claims.

DETAILED DESCRIPTION

Figure 1:
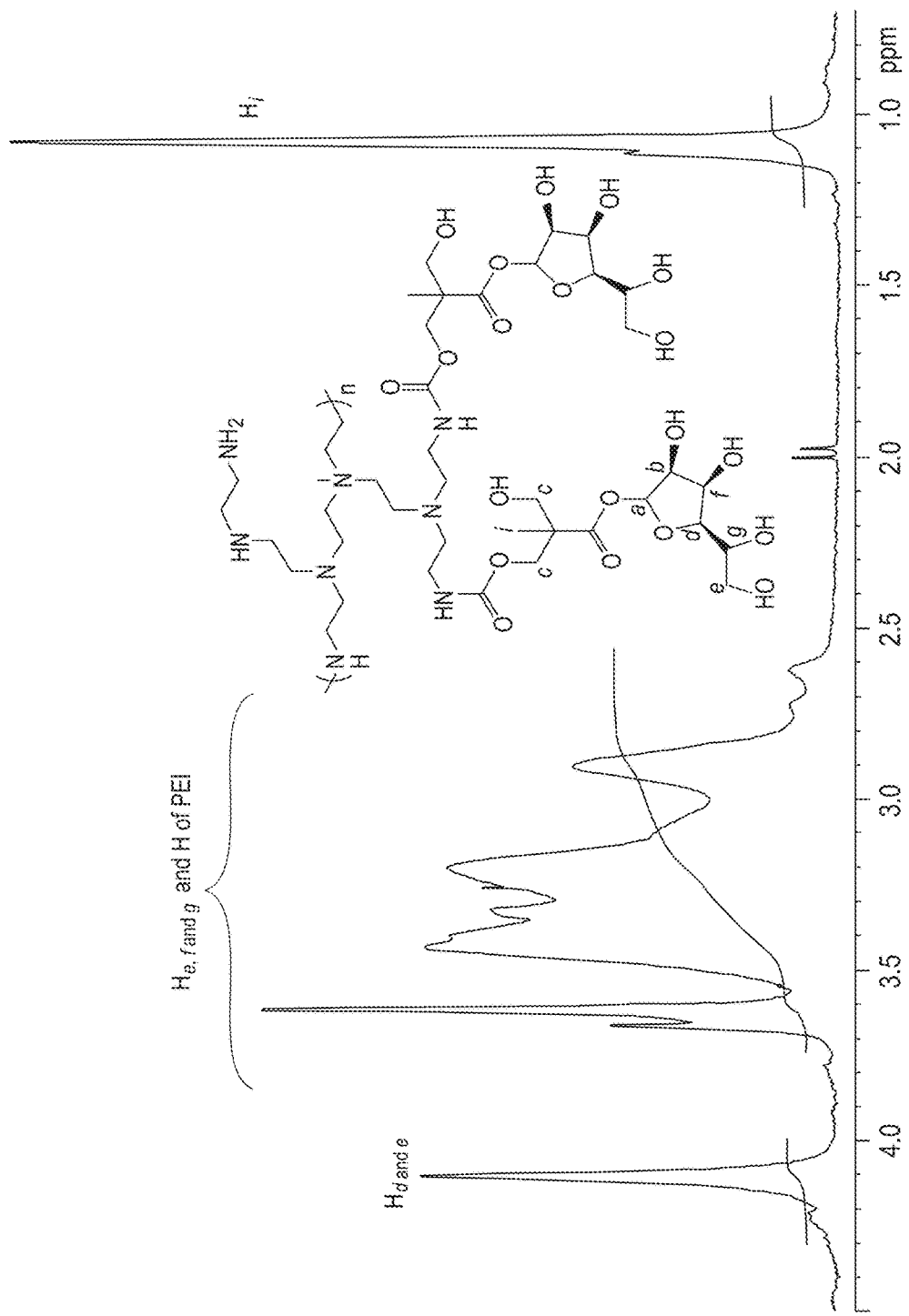
FIG. 1 is a $^1$H NMR spectrum of cationic polyamine B3 in CDCl$_3$.

Disclosed are methods of preventing, treating, and/or inhibiting a virus from entering and/or replicating in a mammalian cell. The methods utilize modified polyethylenimines (PEIs), referred to herein as cationic polyamines. The cationic polyamines comprise side chains having the general structure *—C(=O)—K' linked to respective backbone nitrogens, wherein K' comprises at least one carbon and at least one alcohol group. The cationic polyamines can comprise 1 to about 70 *—C(=O)—K' side chain groups linked to the primary and secondary amine groups of the PEI. Between 0% and about 70%, preferably about 20% to about 40%, of the total number of amine groups (i.e., primary, secondary and tertiary amine groups) of the PEI comprise a K' group. More than 0% and up to 100% of any remaining non-modified primary, secondary, and tertiary amine groups of the cationic polyamine are present in protonated form as an ammonium salt. In an embodiment, each K' group comprises a monosaccharide moiety (sugar moiety).

The cationic polyamines can compete with immune cells as well as target cells in binding with virus envelope proteins (E proteins), thereby impeding entry of the virus into a mammalian cell, alleviating stress on the immune system, and mitigating side effects due to immunodeficiency. Molecular docking computations reveal an unexpected and generally specific interaction of the cationic polyamines with viral surface proteins. Virus binding assays demonstrated significant reduction in infection after incubating virus with a cationic polyamine. The generality of this dynamic hydrogen-bonding specific interaction provides broad spectrum antiviral activity that appears to be immune to mutations, thereby mitigating and/or preventing development of viral resistance.

The cationic polyamines can also disrupt viral entry into a mammalian cell by binding to surface proteins and other molecules such as heparan sulfate proteoglycan of the cells. For example, the cationic polyamines can bind to TIM (T-cell immunoglobulin and mucin) receptor proteins, thereby inhibiting viruses that target TIM receptors of mammalian cells. The treated cells can have EC50 values (i.e., effective concentration of the cationic polyamine that inhibits 50% of the cells from viral infection) in a range of about 2.7 to about 6.8 mg/L, depending on the type of TIM receptor.

The pH buffering capacity of the cationic polyamines can also inhibit acid-driven endosomal release of the virus, thereby impeding viral replication.

The cationic polyamines can inhibit one or more viruses. Representative viruses include dengue virus (e.g., DENV-1, DENV-2, DENV-3, and/or DENV-4), influenza virus (A/H3N2), CHIKV (Chikungunya virus), SARS Co-V (SARS corona virus), EV 71 (Enterovirus 71), and herpes simplex viruses (e.g., HSV-1 and HSV-2). In some instances, viral activity was effectively inhibited at cationic polyamine concentration as low as 0.012 mg/L, with high selectivity over mammalian cells. The cationic polyamines can be non-cytotoxic and non-hemolytic to mammalian cells at the effective concentration against the virus.

Cationic Polyamines

The cationic polyamines comprise at least one polymer branch having a polymer backbone that comprises a plurality of repeat units referred to herein as ethylenimine units. Each of the ethylenimine units has 1 backbone nitrogen and 2 backbone carbons arranged as follows:

$$*-\!\!\left(\!\!\underset{1}{N}\!\!-\!\!\underset{}{\overset{2}{C}}\!\!-\!\!\underset{3}{C}\!\!\right)\!\!-\!\!*.$$

Herein, starred bonds represent attachment points, not methyl groups. It should be understood that the nitrogen labeled 1 is trivalent and each carbon is tetravalent. Other substituents on the carbons and nitrogen are not shown in the above structure. The nitrogen labeled 1 represents the head of a given ethylenimine unit, and the carbon labeled 3 represents the tail of a given ethylenimine unit. Adjacent ethylenimine units are covalently linked head to tail (the starred bond of nitrogen 1 of a given ethylenimine unit is linked to carbon 3 of an adjacent ethylenimine unit).

The cationic polyamines can be effective anti-viral agents without having a backbone nitrogen in the form of a quaternary ammonium salt. Herein, a quaternary ammonium salt comprises a positive-charged nitrogen that is covalently linked only to carbons (e.g., 4 carbons) and is non-covalently associated with a negative-charged counterion $X^{\ominus}$. The positive charged nitrogen of a quaternary ammonium salt is not covalently bound to any hydrogen. In an embodiment, the cationic polyamine structure excludes any backbone nitrogen in the form of quaternary ammonium salt.

The cationic polyamines comprise one or more polymer chains (branches) comprising ethylenimine units. A linear cationic polyamine comprises i) one branch comprising a plurality of ethylenimine units and ii) two polymer chain end groups (also referred to as peripheral end groups, or dangling end groups). A branched cationic polyamine comprises two or more intersecting branches comprising ethylenimine units, and three or more peripheral end groups.

Scheme 1 illustrates examples of the alternating arrangement of backbone carbon pairs and backbone nitrogens of the ethylenimine units of a linear cationic polyamine and of a branched cationic polyamine having two branches. The

*—C—C—N—* unit enclosed in parentheses represents an ethylenimine unit. End groups, charges, counterions and substituents of the backbone carbons and nitrogens are not shown.

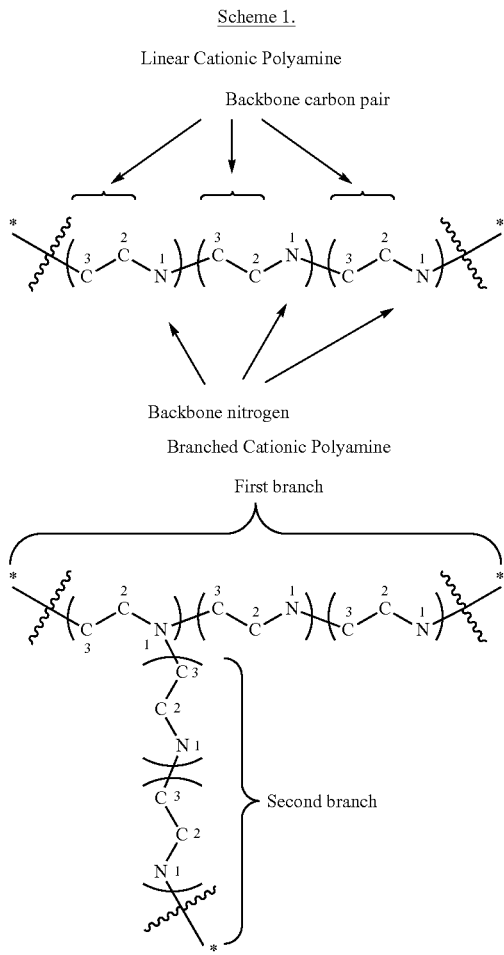

Scheme 1.

Linear Cationic Polyamine

Backbone carbon pair

Backbone nitrogen

Branched Cationic Polyamine

First branch

Second branch

As shown above, adjacent *—C—C—N—* units are linked head to tail (i.e., nitrogen 1 of one ethylenimine unit is linked to carbon 3 of an adjacent ethylenimine unit).

Backbone primary, secondary, and tertiary amine nitrogens of the cationic polyamine can be present as ammonium salts of a protic acid (i.e., primary ammonium salt, secondary ammonium salt, or tertiary ammonium salt). A primary ammonium salt comprises a positive-charged nitrogen covalently linked to 1 carbon and 3 hydrogens, and non-covalently associated with a negative-charged counterion. A secondary ammonium salt comprises a positive-charged nitrogen covalently linked to 2 carbons and 2 hydrogens, and non-covalently associated with a negative-charged counterion. A tertiary ammonium salt comprises a positive-charged nitrogen covalently linked to 3 carbons and 1 hydrogen, and non-covalently associated with a negative-charged counterion.

The cationic polyamines comprise at least one non-charged N-acylated ethylenimine units of formula (1):

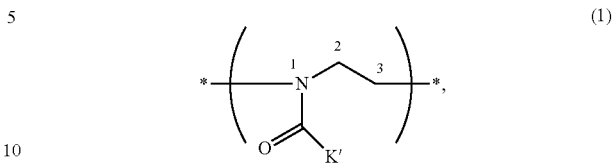

wherein each K' is a group comprising at least one carbon and at least one alcohol hydroxy group.

The cationic polyamines further comprise a plurality of ethylenimine units independently selected from the group consisting of:

i) protonated primary ethylenimine units of formula (2a):

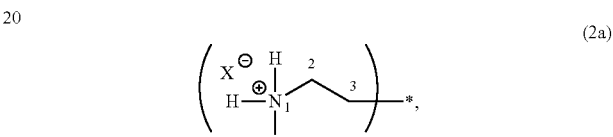

ii) non-protonated primary ethylenimine units of formula (2b):

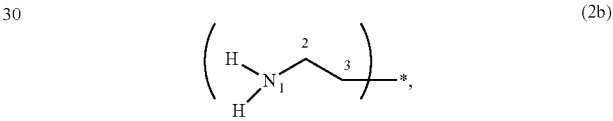

iii) protonated secondary ethylenimine units of formula (3a):

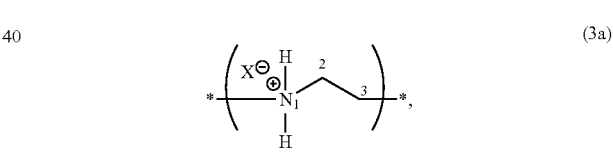

wherein the starred bond of the nitrogen is linked to a carbon, iv) non-protonated secondary ethylenimine units of formula (3b):

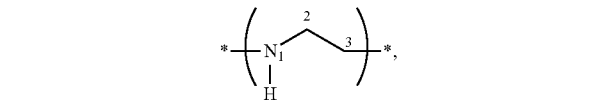

wherein the starred bond of the nitrogen is linked to a carbon, v) protonated tertiary ethylenimine units of formula (4a):

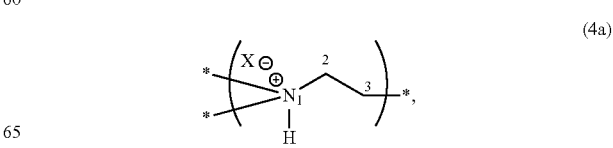

wherein the starred bond of the nitrogen is linked to different carbons, and vi) non-protonated tertiary ethylenimine units of formula (4b):

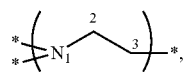
(4b)

wherein the starred bonds of the nitrogen are linked to different carbons. More than 0% of the ethylenimine units are present in protonated form.

In each of the above structures and those that follow, $X^{\ominus}$ is a negative-charged counterion bound by non-covalent interactions with the positive-charged nitrogen labeled 1. Exemplary negative-charged counterions include halides (e.g., fluoride, chloride, bromide, iodide), nitrate, hydroxide, methane sulfonate, and carboxylates (e.g., acetate, benzoate). In an embodiment, $X^{\ominus}$ is chloride. The cationic polyamine comprise $X^{\ominus}$ groups singularly or in combination.

K' groups include cyclic and non-cyclic groups, aromatic and non-aromatic groups, and combinations thereof, comprising one or more alcohol hydroxy groups. In an embodiment, K' is selected from the group consisting of hydroxyalkylene groups, hydroxyalkylenoxy groups, groups comprising a catechol group, and groups comprising a monosaccharide group (sugar moiety). Monosaccharide groups include stereospecific and non-stereospecific forms of hexose sugars, in particular those of mannose, glucose, and galactose. These are exemplified in Scheme 2.

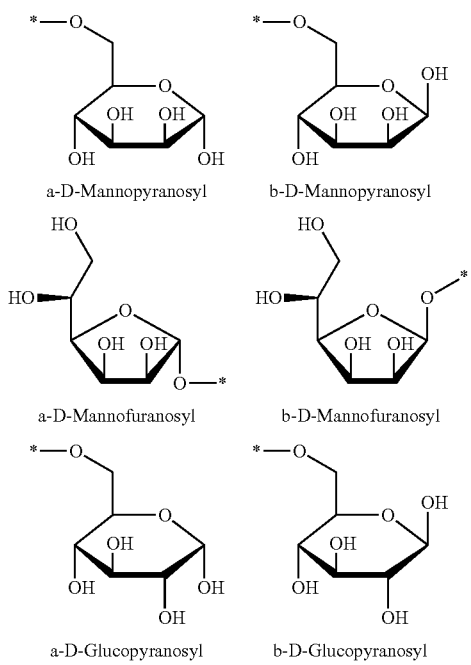

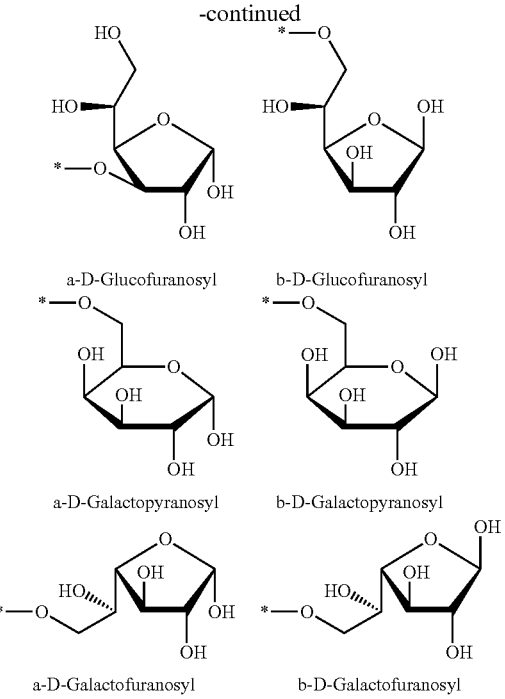

The monosaccharide moiety can be linked to the carbonyl group of formula (1) by any suitable linking group including a single bond.

The linking group joining the carbonyl group of formula (1) to the sugar moiety can be linked to any one of the alcohol hydroxy groups of the sugar moiety.

Non-limiting examples of *—C(=O)K' groups include those of Scheme 3.

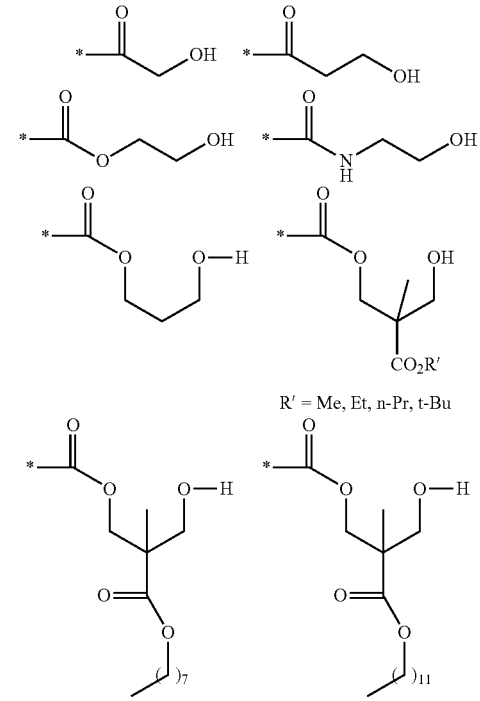

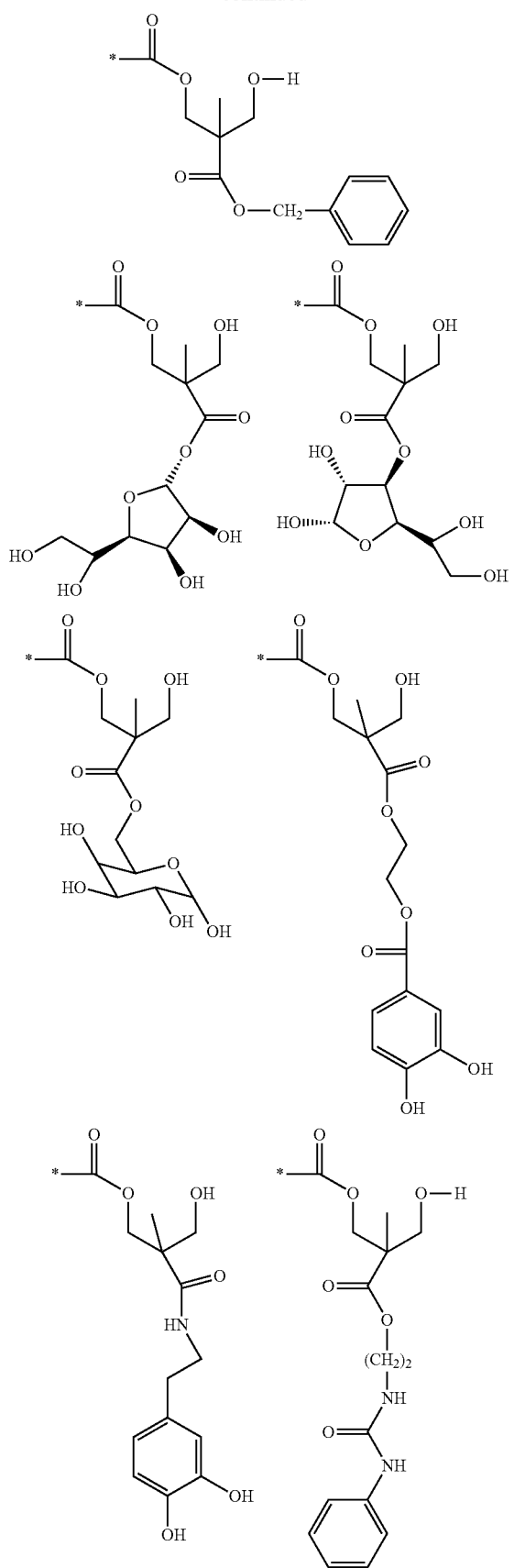

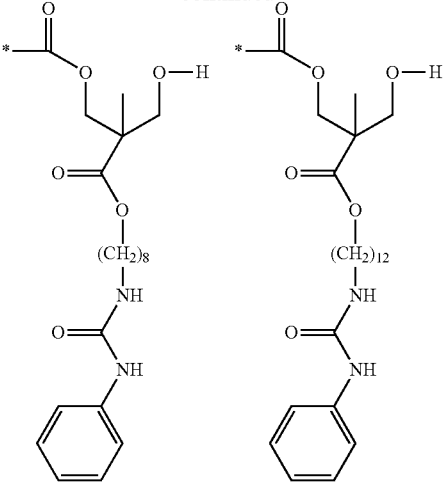

In the above structures the starred bond is linked to the carbonyl group of formula (1). The backbone nitrogen of formula (1) can complete an amide group, carbamate, or a urea group with the carbonyl group linked to K'. The cationic polyamine can comprise the K' groups singularly or in combination.

The cationic polyamine backbone comprises the ethylenimine units covalently linked in a head to tail arrangement. Herein, "covalently linked" means directly and/or indirectly covalently linked. "Directly covalently linked" means joined together by a single covalent bond. "Indirectly covalently linked" means covalently linked by way of a linking group. For example, a portion of the chemical structure of the cationic polyamine that contains one or more other ethylenimine units of the polymer backbone of the cationic polyamine can be a linking group, which covalently links an N-acylated ethylenimine unit to a protonated secondary ethylenimine unit.

The cationic polyamines can further comprise one or more oxidized ethylenimine units of formula (5):

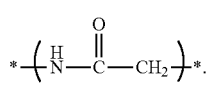

(5)

The cationic polyamines can further comprise one or more amide ethylenimine units of formula (6):

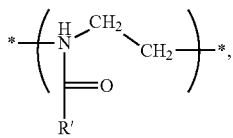

(6)

wherein R' is methyl, ethyl, propyl, or butyl.

Protonated and non-protonated tertiary ethylenimine units serve as junction points for intersecting branches. Protonated and non-protonated primary ethylenimine units serve as branch terminating units. Herein, a hydrogen linked to a nitrogen of a primary ethylenimine unit can be a polymer chain end group. The cationic polyamines can have other polymer chain end groups.

The cationic polyamines comprise at least one N-acylated ethylenimine unit of formula (1) and at least one cationic ethylenimine unit selected from the group consisting of formula (2a), formula (3a), and formula (4a). More specific cationic polyamines comprise about 100 to about 400 ethylenimine units, wherein 1 to about 200 of the ethylenimine units are N-acylated ethylenimine units of formula (1). Still more specific cationic polyamines comprise about 200 to about 300 ethylenimine units, wherein 1 to about 170 of the ethylenimine units are N-acylated ethylenimine units formula (1). Still more specific cationic polyamines comprise about 200 to about 300 ethylenimine units, wherein 1 to about 50 of the ethylenimine units are N-acylated ethylenimine units formula (1).

The end groups of the linear cationic polyamine can be any suitable end groups such as, for example, hydrogen, alkyl groups, amine groups, hydroxyalkyl groups, and combinations thereof.

A linear cationic polyamine comprises 1 polymer branch comprising a polyethylenimine backbone. More specific linear cationic polyamines comprise 100 to 400 ethylenimine units, of which 1 to about 200 are N-acylated ethylenimine units of formula (1). The balance of the ethylenimine units of the linear cationic polyamine can be secondary ethylenimine units of formula (3a) and (3b). In an embodiment, the linear cationic polyamine comprises 1 to about 50 oxidized ethylenimine unit of formula (5). In another embodiment, the linear cationic polyamine comprises 1 to about 30 amide ethylenimine units of formula (6).

A branched cationic polyamine comprises 2 or more intersecting polymer branches, wherein each of the branches comprises a polyethylenimine backbone. More specific branched cationic polyamines comprise 100 to 400 ethylenimine units, of which 1 to about 170 are N-acylated ethylenimine units of formula (1). The remaining ethylenimine units includes at least 1 tertiary ethylenimine unit and at least 1 secondary ethylenimine unit. At least one of the remaining ethylenimine units is a positive-charged ethylenimine unit of formula (2a), (3a), or (4a). In an embodiment, the branched cationic polyamine comprises 1 to about 50 oxidized ethylenimine units of formula (5). In another embodiment, the branched cationic polyamine comprises 1 to about 30 amide ethylenimine units of formula (6).

The cationic polyamines can have a number average molecular weight (Mn) of about 500 to about 100000, more particularly about 1500 to about 60000, and most particularly about 5000 to about 60000.

The cationic polyamine can comprise 1 to about 200, more particularly 1 to about 150, and most particularly about 4 to about 100 ethylenimine units of formula (1). In an embodiment, the cationic polyamine has a branched polyethylenimine backbone structure and comprises about 4 to about 150 ethylenimine units of formula (1). In another embodiment, the cationic polyamine has a branched polyethylenimine backbone structure and comprises about 4 to about 150 ethylenimine units of formula (1), wherein K' of formula (1) comprises a mannose moiety. In another embodiment, the cationic polyamine has a linear polyethylenimine backbone structure and comprises about 1 to about 70 ethylenimine units of formula (1), wherein K' of formula (1) comprises a mannose moiety.

Preparation of Linear Cationic Polyamines

The cationic polyamines can be prepared from a basic form of a polyethylenimine or a partially N-acylated polyethylenimine. These base polyamines comprise at least one non-protonated ethylenimine unit of formula (7):

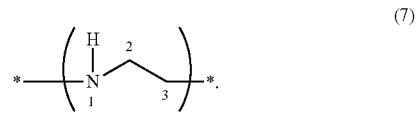

More particularly, linear cationic polyamines can be prepared from base polyamines that are partially or fully hydrolyzed poly(2-alkyloxazoline)s. Poly(2-alkyloxazoline)s can be prepared by cationic ring opening polymerization of 2-alkyl oxazolines (Scheme 4).

Scheme 4.

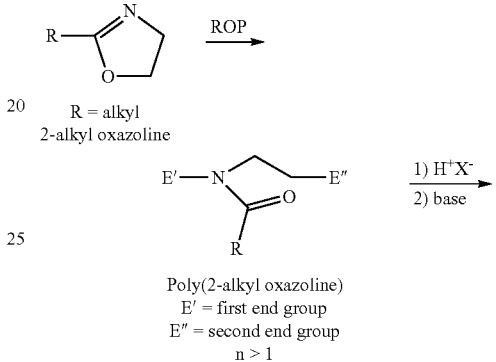

R = alkyl
2-alkyl oxazoline

Poly(2-alkyl oxazoline)
E' = first end group
E" = second end group
n > 1

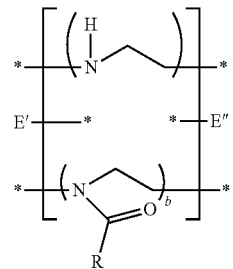

The ring opening polymerization (ROP) of the 2-alkyl oxazoline can be initiated by a cationic initiator $E'^+$, which becomes a first end group E'. E" is a chain terminating second end group. R is typically a $C_1$-$C_{10}$ alkyl group, more particularly $C_1$-$C_4$ alkyl group. Partial hydrolysis of a poly (2-alkyl oxazoline) using a protic acid followed by neutralization of the hydrolyzed polymer yields a partially hydrolyzed non-protonated poly(2-alkyloxazoline) as shown in Scheme 4, where a+b=n, and a>0 and b>0. A fully hydrolyzed poly(2-alkyloxazoline) is a linear polyethylenimine (LPEI) homopolymer (a=n and b=0). The ethylenimine units of the partially or fully hydrolyzed poly(2-alkyloxazoline) are linked head to tail. In the above bracket notation of Scheme 2, the vertical stacking of the ethylenimine units within the square brackets indicates a random distribution of the ethylenimine units of the polymer chain. The commercial basic form of a partially hydrolyzed poly(2-alkyloxazoline) is hemolytic, whereas the protonated partially hydrolyzed poly(2-alkyloxazoline) can be less hemolytic.

A method of preparing an antiviral linear cationic polyamine comprises forming a mixture comprising a base linear polyethylenimine (base LPEI, which can be a partially or fully hydrolyzed poly(2-alkyloxazoline)) and an organic solvent (e.g., chloroform) suitable for conducting an N-acylation. The mixture is optionally heated at an elevated temperature for a period of time sufficient to dissolve the base LPEI. The dissolved base LPEI is then treated with one or more N-acylating agents, followed by treatment with a protic acid (e.g., methanol/HCl), thereby forming a linear cationic polyamine (modified LPEI) containing ethylenimine units of formula (1).

Oxidized ethylenimine units of formula (5) can be introduced into a base LPEI by treating a mixture comprising the base LPEI and an organic solvent with air and/or a peroxide. This treatment can be performed at any suitable temperature. Treatment of the oxidized base LPEI with an N-acylating agent followed by acidic workup results in a cationic polyamine comprising ethylenimine units of formula (1) and oxidized ethylenimine units of formula (5). The backbone amide groups introduced by oxidation can potentially also improve biocompatibility, biodegradability, and/or lower red blood cell toxicity.

Preparation of Branched Cationic Polyamines

The branched cationic polyamines are preferably prepared from a branched polyethylenimine (branched PEI or BPEI), which can be formed, for example, by ring opening polymerization of aziridine. The branched PEI has 2 or more intersecting polymer chains (branches) comprising backbone nitrogens in the form of primary amine nitrogens, secondary amine nitrogens, and tertiary amine nitrogens, which are alternatingly spaced by backbone ethylene groups (*—$CH_2CH_2$—*). The branched PEI comprises:

i) 1 or more secondary ethylenimine units of formula (8):

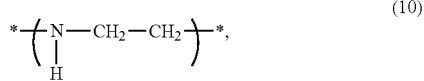
(10)

ii) 1 or more tertiary ethylenimine units of formula (9):

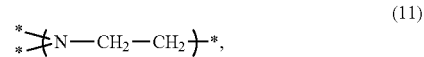
(11)

which serve as junction points for intersecting branches, and
iii) 2 or more primary ethylenimine units of formula (12):

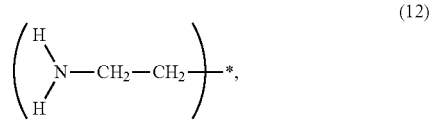
(12)

which serve as branch terminating end units.
A branched PEI is also represented herein by formula (13):

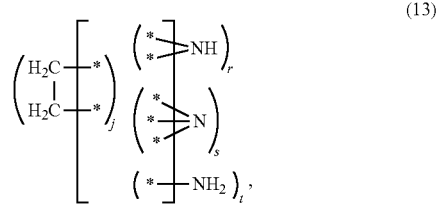
(13)

wherein j, r, s, and t represent average numbers of the respective independent functional groups of a BPEI macromolecule. Subscript j has an average value greater than or equal to 4, and r+s+t has an average value greater than or equal to 4. It should be understood by the notation of formula (13) that each set of parentheses ( ) beginning inside the square brackets [ ] and ending outside the square brackets encloses an independent functional group of the BPEI, not a polymer chain. Additionally, the atoms having starred bonds represent attachment points to the atoms having starred bonds on the opposite bracket. Additionally, the vertical stacking of the functional groups indicates a random distribution of the stacked functional groups in the branched PEI. Each starred bond of a given nitrogen on the right square bracket is linked to a different ethylene group on the left square bracket, and each starred bond of an ethylene group on the left square bracket is linked to a different nitrogen on the right square bracket, consistent with the head to tail arrangement of adjacent ethylenimine units.

In an embodiment, j has an average value of about 180 to about 360, r has an average value of about 90 to about 140, s has an average value of about 45 to about 70, t has an average value of about 45 to about 70, and (r+s+t) has an average value of about 180 to about 360. In another embodiment, the branched polyethylenimine has a weight average molecular weight (Mw) greater than 1000.

As an example, a commercially available branched polyethylenimine has a weight average molecular weight (Mw) of about 25,000, a number average molecular weight (Mn) of about 10,000, and contains an average of 233 ethylene groups (j), 116 backbone secondary nitrogens (r), 58 backbone tertiary nitrogens (s), and 58 primary amine nitrogens (t), based on Mn and an average ethylenimine unit molecular weight equal to 43. In this instance, j=233, r=116, s=58, and t=58. This material is referred to herein as BPEI25.

As another example, a commercially available branched polyethylenimine has a weight average molecular weight (Mw) of about 2000, a number average molecular weight (Mn) of about 1800, and contains an average of 40 ethylene groups (j), 20 backbone secondary nitrogens (r), 10 backbone tertiary nitrogens (s), and 10 primary amine nitrogens (t), based on Mn and an average ethylenimine unit molecular weight equal to 43. In this instance, j=40, r=20, s=10, and t=10. This material is referred to herein as BPEI1.8.

A branched cationic polyamine can be prepared by treating a base form of a branched PEI with an N-acylating agent capable of introducing one or more of the above-described N-acyl groups. Treatment of the modified branched PEI with a protic acid provides the branched cationic polyamine.

If desired, the branched PEI and/or the modified branched PEI can be oxidized as described above to introduce oxidized ethylenimine units of formula (5) for minimizing hemolysis and/or enhancing biodegradability. The oxidation can occur before, during, and/or after formation of the modified branched PEI.

The BPEI used to form the cationic polyamine can have a number average molecular weight (Mn) of about 1000 to about 75,000.

Two BPEIs were utilized in the examples further below, designated BPEI1.8 and BPEI25. BPEI1.8 has Mw of about 2000 and a number average molecular weight (Mn) of about 1800. BPEI25 has Mw of about 25,000 and Mn of about 10,000.

BPEIs can have a high number of cationic charges and strong capacity to neutralize the endosomal pH. The modified BPEIs can also have a buffering capacity that can be varied by choice of molecular weight and/or degree and type of functionalization of the BPEI. The large number of primary amine groups provide sites for subsequent transformations and installation of a wide variety of functional groups. In this way polymer/cell interactions, polymer/virus interactions, and cytotoxicity can be adjusted.

End Groups

No restriction is placed on the cationic polyamine end groups with the proviso that the end group does not degrade the antiviral properties of the polymer.

A linear cationic polyamine comprises a first end group E linked to a backbone nitrogen (labeled 1 above) of an ethylenimine unit. Exemplary first end groups include hydrogen or $C_1$-$C_{10}$ alkyl or aryl. A linear cationic polyamine can comprise a second end group E' linked to a terminal carbon (labeled 3 above) of an ethylenimine unit. Exemplary second end groups include primary amine groups (*—$NH_2$), hydroxy groups (*—OH), and acylated derivatives thereof resulting from reaction with the N-acylating agents. The end groups of a branched cationic polyamine can consist essentially of primary ethylenimine units of formula (9) and acylated derivatives thereof. The linear and branched cationic polyamines can have other end groups.

Alkyl end groups are exemplified by the following chain terminating units of the cationic polyamine:
i) secondary ethylenimine units linked to an alkyl substituent $R^e$, having formula (14):

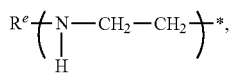
(14)

wherein $R^e$ is a $C_1$-$C_{10}$ alkyl or aryl group, and
ii) acylated ethylenimine units linked to an alkyl substituent $R^e$, having formula (15):

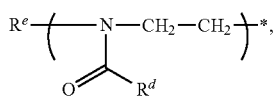
(15)

wherein $R^e$ is a $C_1$-$C_{10}$ alkyl or aryl group, and $R^d$ is a $C_1$-$C_{10}$ alkyl group. In an embodiment, $R^e$ is methyl or ethyl.

Hydroxy end groups are exemplified by the following chain terminating units of linear PEI:
i) protonated secondary ethylenimine units linked to a hydroxy group:

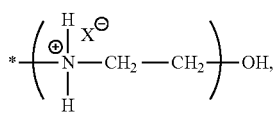

and
ii) acylated ethylenimine units linked to a hydroxy group:

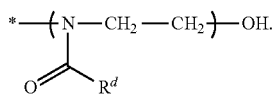

Amino end groups are exemplified by the following chain terminating units of linear PEI:
i) secondary ethylenimine units linked to a protonated primary amine group:

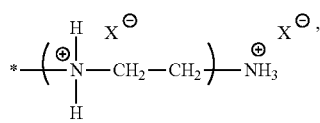

and
ii) acylated ethylenimine units linked to a protonated primary amine group:

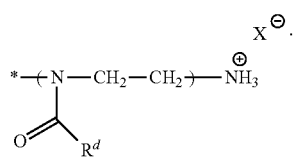

Other end groups include alkoxy, thiol (*—SH), and substituted protonated secondary and tertiary amine groups. Other end groups include derivatives of any of the foregoing groups (e.g., esters and amides of hydroxy and amino end groups, respectively). The cationic polyamine can comprise the end groups singularly or in combination.

N-Acylating Agents

The N-acylating agent is a compound capable of reacting with primary or secondary amine nitrogen of the PEI backbone in one or more process steps to form an ethylenimine unit of formula (1) comprising a side chain *—C(=O)K', where K' contains at least one alcohol group.

The N-acylating agent comprises an active group for coupling to the PEI nitrogen. Non-limiting active groups for N-acylation include carboxylic acid chlorides, carboxylic acid anhydrides, active esters, active carbonates, cyclic carbonates, lactones, isocyanates, and active carbamates.

The N-acylating agent can comprise a protected alcohol group, which can be deprotected after the N-acylation.

The N-acylating agent can comprise a latent form of an alcohol group (e.g., the alcohol group that is formed as a result of the N-acylation as in ring opening of a cyclic carbonate).

Based on these considerations, it will be apparent to skilled artisans that many compounds are available or can be readily prepared for introduction of the *—C(=O)K' side chain.

Preferred N-acylating agents include cyclic carbonates, which can introduce an alcohol group in one step. Exemplary cyclic carbonates include those of Scheme 5.

Scheme 5.
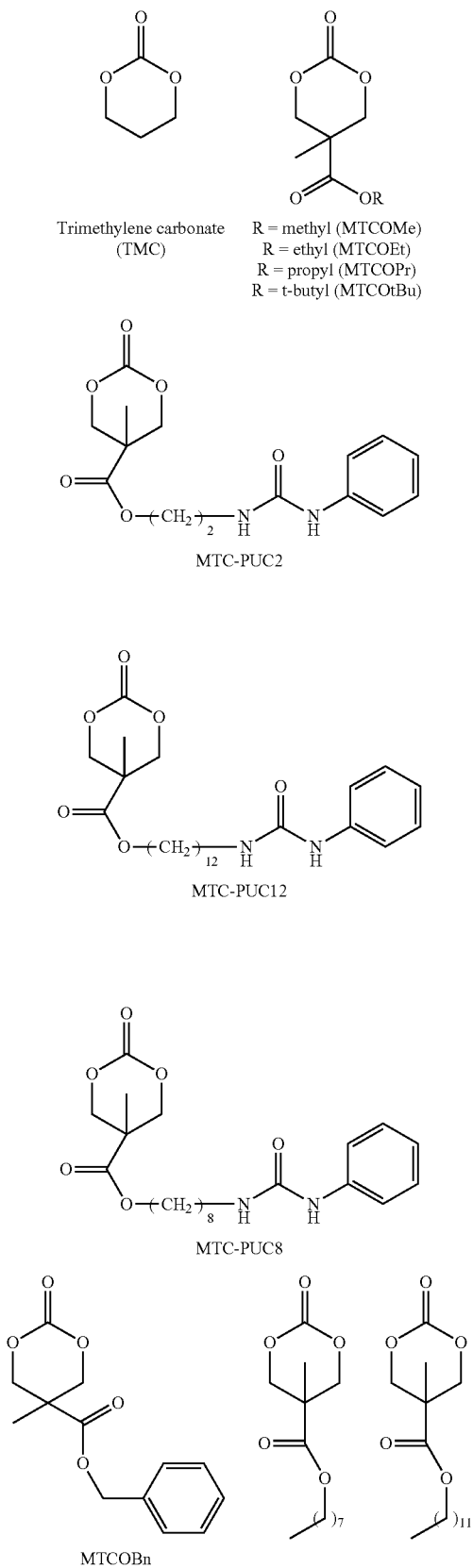
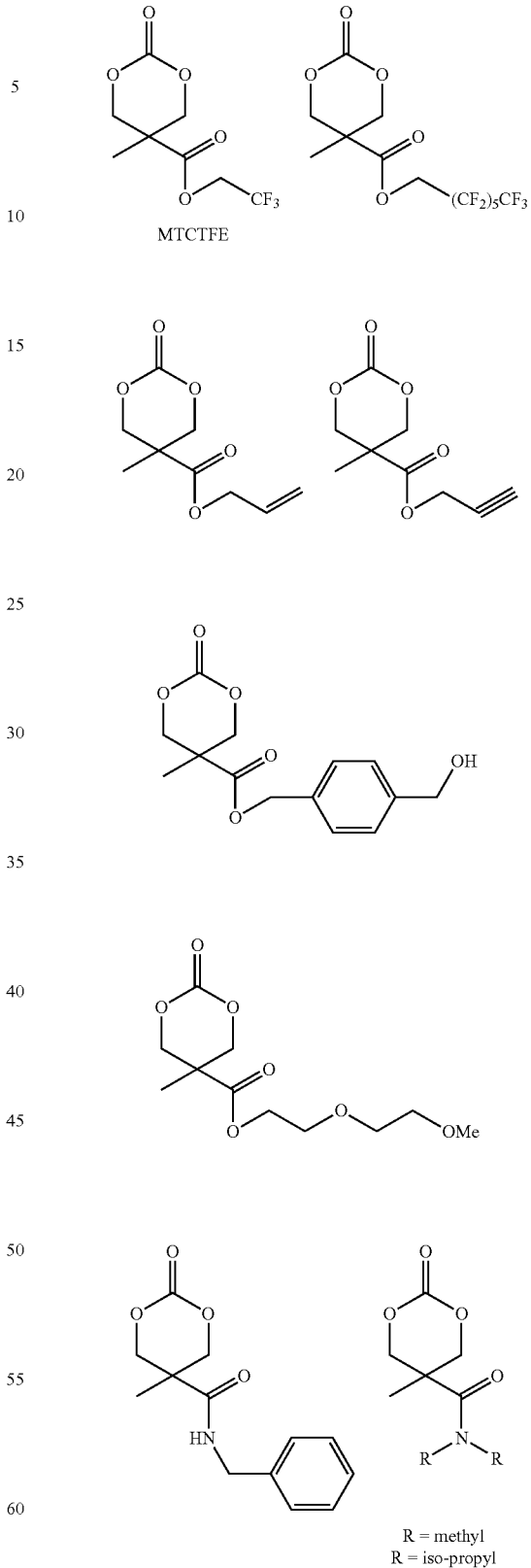
Other preferred cyclic carbonates comprise a protected and/or unprotected alcohol groups of a sugar moiety or a catechol group such as, for example, those of Scheme 6.

Scheme 6.

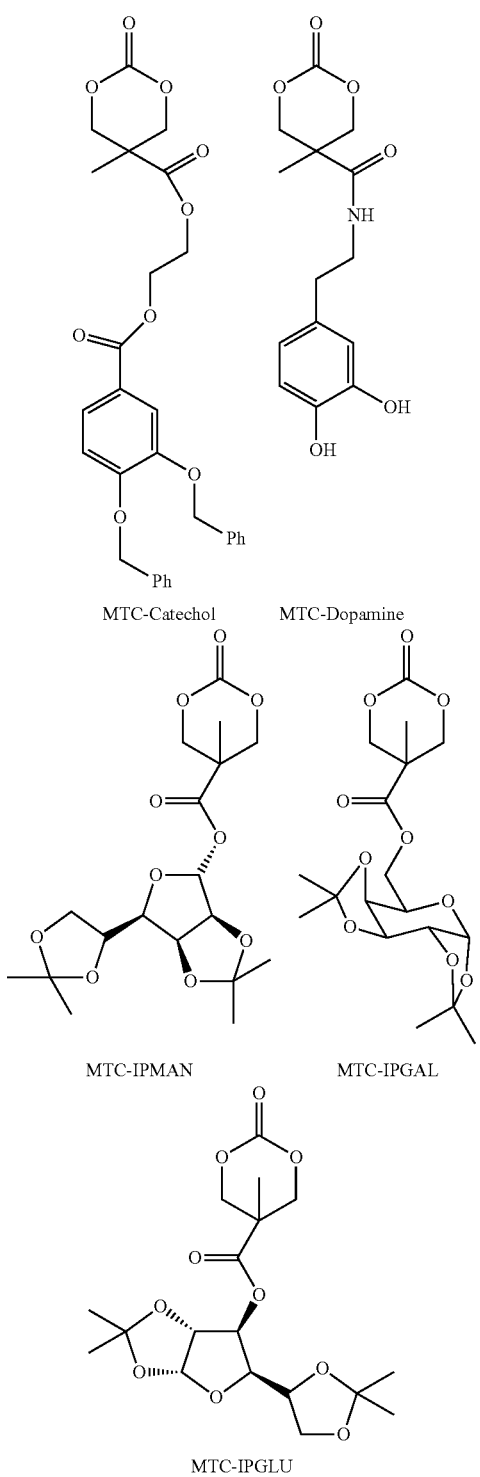

Antiviral Properties

For the examples further below, the following definitions are applicable.

EC50 is defined as the concentration (in mg/L) of cationic polyamine at which 50% of the test mammalian cells are not infected by a virus in a given response time. Small EC50 values are desirable.

CC50 is defined as the concentration (in mg/L) of cationic polyamine at which 50% of the test mammalian cells are killed in a given response time. High CC50 values are desirable.

Viral selectivity is defined as the CC50/EC50. High viral selectivity values are desired.

LD50 is defined as the dose in milligrams of cationic polyamine per kilogram of test animal at which 50% of a test population (e.g., mice) is killed in a given response time. High LD50 values are desirable.

A first method of inhibiting a virus comprises contacting the virus with a cationic polyamine before the virus contacts a mammalian cell, thereby forming a complex comprising the virus and the cationic polyamine bound by non-covalent interactions, thereby inhibiting the virus from infecting the cell. The buffering capacity of the bound cationic polyamine can also potentially impede endosomal release of the virus from the complex, thereby inhibiting viral replication. Non-limiting exemplary mammalian cell include blood cells, liver cells, nasal cells, lung cells, and cervical cells.

A second method inhibiting a virus comprises contacting a membrane of a mammalian cell with a cationic polyamine before the cell contacts a virus, thereby forming a complex comprising the cationic polyamine bound by non-covalent interactions to the cell membrane, wherein the complex inhibits and/or blocks the virus from entering the cell. In an embodiment, the cationic polyamine is bound to a TIM receptor of the cell membrane.

Also disclosed is a method of treating a patient afflicted with a disease caused by a virus, comprising administering a therapeutically effective amount of a disclosed cationic polyamine to the patient, thereby inhibiting and/or curing the disease. In an embodiment, the cationic polyamine is administered by injection. In another embodiment, the cationic polyamine is administered as a solution in the form of a nasal spray or inhalation spray. In another embodiment, the cationic polyamine is administered orally.

Further disclosed is a method of treating and/or preventing a medical condition caused by a virus by contacting the virus with a disclosed cationic polyamine, thereby inhibiting the virus from infecting and/or replicating in a mammalian cell.

Also disclosed is a medical composition for preventing and/or treating a viral infection, comprising one or more of the above-described cationic polyamines. The medical composition can be a drug. No restriction is placed on the manner of administration of the drug. The drug can have the form of a solution, gel, powder, pill, paste, or ointment. The drug can comprise water. The drug can be administered as an ingestable solid (e.g., pill), an ingestable liquid (e.g., a drink), as a rinse solution (e.g., mouthwash, other hygiene rinse), as intravenous injection, as a spray (e.g., nasal spray), as an inhalant, as a dermal patch, as a liquid drop (e.g., eye drops), and/or as a topically applied ointment (e.g., lotion).

The low average mass, high antiviral activity, and low in vivo toxicity (i.e., high LD50 in mice by intravenous injection) of the cationic polyamines makes these materials attractive as broad spectrum antiviral agents for a wide range of medical uses, including treating and/or preventing viral infections.

The following examples demonstrate the preparation and properties of the antiviral cationic polyamines. Non-covalent interactions of virus surface proteins with the mannose functionalized branched polyethylenimine were found. Interactions with respect to binding and prevention of virus uptake appear to be generally applicable to a wide variety of viruses. Other interactions such as the number of hydrogen-bonds required to form a viral/polymer complex can be virus specific. The supramolecular polymer-virus interactions provide broad spectrum activity with high selectivity. The generality of this hydrogen-bonded virus/polymer complex appears to be unaffected by subsequent viral mutation, which aids in preventing the onset of viral resistance. Thus, the polymer/virus complex can be exploited to prevent viral infection.

EXAMPLES

Materials used in the following examples are listed in Table 1.

TABLE 1

| ABBREVIATION | DESCRIPTION | SUPPLIER |
|---|---|---|
| BPEI1.8 | Branched Polyethylenimine, Mw = 2000, Mn = 1800, 10 primary amine groups, 20 secondary amine groups and 10 tertiary amine groups | Sigma-Aldrich |
| BPEI25 | Branched Polyethylenimine, Mw = 25000, Mn = 10000, PDI 2.5, 58 primary amine groups, 116 secondary amine groups and 58 tertiary amine groups | Sigma-Aldrich |
| LPEI25 | Linear Polyethylenimine Mw = 25000, Mn = 10950, PDI 1.16; 2 primary amine end groups, 246 secondary amine groups, 8 acylated amine groups. | Polysciences |
| MTT | (3-(4,5-Dimethylthiazol-2-yl)-2,5-diphenyltetrazolium bromide | Sigma-Aldrich |
| IPMAN | 2,3;5,6-Di-O-Isopropylidene-D-Mannofuranose | Sigma-Aldrich |
| HEPES | 4-(2-Hydroxyethyl)-1-Piperazineethanesulfonic Acid | Invitrogen |
| EMEM | Eagle's Minimum Essential Medium | Sigma-Aldrich |
| DMEM | Dulbecco's Modified Eagle's Medium | Biowest |
| FBS | Fetal Bovine Serum | Invitrogen |
| PBS | Phosphate Buffered Saline | Sigma-Aldrich |
| PBMC | Peripheral Blood Mononuclear Cell | |
| NITD008 | (2R,3R,4R,5R)-2-(4-aminopyrrolo[2,3-d]pyrimidin-7-yl)-3-ethynyl-5-(hydroxymethyl)oxolane-3,4-diol | Novartis |
| DBU | 1,8-Diazabicyclo[5,4,0]undec-7-ene | Sigma-Aldrich |
| TMC | Trimethylene Carbonate | Sigma-Aldrich |
| Bis-MPA | 2,2-Dimethylol-Propionic Acid | Sigma-Aldrich |
| PFC | Bis-pentafluorophenyl carbonate | Iris Biotech GmbH |

Herein, Mn is the number average molecular weight, Mw is the weight average molecular weight, and MW is the molecular weight of one molecule.

Solid branched polyethylenimine (BPEI25, Mn 10,000, PDI 2.5) was freeze-dried prior to use.

Peripheral blood mononuclear cells (PBMC) and macrophages were derived from human blood from healthy adult individuals after informed consent.

Anhydrous solvents were dried using activated alumina columns and stored over molecular sieves (3 Å).

$^1$H NMR spectra were acquired on a Bruker Avance 400 instrument at 400 MHz. Gel permeation chromatography (GPC) was performed in tetrahydrofuran (THF) using a Waters system equipped with four 5-micrometer Waters columns (300 mm×7.7 mm) connected in series with increasing pore size (100, 1000, 105, and 106 angstroms), a Waters 410 differential refractometer, and a 996 photodiode array detector. The system was calibrated using polystyrene standards. GPC analysis was also performed in N,N-dimethylformamide (DMF) spiked with 0.01 M LiBr using a Waters system equipped with two Agilent PolyPore columns (300 mm×7.5 mm) connected in series, a Waters 410 differential refractometer. The system was calibrated with poly(methyl methacrylate) standards.

Preparations of Cyclic Carbonates
Preparation of MTC-OH (MW 160.1).

MTC-OH

MTC-OH can be prepared by the method of R. C. Pratt, et al., Chemical Communications, 2008, 114-116.

Preparation of MTC-C6F5 (MW 326.2).

PFC

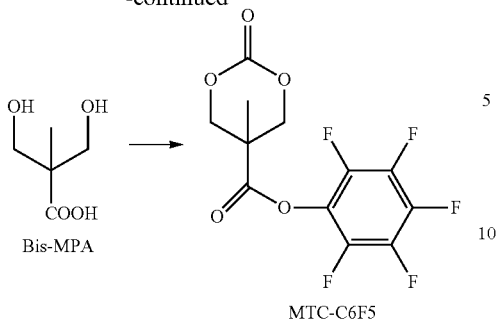

A 100 mL round bottom flask was charged with bis-MPA, (7), (5.00 g, 37 mmol, MW 134.1), bis-(pentafluorophenyl) carbonate (PFC, 31.00 g, 78 mmol, MW 394.1), and CsF (2.5 g, 16.4 mmol) rinsed with 70 mls of tetrahydrofuran (THF). Initially the reaction was heterogeneous, but after one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}$F NMR of pentafluorophenol and a single peak in the GCMS with a mass of 184. The filtrate was extracted with aqueous sodium bicarbonate and dried with MgSO$_4$. The solvent was evaporated in vacuo and the product was recrystallized (ethyl acetate/hexane mixture) to give MTC-C6F5 as a white crystalline powder. The GCMS had a single peak with mass of 326 g/mol. The calculated molecular weight for C$_{12}$H$_7$F$_5$O$_5$ was consistent with the assigned structure. $^1$H-NMR (400 MHz in CDCl$_3$): delta 4.85 (d, J=10.8 Hz, 2H, CH$_a$H$_b$), 4.85 (d, J=10.8 Hz, 2H, CH$_a$H$_b$), 1.55 (s, 3H, CCH$_3$).

Example 1. Synthesis of Protected Mannose-Functionalized Cyclic Carbonate (MTC-IPMAN)

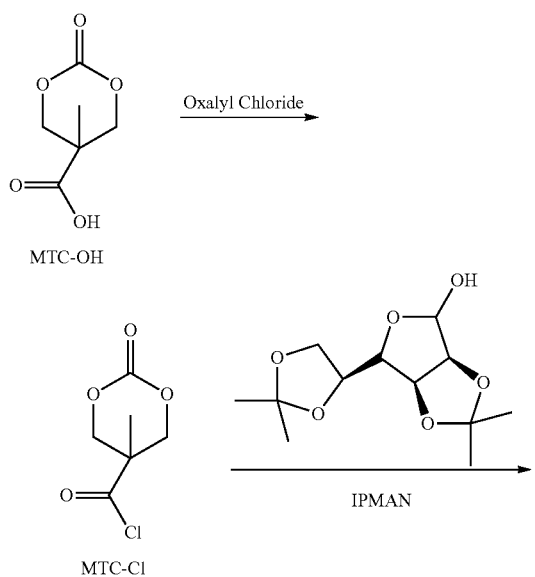

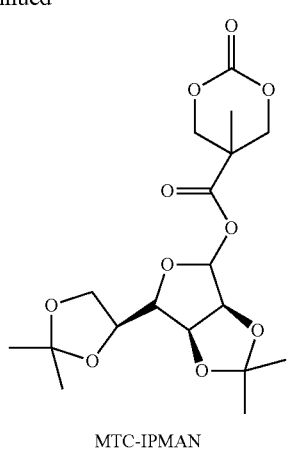

MTC-IPMAN

5-Methyl-5-carboxyl-1,3-dioxan-2-one (MTC-OH) and the monomer MTC-ipman were prepared as follows. A dry tetrahydrofuran (THF) solution of oxalyl chloride (2.48 mL, 19.0 mmol, 50 mL) was added dropwise into a dry THF solution of 5-methyl-5-carboxyl-1,3-dioxan-2-one (MTC-OH) (2.75 g, 17.2 mmol, 50 mL). A catalytic amount (3 drops) of anhydrous dimethylformamide (DMF) was then added over 30 min under nitrogen atmosphere, and the reaction mixture was stirred for 1 hour with nitrogen bubbled through to remove volatiles. After the solvent was evaporated under vacuum, the solid residue (intermediate product MTC-Cl) was dissolved in 50 mL of dry chloroform, and a mixture of 2,3;5,6-di-O-isopropylidene-D-mannofuranose (IPMAN, 4.13 g, 15.8 mmol) and triethylamine (2.8 mL, 20.6 mmol) in 50 mL of dry chloroform was stepwise dropped into the solution over 30 minutes at room temperature. The reaction mixture was heated to 40° C. and stirred for 48 hours. The resulting solution was cooled to room temperature, concentrated, treated with THF (100 mL) to precipitate triethylamine salt, and filtered. After evaporating the filtrate, the crude product was passed through a silica gel column by gradient eluting of ethyl acetate and hexane (20/80 to 50/50) to provide the product as sticky colorless oil that slowly solidified to a white solid (5.85 g, 85%). $^1$H-NMR (400 MHz, CDCl$_3$, 22° C.): δ 6.22 (s, 1H, H-a), 4.89 (dd, 1H, H-b), 4.72 (d, 2H, H-c), 4.66 (m, 2H, H-c), 4.41 (m, 1H, H-d), 4.22 (m, 2H, H-e), 4.11 (dd, 2H, H-e), 4.03 (m, 2H, Hf+H-g), 1.50-1.33 (5 s, 15H, H-h+H-i).

Preparation of MTC-Catechol.

-continued

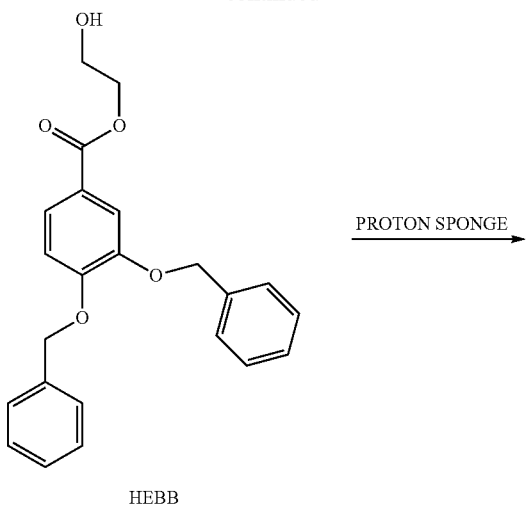

HEBB

PROTON SPONGE →

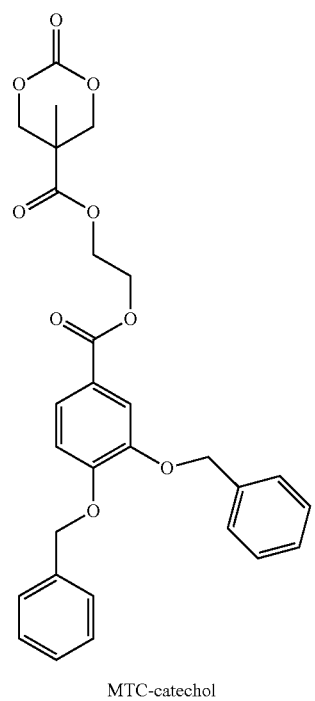

MTC-catechol

2-Hydroxyethyl-3,4-bis(benzyloxy)benzoate (HEBB, 2.81 g, 7.42 mmol), MTC-C6F5 (2.54 g, 7.79 mmol) and PROTON SPONGE (1.59 g, 7.42 mmol) were dissolved in THF (10 mL) and stirred overnight at room temperature. Once the reaction was completed, a mixture of diethyl ether and hexanes was added, and the solution was left for several hours at −40° C. White crystals were obtained and washed with diethyl ether and hexanes. Yield: 2.0 g (71%). $^1$H NMR (400 MHz, CDCl$_3$, 22° C.): delta 7.64 (d, 2H, H of benzoate), 7.43 (m, 10H, —OCH$_2$PhH), 6.97 (d, 1H, H of benzoate), 5.24 (d, 4H, —OCH$_2$PhH), 4.68 (d, 2H, —CH2OCOO—), 4.54 (s, 4H, —COOCH$_2$CH$_2$O—), 4.19 (d, 2H, —CH2OCOO—), 1.32 (s, 3H, —CH$_3$).

Preparation of BPEI25 and BPEI1.8 Conjugates

In the following examples, the structures of BPEI25 and BPEI1.8 are represented by following notation:

$$\left[ \left( \begin{array}{c} H_2C \!-\!\! * \\ | \\ H_2C \!-\!\! * \end{array} \right)_j \left( \begin{array}{c} *\!\! \diagdown \\ *\!\! \diagup \end{array} NH \right)_q \left( \begin{array}{c} *\!\! \diagdown \\ *\!\! - \\ *\!\! \diagup \end{array} N \right)_s (*\!\!-\!\!NH_2)_t \right]$$

| BPEI25 | BPEI1.8 |
|---|---|
| Mw = 25 kDa | Mw = 2 kDa |
| Mn = 10 kDa | Mn = 1.8 kDa |
| q = 116 | q = 20 |
| s = 58 | s = 10 |
| t = 58 | t = 10 |
| j = 233 | j = 40. |

The subscript q represents the number of secondary amine groups (pKa 8.6). For BPEI25, q=116. The subscript s represents the number of tertiary amine groups (pKa 7.5). For BPEI25, s=58. The subscript t represents the number of primary amine groups (pKa 9.6). For BPEI25, t=58. The subscript j represents the number of ethylene groups. For BPEI25, j=233. Thus, BPEI25 is a hyperbranched polymer having an average of 233 ethylene groups, 58 primary amine groups, 116 secondary amine groups, 58 tertiary amine groups per mole. For the reactions below, 1 mole=10000 g=Mn.

BPEI1.8 has an average of 40 ethylene groups, 10 primary amine groups, 20 secondary amine groups, and 10 tertiary amine groups per mole. For the reactions below, 1 mole=1800 g=Mn.

It should be understood that each starred bond of a given nitrogen of the right bracket is linked to a different ethylene group of the left bracket, and each starred bond of a given ethylene group on the left bracket is linked to a different nitrogen on the right bracket. Thus, the BPEI backbone comprises alternating amine nitrogens and ethylene groups (i.e., adjacent ethylenimine units are linked in head-to-tail arrangement). The tertiary, secondary and primary amine groups are randomly distributed in BPEI, indicated by the vertical stacking of the amine groups on the right square bracket. BPEI can contain numerous branches that intersect at the tertiary amine sites. Depending on the method of formation of the BPEI, peripheral end groups (dangling end groups) can be a primary amine group, alkyl group, or another $C_1$-$C_{10}$ moiety. In the examples below, branches terminate at a peripheral end with a primary amine group. In the above notation, all peripheral end groups (dangling end groups) are primary amine groups.

A selected number of the primary and/or secondary amine groups on BPEI25 were modified with a mannose-substituted cyclic carbonate MTC-IPMAN. The ring-opening reaction generates a side chain containing a carbamate side chain containing a protected mannose functionality. Deprotection of the protected mannose groups yields a side chain bearing a mannose group. An additional benefit of this modification is a significant reduction in toxicity of the modified BPEI25 compared to the non-modified BPEI25.

Examples 2 to 7

Preparation of B1-B6 by modifying BPEI25 (Mn 10,000=1 mole) with MTC-IPMAN. The modification of BPEI25 is illustrated below for the preparation of B3 (Example 4). For B3, MTC-IPMAN was used in excess of the primary amine groups of BPEI25. Under these conditions, MTC-IPMAN does not undergo ring opening polymerization. About 100% of the BPEI25 primary amine groups and about 6% of the BPEI25 secondary amine sites are modified with one ring opened molecule of MTC-IPMAN. Subsequent acid catalyzed hydrolysis of the isopropylidene ketal protecting groups results in a modified BPEI25 containing 65 mannose units linked to the PEI backbone by respective carbamate linking groups.

BPEI25
Mw = 25 kDa
Mn = 10 kDa
q = 116
s = 58
t = 58
j = 233

+

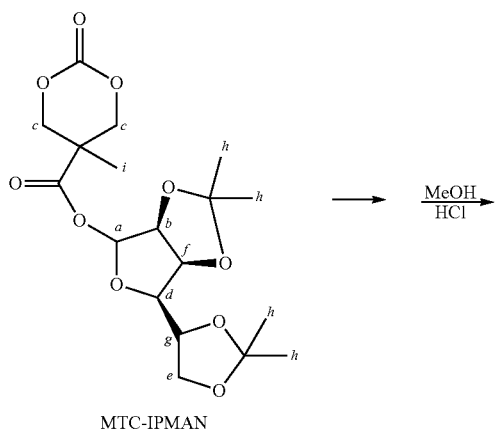

MTC-IPMAN

→ MeOH / HCl

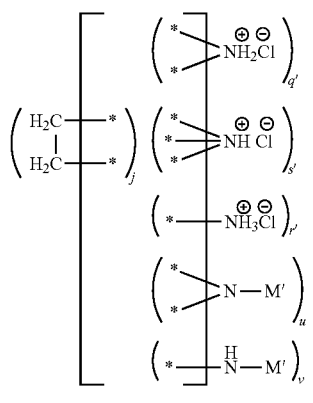

B3 j = 233
s' = 58
u = 7
v = 58
u + v = 65
q' = 109
t' = 0

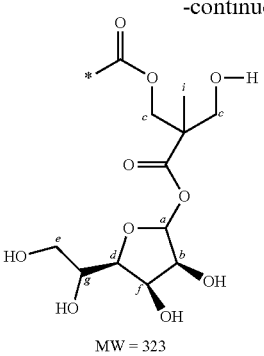

$MW = 323$

In a glove box, MTC-IPMAN (0.302 g, 0.75 mmol, MW=402.15 g) was added to the solution of BPEI25 (0.1 g, 0.01 mmol based on 1 mole=10,000 g=Mn) in 2 mL of dichloromethane (DCM). The BPEI25:MTC-IPMAN feed mass ratio was 1:3, the molar ratio was 1:75. The reaction solution was stirred for 1 hour. 10 mL of methanol and 10 mL of 1 M HCl (aq.) were added. The resulting reaction mixture was heated at reflux for 2 hours before cooling to room temperature. Finally, the above mixture was purified by ultrafiltration in a Vivaspin 20 concentrator (MWCO=5000, Sartorius AG, Goettingen, Germany), washed 3 times with de-ionized (DI) water, and freeze-dried (0.19 g, 48%). $^1$H-NMR (400 MHz, D$_2$O, 22° C.): delta 4.11 (s, 130H, H-d and H-e), 2.56-3.70 (br, m, 1190H, H-e, H-f, H-g and H of BPEI), 1.10 (s, 195H, H-i).

In the above structure of B3, s' represents the number of protonated tertiary amine groups, q' represents the number of remaining secondary amine groups in the form of a protonated salt, t' represents the number of remaining primary amine end groups in the form of a protonated salt, u represents the number of modified secondary amine groups bearing the moiety M', and v represents the number of modified primary amine groups bearing the moiety M'. For B3, q'=109, s'=58, t'=0, u=7, v=58, and u+v=65.

The amine modification level of B3 was monitored and quantified using $^1$H-NMR (FIG. 1). For example, relative integral intensities of a broad peak (2.56-3.70 ppm), which are attributed to the protons of BPEI25 methylene and H-e, H-f and H-g of mannose moieties, and MTC methyl signals (1.10 ppm) in the $^1$H-NMR spectrum were compared in order to determine the number of mannose groups. More of the secondary amine sites were modified in B4-B6, where the number of mannose groups introduced was 86, 104 and 143, respectively.

B1 (Example 2) was prepared by reaction of BPEI25 (0.2 g, 0.02 mmol) with MTC-IPMAN (201 mg, 0.5 mmol) in dichloromethane following the above general procedure for B3 (Example 4). A total of 28 mannose groups were introduced (BPEI25:MTC-IPMAN molar ratio: 1:28). For B1, q'=116, s'=58, t'=30, u=0, v=28, and u+v=28.

B2 (Example 3) was prepared by reaction of BPEI25 (0.12 g, 0.012 mmol) with MTC-IPMAN (280 mg, 0.7 mmol) in dichloromethane following the above general procedure for B3 (Example 4). A total of 51 mannose groups were introduced (BPEI25:MTC-IPMAN molar ratio: 1:51). For B2, q'=116, s'=58, t'=7, u=0, v=51, and u+v=51.

The ring opening reaction is increasingly affected by steric hindrance with an increased degree of modification, requiring more forcing conditions to obtain the desired level of modified amine groups at the higher modification levels.

B4 (Example 5) was prepared by reaction of BPEI25 (58 mg, 0.0058 mmol) with MTC-IPMAN (280 mg, 0.7 mmol) in dichloromethane following the above general procedure for B3 (Example 4) except the reaction was stirred 2.5 hours at ambient temperature. A total of 86 mannose groups were introduced (BPEI25:MTC-IPMAN molar ratio: 1:86). For B4, $q'=88$, $s'=58$, $t'=0$, $u=28$, $v=58$, and $u+v=86$.

B5 (Example 6) was prepared by reaction of BPEI25 (70 mg, 0.007 mmol) with MTC-IPMAN (338 mg, 0.84 mmol) in dichloromethane following the above general procedure for B3 (Example 4), except the reaction was stirred 3 hours at 40° C. A total of 104 mannose groups were introduced (BPEI25:MTC-IPMAN molar ratio: 1:104). For B5, $q'=70$, $s'=58$, $t'=0$, $u=46$, $v=58$, and $u+v=104$.

B6 (Example 7) was prepared by reaction of BPEI25 BPEI25 (50 mg, 0.005 mmol) with MTC-IPMAN (362 mg, 0.9 mmol) in dichloromethane following the above general procedure for B3 (Example 4), except the reaction was stirred 3 hours at 40° C. A total of 143 mannose groups were introduced (BPEI25:MTC-IPMAN molar ratio: 1:143). For B6, $q'=31$, $s'=58$, $t'=0$, $u=85$, $v=58$, and $u+v=143$.

Examples 8 and 9

Preparation of B7 and B8 by modifying BPEI25 with trimethylene carbonate (TMC). The preparation of B7, in which 25 TMC units were introduced, is shown in the following reaction diagram.

B7 (Example 8) was prepared by reaction of BPEI25 (0.25 g, 0.025 mmol) with TMC (64 mg, 0.63 mmol) in dichloromethane following the above general procedure for B3 (Example 4). A total of 25 TMC groups were introduced. For B7, $q'=116$, $s'=58$, $t'=33$, $u=0$, $v=25$, and $u+v=25$.

B8 (Example 9) was prepared by reaction of BPEI25 (0.25 g, 0.025 mmol) with TMC (191 mg, 1.87 mmol) in dichloromethane following the general procedure for B3 (Example 4). A total of 75 TMC groups were introduced. For B8, $q'=99$, $s'=58$, $t'=33$, $u=17$, $v=58$, and $u+v=75$.

Examples 10 to 12

Preparation of B9 to B11 by modifying of BPEI25 with MTC-catechol. The preparation of B9 (Example 10) is representative, wherein 5 MTC-catechol groups are introduced. The hydrogen reduction of the protected catechol groups can leave 0 or more protected catechol groups in the final product.

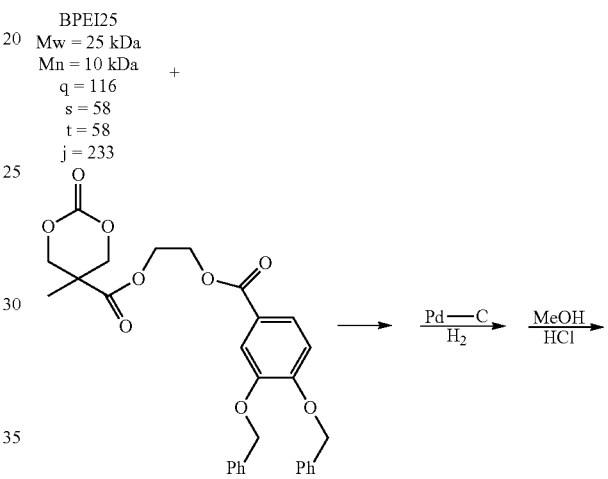

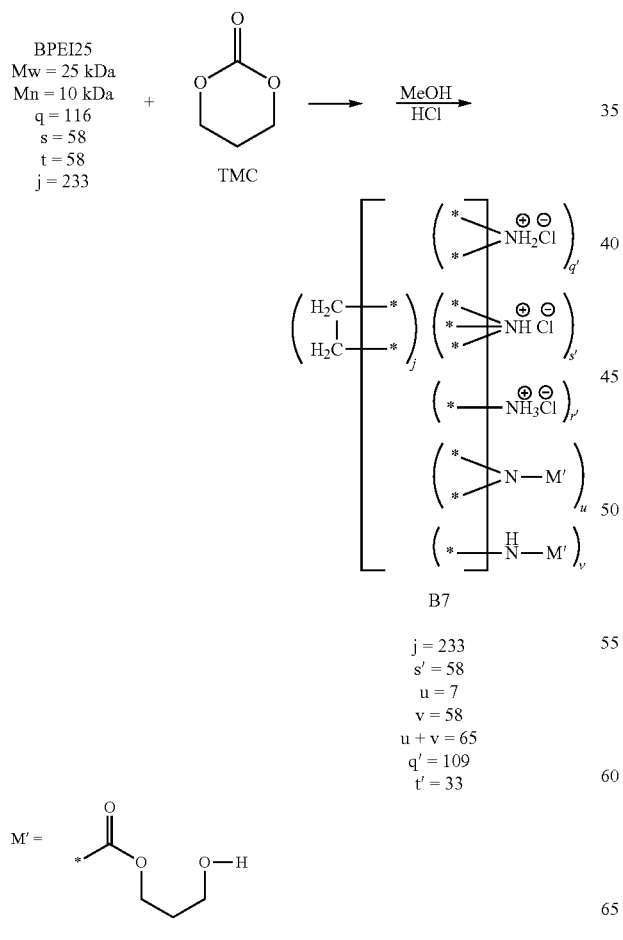

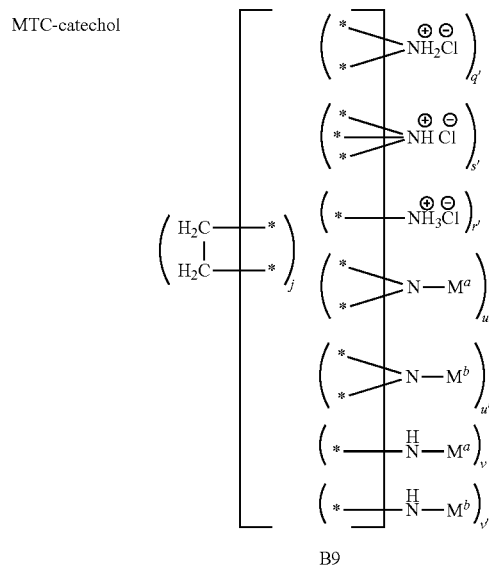

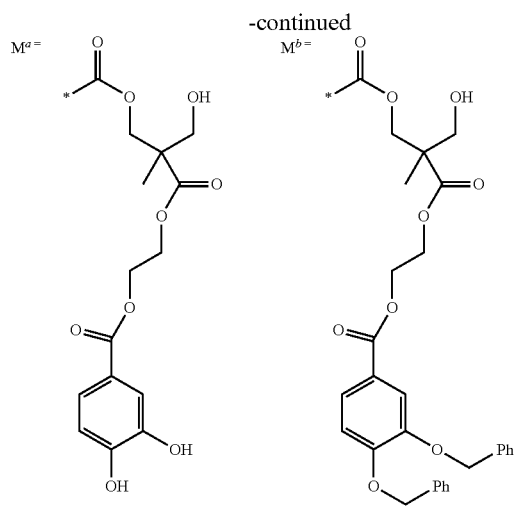

ration of B12 (Example 13) is shown in the reaction diagram below, for which 4 mannose groups were introduced.

BPEI1.8
Mw = 2000
Mn = 1800
q = 20
s = 10
t = 10
j = 40

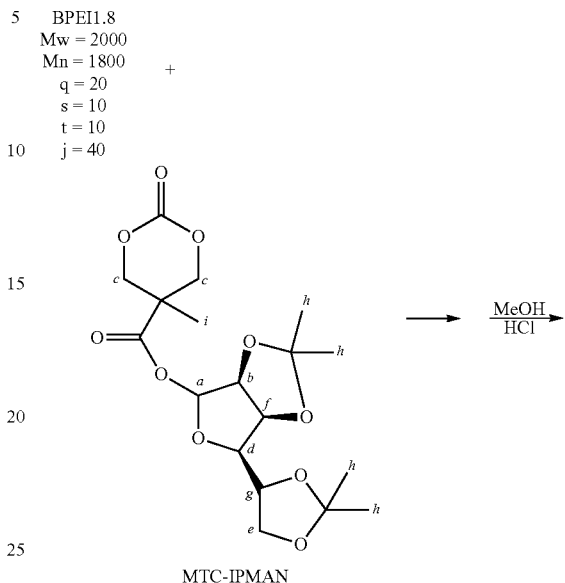

BPEI25 (0.3 g, 0.03 mmol) was treated with MTC-catechol (62.4 mg, 0.12 mmol) in dichloromethane according to Example 2. A total of 5 protected catechol groups were introduced. The resulting product was dried in vacuum. A mixture of the protected conjugate (362 mg), MeOH (7.5 mL), THF (7.5 mL), and Pd—C (10% w/w, 0.2 g) was swirled under $H_2$ (7 atm) overnight. After evacuation of the hydrogen atmosphere, the mixture was filtered by syringe and the filtrate was concentrated to dryness. Then, MeOH (10 mL) and 1 M HCl (10 mL) were added sequentially and the reaction solution was stirred for 2 to 3 hours. After acidification, the solution was purified by centrifugal filtration (MWCO=3,000) and washed twice with deionized (DI) water for three times. Finally, the concentrated solution in the centrifuge tube was freeze-dried, yielding the deprotected and acidified BPEI-Catechol conjugate B9 (0.43 g, 53%). $^1$H-NMR (400 MHz, $D_2O$, 22° C.): $^1$H-NMR (400 MHz, $D_2O$, 22° C.): delta 6.70-7.60 (br, m, 15H, PhH), 3.90-4.40 (br, m, 10H, —$CH_2OCOO$), 2.50-3.70 (br, m, 950H, H of —$CH_2CH_2OC(O)Ph$ and BPEI25), 1.03 (m, 15H, —$CH_3$).

For B9, q'=116, s'=58, t'=53, u=0, u'=0, v 0, v'≥=0, and u+u'+v+v'=5.

B10 (Example 11) was prepared by reaction of BPEI25 (0.3 g, 0.03 mmol) with MTC-catechol (124.8 mg, 0.24 mmol) in dichloromethane following the general procedure of Example 10. A total of 12 catechol groups were introduced. For B10, q'=116, s'=58, t'=46, u=0, u'=0, v>0, v'≥=0, and u+u'+v+v'=12.

Figure 2A:
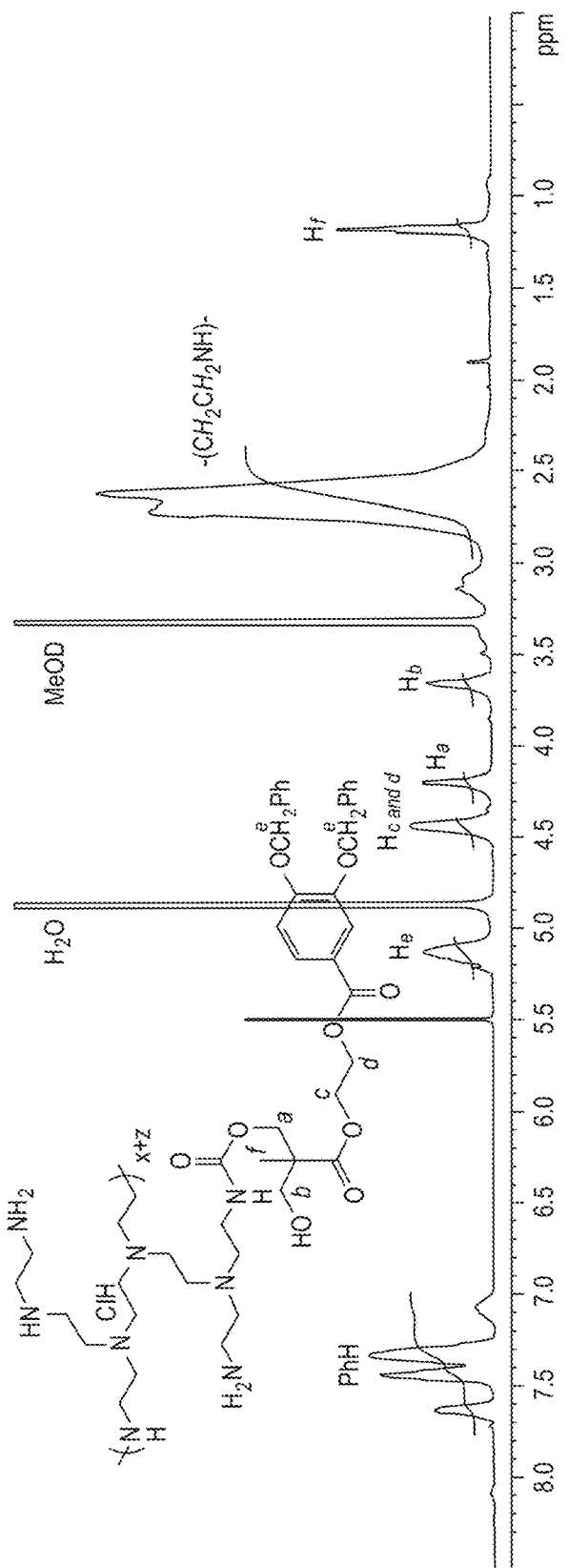
FIG. 2A is a $^1$H NMR spectrum of the precursor to cationic polyamine B11 taken in MeOD before hydrogenolysis. The branched polyethylenimine structure is a simplified rendition for assigning NMR peaks.
Figure 2B:
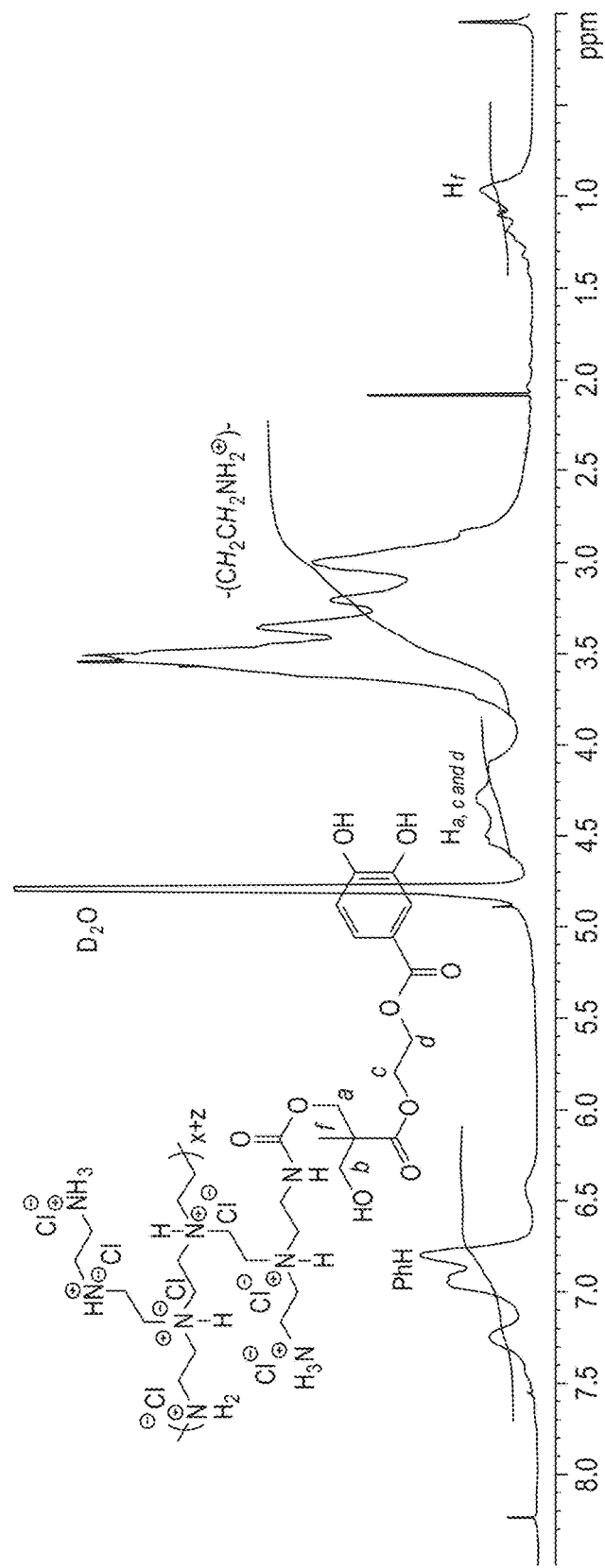
FIG. 2B is a $^1$H NMR spectra taken in D$_2$O of cationic polyamine B11 after hydrogenolysis and acidification. The branched polyethylenimine structure is a simplified rendition for assigning NMR peaks.

B11 (Example 12) was prepared by reaction of BPEI25 (0.2 g, 0.02 mmol) with MTC-catechol (167 mg, 0.32 mmol) in dichloromethane following the general procedure of Example 10. A total of 20 catechol groups were introduced. FIG. 2A is a $^1$H NMR spectrum taken in MeOD before hydrogenolysis. FIG. 2B is a $^1$H NMR spectrum taken in $D_2O$ of B11 after hydrogenolysis and acidification. For B11, q'=116, s'=58, t'=38, u=0, u'=0, v>0, v'≥=0, and u+u'+v+v'=20.

Preparation of BPEI1.8 Conjugates

BPE1.8 has Mw 2000 and Mn 1800. BPEI1.8 has q=20 secondary amine groups, s=10 tertiary amine groups, t=10 primary amine groups, and j=40 ethylene groups. For the calculations below, 1 mole BPEI1.8=1800 g.

Examples 13 to 15

Preparation of B12 to B14, respectively, by modifying BPEI1.8 (Mn 1800=1 mole) with MTC-IPMAN. The preparation of B12 (Example 13) is shown in the reaction diagram below, for which 4 mannose groups were introduced.

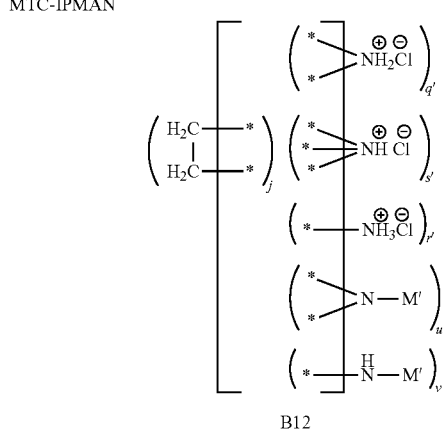

B12 j = 40
s' = 10
u = 0
v = 4
u + v = 4
q' = 20
t' = 6

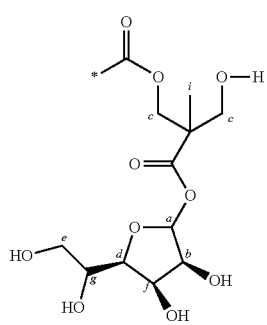

B12 (Example 13) was prepared by reaction of BPEI1.8 (0.198 g, 0.11 mmol) with MTC-IPMAN (199 mg, 0.495 mmol) in dichloromethane following the general procedure used for B3 (Example 4). A total of 4 mannose groups were introduced.

In the above structure for B12, s' represents the number of protonated tertiary amine groups, q' represents the number of remaining secondary amine groups in the form of a protonated salt, t' represents the number of remaining primary amine end groups in the form of a protonated salt, u represents the number of modified secondary amine groups bearing the moiety M', and v represents the number of modified primary amine groups bearing the moiety M'. For B12, q'=20, s'=10, t'=6, u=0, and v=4, and u+v=4.

B13 (Example 14) was prepared by reaction of BPEI1.8 (0.108 g, 0.06 mmol) with MTC-IPMAN (326 mg, 0.81 mmol) in dichloromethane following the general procedure used for B3 (Example 4). A total of 9 mannose groups were introduced. For B13, q'=20, s'=10, t'=1, u=0, and v=9, and u+v=9.

B14 (Example 15) was prepared by reaction of BPEI1.8 (0.072 g, 0.04 mmol) with MTC-IPMAN (348 mg, 0.864 mmol) in dichloromethane following the general procedure used for B3 (Example 4). A total of 17 mannose groups were introduced. For B13, q'=13, s'=10, t'=0, u=7, and v=10, and u+v=17.

Preparation of LPEI25 Conjugates

LPEI25 is a linear polyethyleneimine having Mw=25000, Mn=10950, PDI 1.16; 0 primary amine end groups, 247 secondary amine groups (x), and 8 acylated secondary amine groups (y), represented by the notation below.

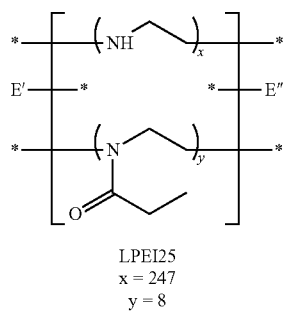

Vertical stacking of the repeat units within the square brackets represents a random distribution of the repeat units. End group E is methyl and end group E' is OH. E' and E" are not limited to these end groups. For the following examples, 1 mole LPEI25=10950 grams.

Examples 16 to 18

Preparation of mannose modified LPEI25 polymers L1 to L3 (polymers t to v), respectively. The preparation of L1 is representative, where 8 mannose groups were introduced.

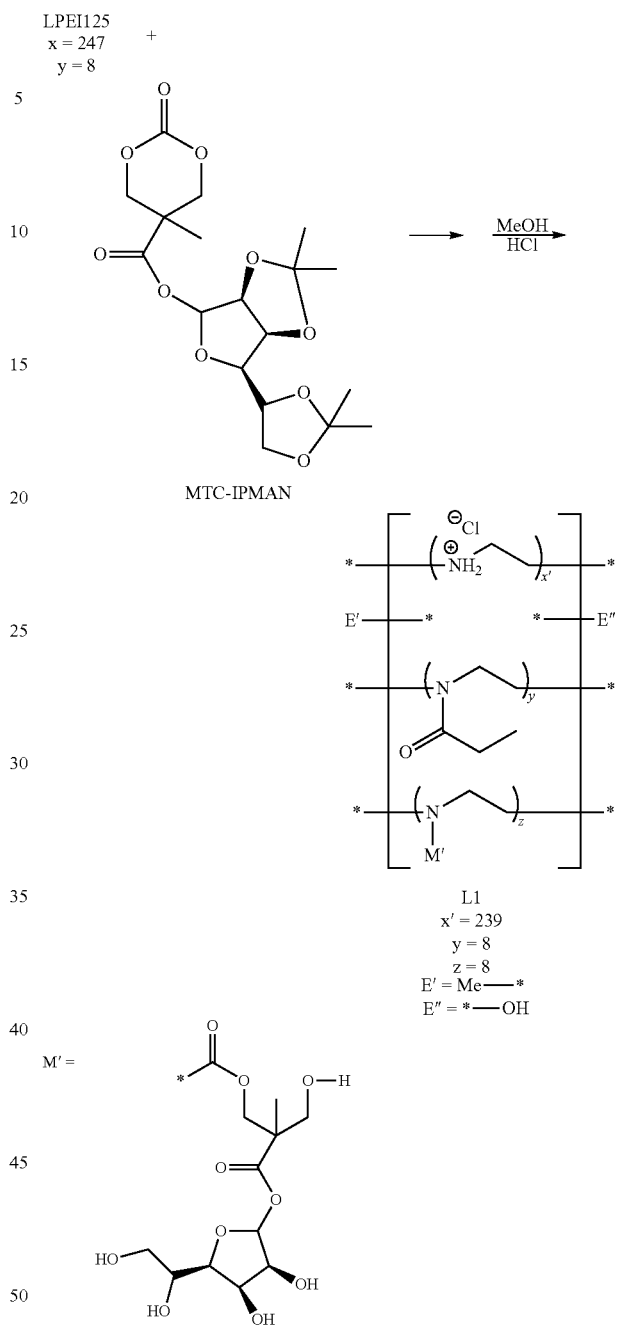

LPEI25 (0.35 g, 0.032 mmol) was heated for 3 hours in a flask at 65° C. in vacuum. When the flask cooled to room temperature, dioxane (30 mL) was added to the flask. Then, the flask was charged with condenser and heated to 85° C. After all the LPEI25 was dissolved in dioxane and a homogeneous solution was obtained, a solution of MTC-IPMAN (50 mg, 0.12 mmol) in 10 mL of dioxane was added. The reaction mixture was stirred overnight at 85° C. in contact with air. The flask cooled to room temperature, and the solvent was removed by rotary evaporation. The resulting product was dried in vacuum. For L1, x'=239, y=8, and z=8.

The above conjugate was dissolved in MeOH (10 mL) and 1 M HCl (10 mL). The solution was heated at reflux for 2 hours and cooled to room temperature. The resulting solution was purified by centrifugal filtration (MWCO=2,000) and washed three times with deionized (DI) water. Finally, the concentrated solution in the centrifuge tube was freeze-dried, yielding the acidified LPEI-Man conjugate L1 (0.47 g, 80%). $^1$H-NMR (400 MHz, $D_2O$, 22° C.): delta 3.00-4.00 (m, 1059H, H of LPEI and mannose), 2.37 (m, 16H, $CH_3CH_2CONH$—), 1.06 (m, 24H, $CH_3CH_2CONH$—), 0.96 (m, 24H, —$CH_3$).

L2 was prepared by reaction of LPEI25 (0.3 g, 0.027 mmol) with MTC-IPMAN (100 mg, 0.25 mmol) following the general procedure of Example 16. A total of 15 mannose groups were introduced. For L2, x'=232, y=8, and z=15.

L3 was prepared by reaction of LPEI25 (0.2 g, 0.018 mmol) with MTC-IPMAN (200 mg, 0.5 mmol) following the general procedure of Example 16. A total of 26 mannose groups were introduced. For L3, x'=221, y=8, and z=26.

Table 2 summarizes the preparations of the modified BPEI25 and LPEI25 polymers of Examples 2-18.

TABLE 2

| Example | Name | PEI | Cyclic Carbonate | # Amine Groups Modified | % of Amine Groups Modified | Mn$^a$ |
|---|---|---|---|---|---|---|
| 2 | B1 | BPEI25 | MTC-IPMAN | 28 | 12.0 | 19,016 |
| 3 | B2 | BPEI25 | MTC-IPMAN | 51 | 21.9 | 26,422 |
| 4 | B3 | BPEI25 | MTC-IPMAN | 65 | 27.9 | 30,930 |
| 5 | B4 | BPEI25 | MTC-IPMAN | 86 | 36.9 | 37,692 |
| 6 | B5 | BPEI25 | MTC-IPMAN | 104 | 44.6 | 43,488 |
| 7 | B6 | BPEI25 | MTC-IPMAN | 143 | 61.4 | 56,046 |
| 8 | B7 | BPEI25 | TMC | 25 | 10.7 | 12,550 |
| 9 | B8 | BPEI25 | TMC | 75 | 32.2 | 17,650 |
| 10 | B9 | BPEI25 | MTC-Catechol | 5 | 2.1 | 11,700 |
| 11 | B10 | BPEI25 | MTC-Catechol | 12 | 5.2 | 14,080 |
| 12 | B11 | BPEI25 | MTC-Catechol | 20 | 8.6 | 20,880 |
| 13 | B12 | BPEI25 | MTC-IPMAN | 4 | 1.7 | 3,088 |
| 14 | B13 | BPEI25 | MTC-IPMAN | 9 | 3.9 | 4,698 |
| 15 | B14 | BPEI25 | MTC-IPMAN | 17 | 7.3 | 7,274 |
| 16 | L1 | LPEI25 | MTC-IPMAN | 8 | 20.0 | 13,526 |
| 17 | L2 | LPEI25 | MTC-IPMAN | 15 | 37.5 | 15,780 |
| 18 | L3 | LPEI25 | MTC-IPMAN | 26 | 65.0 | 19,322 |

$^a$Obtained from $^1$H NMR.

Titration Experiments

The number of mannose modified amine groups of B1 to B6 was 28, 51, 65, 86, 104, and 143, respectively. Acid-base titration experiments were performed with polymers B1 to B6 to evaluate their relative pH neutralization capacity (buffering capacity).

A given polymer (0.1 mmol of all amines excluding those reacted with mannose-functionalized cyclic carbonate) was first dissolved in NaCl solution (7.5 mL, 150 mM). HCl solution (22.5 mL, 0.01 N) was added to bring the pH down to 2 and the solution was then titrated against 0.01 N NaOH to pH 10 using an auto titrator (Spectralab Instruments). Unmodified BPEI25 (Mn 10 kDa) was used as a control. The buffering capacity is defined as the percentage of amine groups of the polymer that are protonated over the pH of 5.0 to 7.4, and is calculated by the following equation: buffering capacity (%)=100×($V_{NaOH}$×0.01×40)/W, where $V_{NaOH}$ is the volume of NaOH (0.01 N, MW 40), which is required to increase the pH from 5.0 to 7.4, and W is the weight (in milligrams) of the polymers.

Table 3 lists the buffering capacities of BPEI25 and B1 to B6.

TABLE 3

| Example | Name | Starting PEI | Cyclic Carbonate | # Modified Amine Groups | Buffering capacity (%) |
|---|---|---|---|---|---|
| Control | BPEI25 | | | 0 | 24.2 |
| 2 | B1 | BPEI25 | MTC-IPMAN | 28 | 16.3 |
| 3 | B2 | BPEI25 | MTC-IPMAN | 51 | 10.9 |
| 4 | B3 | BPEI25 | MTC-IPMAN | 65 | 8.8 |
| 5 | B4 | BPEI25 | MTC-IPMAN | 86 | 7.5 |
| 6 | B5 | BPEI25 | MTC-IPMAN | 104 | 7.2 |
| 7 | B6 | BPEI25 | MTC-IPMAN | 143 | 5.7 |

As indicated above, the neutralization capacity of the endosomal pH from 5.0 to 7.4 decreased with increasing mannose content at the same weight concentration of polymers due to a reduced number of secondary amines and/or increased molecular weight, which lowers the tertiary amine content per unit mass of the polymer.

Anti-Viral Activity

Cells

LLC-MK2 cells (monkey kidney cell) were cultured in Eagle's minimum essential medium (EMEM, Sigma-Aldrich, St. Louis, Mo.) supplemented with 10% fetal bovine serum (FBS, Invitrogen, Carlsbad, Calif.), 100 units/mL penicillin and 100 micrograms/mL streptomycin at 37° C. in 5% $CO_2$.

Aedes albopictus C6/36 cells were maintained in Roswell Park Memorial Institute (RPMI) medium RPMI-1640 (Invitrogen, Carlsbad, Calif.) with HEPES (4-(2-hydroxyethyl)-1-piperazineethanesulfonic acid, 25 mM) supplemented with 10% FBS (fetal bovine serum), 100 U/mL penicillin and 100 micrograms/mL streptomycin, and incubated at 28° C. in 5% $CO_2$.

A549 replicon cells (containing DENV-2 NS genes), Vero cell line (monkey kidney epithelial), MDCK cell line (dog kidney epithelial), and RD cell line (human muscle spindle cell, rhabdomyosarcoma) were grown in Dulbecco's modified Eagle's medium (DMEM) supplemented with 10% FBS, 100 U/mL penicillin and 100 micrograms/mL streptomycin at 37° C. in 5% $CO_2$.

Viruses

Clinical samples of DENV-1 and DENV-4 and laboratory-adapted New Guinea C (NGC) strain of DENV-2 were kindly provided by Dr. Justin JH Chu (National University of Singapore, Singapore). DENV-3 strain EDEN8630K1 was isolated by the method of Low, et al., "Early Dengue Infection and Outcome Study (EDEN)—Study Design and Preliminary Findings", Annals Academy of Medicine Singapore 2006, 35, pages 783-789. The viruses were propagated in various cell lines as described in further below (Table 5). The supernatant from infected cells was centrifuged to remove cell debris, then aliquoted and stored at −80° C.

Anti-Viral Activity Based on Cytotoxicity Assay

Anti-dengue virus activity and cytotoxicity of polymers in LLC-MK2 cells were monitored by infecting the cells with DENV (i.e., DENV-1, DENV-2, DENV-3, or DENV-4). Infected (multiplicity of infection (MOI): 0.5) and non-infected cells were exposed to a range of concentrations of polymers (cell seeding density in 96-well plate: 2000 per well), and allowed to proliferate for 5 days. The number of viable cells was quantified by the 3-[4,5-dimethylthiazol-2-yl]-2,5-diphenyltetrazolium bromide (MTT) (Sigma-Aldrich, St. Louis, Mo.) assay to obtain EC50 (from infected cells) and CC50 (from non-infected cells).

Plaque Forming Assay

For EC50 determination of polymers, virus was added to LLC-MK2 cells in 6-well plates (cell seeding density: $3\times10^5$) with polymers at various concentrations at MOI of 100 pfu per well, and incubated at 4° C. for 90 min. The medium was then removed, and the cells washed with cold PBS (pH 7.4) before the cells were incubated with medium containing polymers at the corresponding concentrations at 37° C. At 5 days post-inoculation, the cells were fixed with 4% paraformaldehyde in PBS (pH 7.4) at room temperature for 20 minutes. Next, they were washed with water before the addition of 1 mL of 1% crystal violet at room temperature for 20 minutes. The plates were washed and dried, and the plaque forming units per milliliter (pfu/mL) were counted and calculated to obtain EC50.

Time of Addition Experiment

LLC-MK2 cells were seeded at $30\times10^4$ cells/well in 6-well plates. The cells were incubated with DENV-2 (100 pfu per well) at 4° C. for 90 min on a rocking platform. The cells were then washed 3 times with cold PBS and the plates were shifted to a 37° C. incubator and cultured. Culture medium containing 50 mg/L of B3 or 100 mg/L of heparin (MP Biomedicals, Solon, Ohio) was added to the cells at pre-determined time points (−1.5, 0, 1, 2, 3, 4 and 5 hours). After 5 days of incubation at 37° C., viral inhibition activity was studied by the plaque assay. Experiments were conducted in triplicates and mean percentage inhibition was calculated relative to the control, which was performed under the same conditions but without polymers.

Virus Binding Assay

DENV-2 was incubated with PBS (pH 7.4) or PBS containing B3 (50 mg/L) at 4° C. for one hour to allow the polymer to bind onto the virus. Unbound polymer molecules were then removed by filtration through a Vivaspin 500, 100 kDa molecular weight cut off (GE Healthcare, Buckinghamshire, UK) at 6000 grams for 15 minutes. The virus was subjected to the plaque assay as described above to determine titers.

Cell Binding Assay

LLC-MK2 cells were treated with B3 (50 mg/L) at 37° C. for 2 hours, 1 hour, 30 minutes, and 15 minutes, and washed with PBS. The cells were then infected with DENV-2 for 90 minutes, and inoculated at 37° C. for 5 days prior to plaque reduction assay. Control infection without the polymer was set to 100%. The data were expressed as the mean of three individual experiments±SD (standard deviation).

Cell Fusion Inhibition Assay

This assay was used to detect the inhibition of cell fusion by polymers at low pH. C6/36 cells were seeded with a cell density of $1.0\times10^6$ cells/well in 6-well plates one day prior to the assay. DENV-2 was inoculated at multiplicity of infection (MOI) 0.03 onto seeded C6/36 cells along with either 50 mg/L of B3, 100 mg/L of heparin, or medium, for 90 minutes at 4° C. The plates were then washed 3 times with PBS. Fresh medium containing the polymer/heparin was added to the plates, and the cells were incubated at 28° C. for 2 days. Thereafter, the medium was acidified to induce fusion by addition of 50 microliters of 0.5 M 2-(N-morpholin) ethanesulfonic acid (MES) (pH 5.0) (Sigma-Aldrich, St. Louis, Mo.), followed by incubation at 28° C. for 2 days. Fusion cells were then stained with Giemsa stain, modified solution (Sigma-Aldrich, St. Louis, Mo.) according to manufacturer's protocol. The stained plates were analyzed under a light microscope (CKX 31 microscope, Olympus, Tokyo, Japan). In another set of experiments, virus and cells were incubated for 90 minutes at 4° C. before the polymer or heparin was added.

Evaluation of Drug Resistance

Drug resistance was studied by passaging DENV-2 on LLC-MK2 cells in the presence of B3 at EC50. Cells ($3\times10^5$ per well) in 6-well plates were infected by DENV-2 (obtained from the previous passaging) at MOI of 0.1 in the presence of B3 at EC50. EC50 was determined for each passaging by the plague forming assay as described above.

In Vivo Toxicity Studies by Injection

Animal studies were performed according to protocols approved by the Singapore Biological Research Center (BRC)'s Institutional Animal Care and Use Committee and IBM's Animal Care and Use Committee. Female Balb/c mice (6-7 weeks, 18-22 g) were used in all experiments for studies of LD50 and toxicity to the major organs liver and kidney, and electrolyte balance in the blood.

LD50 (dose required to kill half the mouse population for a given test duration) was determined according to the Up-and-Down-Procedure described in OECD Guidelines for the Testing of Chemicals (OECD 425). Twenty mice were observed for 7 days and randomly marked to permit individual identification. B2 or B3 was dissolved in PBS (pH 7.4), and given to mice via tail vein injection at designed doses (i.e., 56.0, 175, 560 and 1750 mg/kg, 0.1 mL). Mortality was monitored for 14 days post-treatment, and LD50 was determined using the maximum likelihood method.

For the evaluation of the acute toxicity, two groups of 10 mice each received intravenous injection of B3 at 60 mg/kg in 100 microliters of sterilized saline. Ten mice were sacrificed at 48 hours and the remaining mice at 14 days to collect blood samples for analysis of ALT, AST, total bilirubin (TBIL), creatinine, urea nitrogen, sodium ion and potassium ion levels.

Results

Anti-Viral Activity and Selectivity of Modified PEI Polymers

Anti-viral activity of unmodified and modified PEI polymers (branched and linear) was investigated by a conventional MTT assay using LLC-MK2 cells infected with DENV-2 (dengue virus-2). Table 4 lists the EC50, CC50, and selectivity (CC50/EC50) obtained for BPEI25, BPEI1.8, B1-B14, and L1-L3 when the virus, cells and polymer were incubated at the same time.

TABLE 4

| Example | Name | PEI | Cyclic Carbonate | # Modified Amine Groups | EC50[a] (mg/L) | CC50[b] (mg/L) | Selectivity[c] (CC50/EC50) | Mn[d] |
|---|---|---|---|---|---|---|---|---|
| | Control | BPEI25 | | 0 | 0.01 | 5.44 | 544 | 10,000 |
| 2 | B1 | BPEI25 | MTC-IPMAN | 28 | 0.12 | 26.7 | 223 | 19,016 |
| 3 | B2 | BPEI25 | MTC-IPMAN | 51 | 0.4 | 697 | 1743 | 26,422 |
| 4 | B3 | BPEI25 | MTC-IPMAN | 65 | 0.3 | >1000 | >3333 | 30,930 |
| 5 | B4 | BPEI25 | MTC-IPMAN | 86 | 0.99 | >1000 | >1010 | 37,692 |

TABLE 4-continued

| Example | Name | PEI | Cyclic Carbonate | # Modified Amine Groups | EC50[a] (mg/L) | CC50[b] (mg/L) | Selectivity[c] (CC50/EC50) | Mn[d] |
|---|---|---|---|---|---|---|---|---|
| 6 | B5 | BPEI25 | MTC-IPMAN | 104 | 3.33 | >1000 | >300 | 43,488 |
| 7 | B6 | BPEI25 | MTC-IPMAN | 143 | 50.5 | >1000 | >19.8 | 56,046 |
| 8 | B7 | BPEI25 | TMC | 25 | 0.035 | 23.7 | 672 | 12,550 |
| 9 | B8 | BPEI25 | TMC | 75 | 0.31 | 25.9 | 83 | 17,650 |
| 10 | B9 | BPEI25 | MTC-Catechol | 5 | <0.0025 | 22.4 | >8965 | 11,700 |
| 11 | B10 | BPEI25 | MTC-Catechol | 12 | <0.0025 | 30 | >12006 | 14,080 |
| 12 | B11 | BPEI25 | MTC-Catechol | 20 | 0.0048 | 29.6 | 6171 | 20,880 |
|  | Control | BPEI1.8 |  |  | 0.5 | 122 | 244 | 1,800 |
| 13 | B12 | BPEI1.8 | MTC-IPMAN | 4 | 0.9 | 124.1 | 137 | 3,088 |
| 14 | B13 | BPEI1.8 | MTC-IPMAN | 9 | 7.9 | >1000 | >126 | 4,698 |
| 15 | B14 | BPEI1.8 | MTC-IPMAN | 17 | 110.1 | >1000 | >9 | 7,274 |
| 16 | L1 | LPEI25 | MTC-IPMAN | 8 | 1 | 122.3 | 122 | 13,526 |
| 17 | L2 | LPEI25 | MTC-IPMAN | 15 | 1.13 | 129.2 | 114 | 15,780 |
| 18 | L3 | LPEI25 | MTC-IPMAN | 26 | 1.4 | 523 | 37 | 19,322 |

[a]EC50 is the effective concentration at which the polymer protects 50% of the cells from viral infection. A low EC50 value is desirable.
[b]CC50 is the cytotoxic polymer concentration, at which 50% of the cells are killed. A high CC50 value is desirable.
[c]Selectivity is defined as CC50/EC50. A high selectivity is desirable.
[d]Obtained from $^1$H NMR.

The polymers inhibited DENV-2 replication in a dose-dependent manner with low EC50 values ranging from 0.01 to 50.5 mg/L. Non-modified BPEI25 (control sample) was the most potent polymer against dengue viral infection, having the lowest EC50 (0.01 mg/L). Non-modified BPEI25 was also the most cytotoxic, having a CC50 of 5.44 mg/L. Although mannose substitution decreased anti-viral capacity (i.e., increased EC50), this approach effectively mitigated PEI cytotoxicity (i.e., CC50 increased with increasing mannose modification). For example, CC50 increased from 26.7 to higher than 1000 mg/L when the number of mannose groups was increased from 28 to 65 (B1-B3, respectively). Among all polymers, B3 with 65 mannose residues had the highest selectivity index (SI, i.e. CC50/EC50) of 3333. A high selectivity is desirable.

Figure 3:
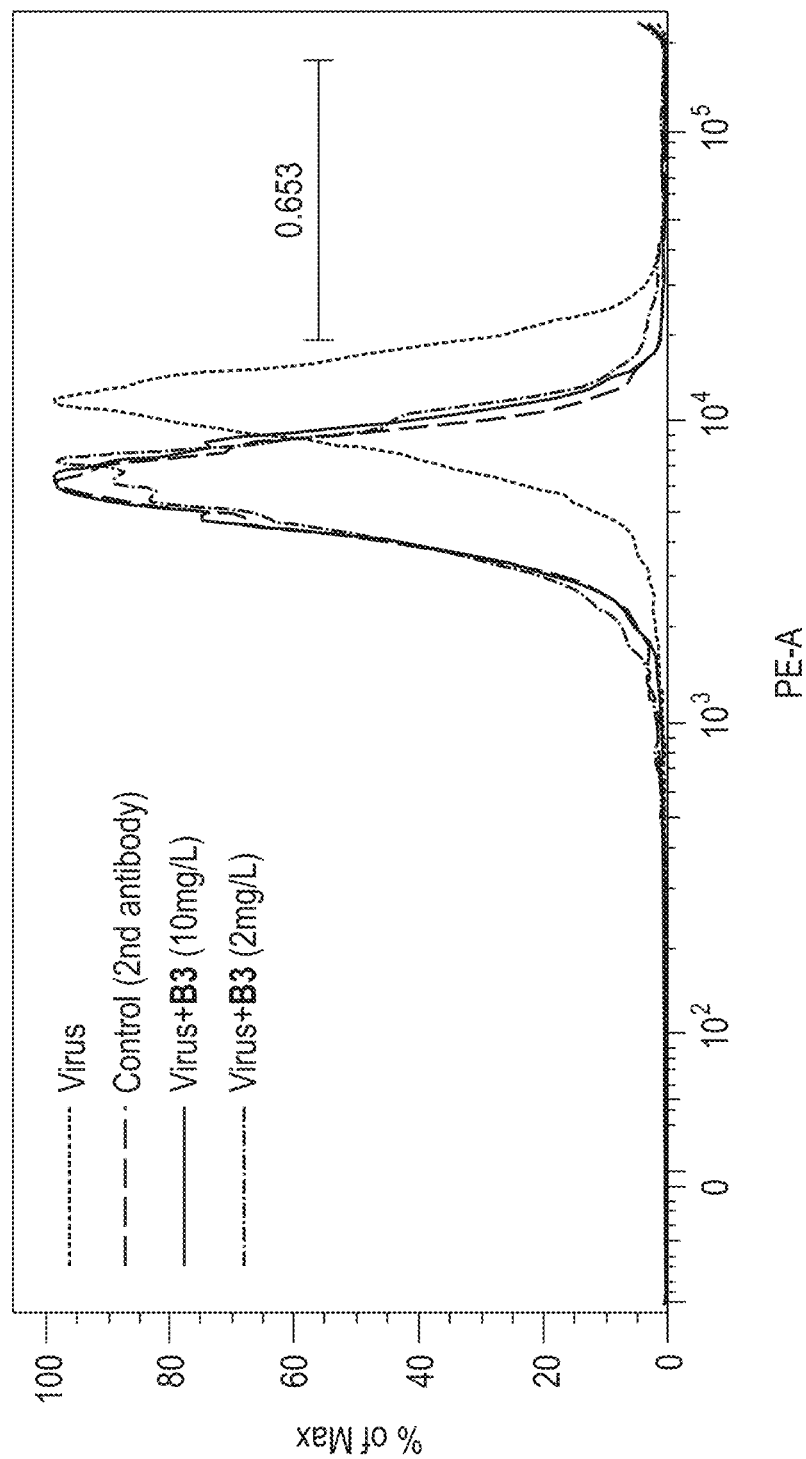
FIG. 3 is a graph showing the ability of cationic polyamine B3 to prevent infection of human primary peripheral blood mononuclear cells with the DENV-2 virus. After virus infection, the peak shifts to a higher PE-A (phycoerythrin (PE)-conjugated anti-mouse IgG). The peaks for the samples obtained from treatment with B3 at 2 or 10 mg/L do not shift, but rather almost overlap with the peak for the control sample without virus infection, indicating that B3 treatment effectively prevents human primary peripheral blood mononuclear cells from DENV-2 infection.
Figure 4:
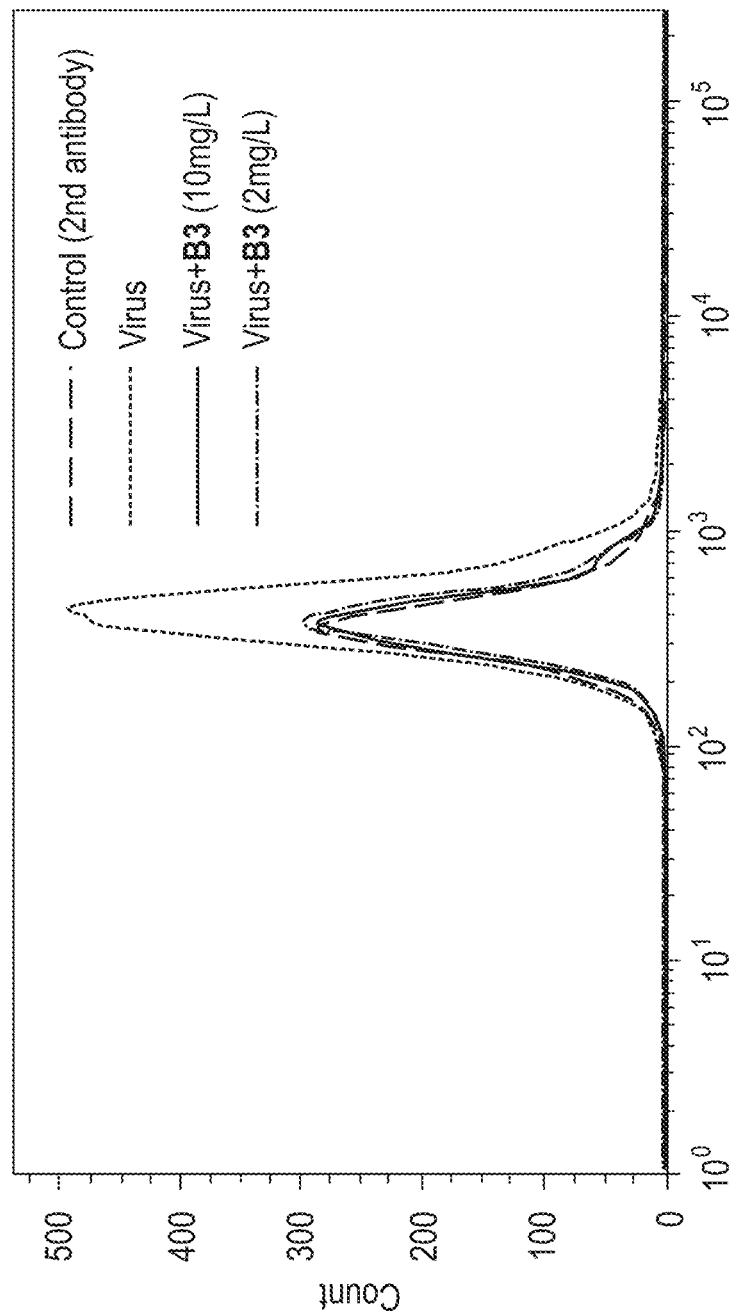
FIG. 4 is a graph showing the ability of cationic polyamine B3 to prevent infection of macrophages with the DENV-2 virus. After virus infection, the peak is shifted to a slightly higher PE-A. The peaks for the samples obtained from B3 treatment at 2 or 10 mg/L do not shift, but rather almost overlap with the peak for the control sample without virus infection, indicating that B3 treatment effectively prevents macrophages from DENV-2 infection.

The anti-viral activity of B3 against DENV-2 was further evaluated in clinically relevant human primary peripheral blood mononuclear cells (PBMCs, FIG. 3, graph) and macrophages (FIG. 4, graph). In FIG. 3, after virus infection, the peak shifts to a higher PE-A (phycoerythrin (PE)-conjugated anti-mouse IgG). The peaks for the samples obtained from B3 treatment at 2 or 10 mg/L do not shift, but rather almost overlap with the peak for the control sample without virus infection, indicating that B3 treatment effectively prevents human primary peripheral blood mononuclear cells from DENV-2 infection. In FIG. 4, after virus infection, the peak is shifted to a slightly higher PE-A. The peaks for the samples obtained from B3 treatment at 2 or 10 mg/L do not shift, but rather almost overlap with the peak for the control sample without virus infection, indicating that B3 treatment effectively prevents macrophages from DENV-2 infection. These results show that B3 effectively prevented the cells from DENV-2 infection. Both PBMCs and macrophages express mannose receptor, which mediates DENV-2 infection. The mannose groups of the modified PEI polymers compete with DENV-2 for binding the mannose receptor, thereby inhibiting the viral infection.

Broad-Spectrum Anti-Viral Activity

The anti-viral activity of mannose modified BPEI25 polymers B2 and B3 was further evaluated against a broad spectrum of viruses including other serotypes of dengue virus (DENV-1, 3 and 4), HSV-1, HSV-2, CHIKV, SARS Co-V, and EV 71. The results are listed in Table 5.

TABLE 5

| Virus | | | | Polymer | EC50[a] (mg/L) | CC50[b] (mg/L) | Selectivity[c] (CC50/EC50) |
|---|---|---|---|---|---|---|---|
| Name | Type | Family | Cell | | | | |
| DENV-1 | RNA | Flaviviridae | LLC-MK2 | B3 | 0.20 ± 0.17 | >1000 | >5000 |
| DENV-2 | RNA | Flaviviridae | LLC-MK2 | B3 | 0.31 ± 0.06 | >1000 | >3225 |
| DENV-3 | RNA | Flaviviridae | LLC-MK2 | B2 | 0.8 | 697 | 871 |
| DENV-4 | RNA | Flaviviridae | LLC-MK2 | B3 | 0.32 ± 0.02 | >1000 | >33125 |
| SARS Co-V | RNA | Coronaviridae | Vero | B3 | 300 | >1000 | >3.0 |
| CHIKV | RNA | Alfa-viridae | Vero | B3 | 7.0 ± 0.5 | >1000 | >143 |
| EV 71 | RNA | Enteroviridae | RD | B3 | 1.1 ± 0.09 | >1000 | >909 |
| Influenza virus (A/H3N2) | RNA | Orthomyxoviridae | MDCK | B2 | <0.012 | >1000 | >83333 |
| Influenza virus (A/H3N2) | RNA | Orthomyxoviridae | MDCK | B3 | >1000 | >1000 | |

TABLE 5-continued

| Virus | | | | | | CC50[b] | Selectivity[c] |
| --- | --- | --- | --- | --- | --- | --- | --- |
| Name | Type | Family | Cell | Polymer | EC50[a] (mg/L) | (mg/L) | (CC50/EC50) |
| HSV-1 | DNA | Herpes viridae | Vero | B3 | 1.6 ± 0.2 | >1000 | >625 |
| HSV-2 | DNA | Herpes viridae | Vero | B3 | 5.1 ± 0.2 | >1000 | >196 |
| Adenovirus 3 | DNA | Adenoviridae | A549 | B3 | >1000 | >1000 | |

[a]EC50 is effective concentration at which the polymer protects 50% cells from viral infection. A low EC50 value is desirable.
[b]CC50 is the cytotoxic polymer concentration, at which 50% of the cells are killed. A high CC50 value is desirable.
[c]Selectivity is defined as CC50/Ec50. A high selectivity is desirable.

B3 was active against DENV-1, DENV-2, and DENV-4 with EC50 values of 0.20, 0.32, and 0.31 mg/L, respectively. B3 had low activity against DENV-3 with an EC50 value of 479 mg/L. However, B2, having less mannose substitution and higher charge, was active against DENV-3 with EC50 of 0.80 mg/L. Notably, B3 effectively inhibited infections of respective target cells with the DNA viruses HSV-1 and HSV-2, and the RNA viruses CHIKV, SARS Co-V, and EV 71 (non-enveloped). B3 was ineffective against influenza infection, with EC50>1000 mg/L, whereas B2 effectively prevented infection of influenza virus, with a low EC50 value of <0.012 mg/L. These findings demonstrate broad-spectrum anti-viral activity of the polymers. Importantly, there was no significant cytotoxicity at concentrations where the polymer prevented 100% cells from infection.

Inhibition of Viral Infection in Cells Expressed with TIM-1 and TIM-3 Receptors

TIM receptors facilitate virus entry by directly interacting with phosphatidylserine (PS) on the viral envelope. Establishment of the 293T cells stably expressing the TIM-1 or TIM-3 protein, lentiviral vectors were generated as described by Tahara-Hanaoka S, et. al. "Lentiviral vector-mediated transduction of murine CD34-hematopoietic stem cells", Experimental Hematology, (2002), 30, pages 11-17). 293T cells were transfected with pseudoviruses carrying the desired ORF (open reading frame, a reading frame that contains no stop codons). Cells with the expression of TIM-1 or TIM-3 were selected by blasticidin (InvivoGen, Toulouse, France). 293T cells stably express TIM-1 or TIM-3 due to integration of TIM-1 or TIM-3 expression genes.

Parental (with empty vector), TIM-1, and TIM-3 expressing 293T cells were challenged with CHIKV at multiplicity of infection (M.O.I) 0.1 along with B3 (50 mg/L) added at the same time. Supernatants were collected 48 hours post-infection. Virus titers were determined by plaque assay and expressed as average plaque forming unit per ml (pfu/mL) of three replicates±SD.

Figure 5:
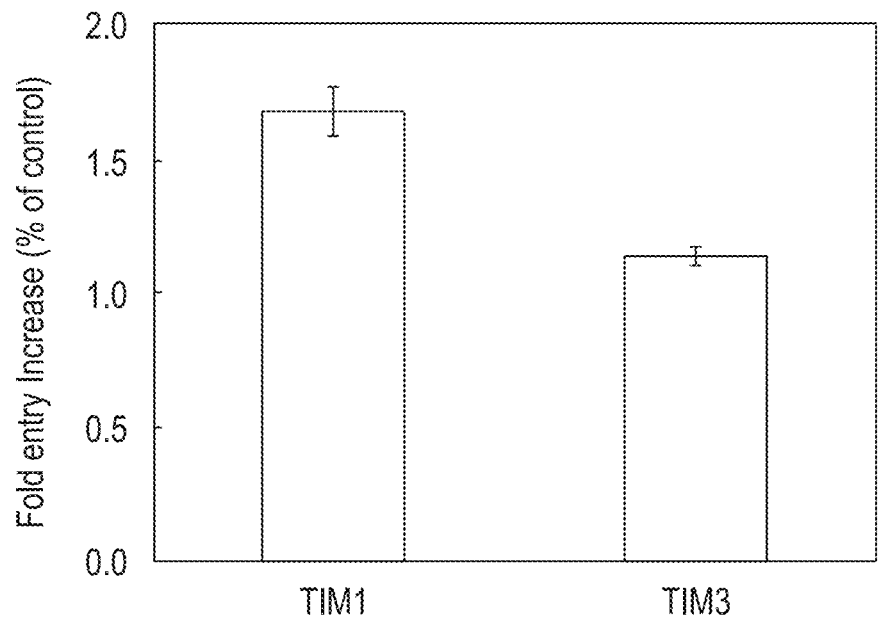
FIG. 5 is a bar graph comparing CHIKV (Chikungunya virus) infection rates of 293T cells expressing the TIM-1 receptor or TIM-3 receptor compared to empty vector 293T cells that do not express the TIM-1 receptor or the TIM-3 receptor (labeled "empty"). The presence of the TIM-1 receptor or TIM-3 receptor enhances CHIKV infection.
Figure 6:
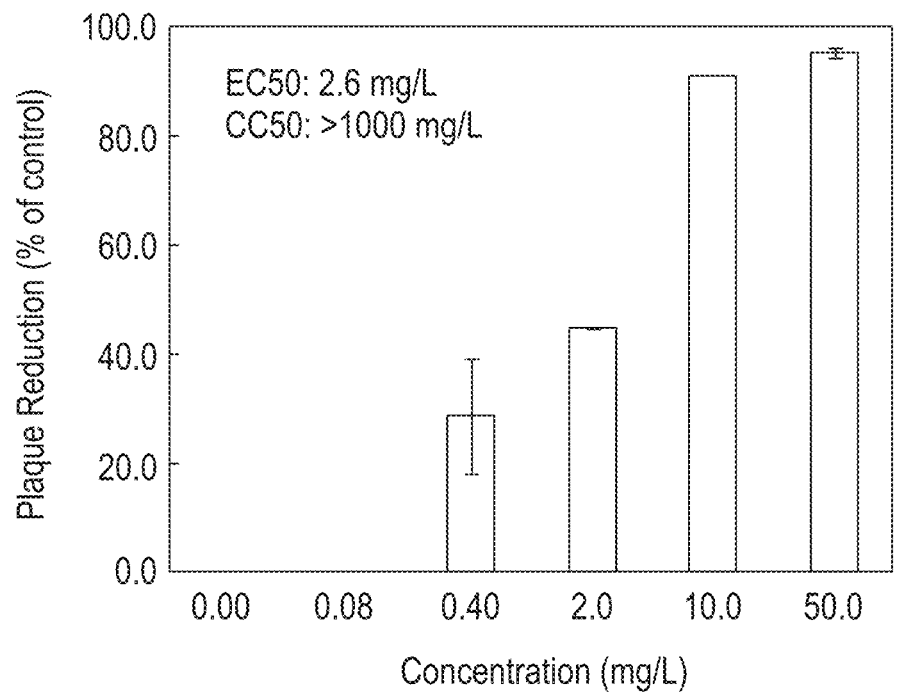
FIG. 6 is a bar graph showing the effect of cationic polyamine B3 in preventing CHIKV infection of empty vector 293T cells (i.e., that do not express the TIM-1 or TIM3 receptor). The EC50 was 0.21 mg/L.
Figure 7:
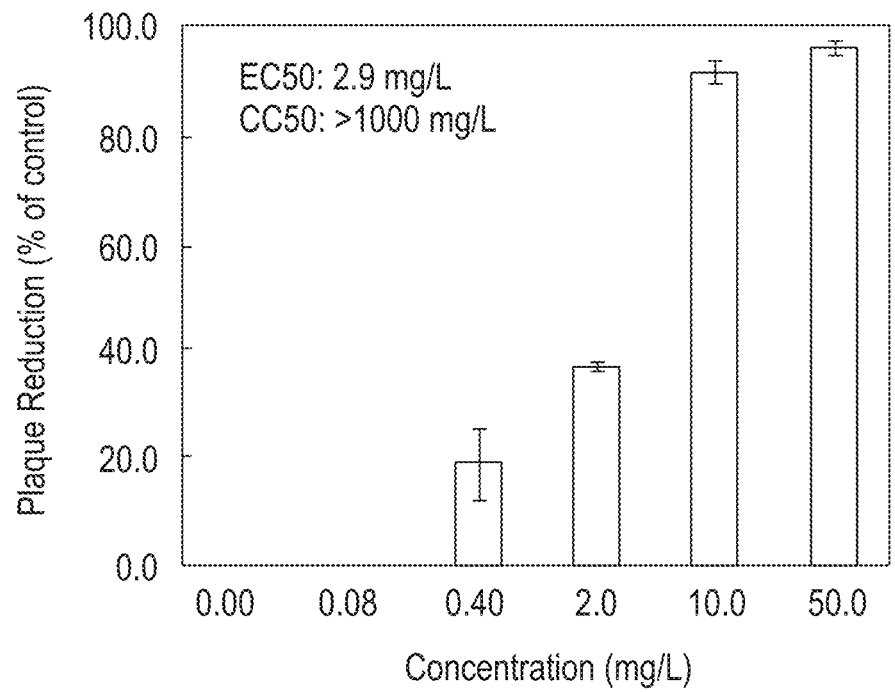
FIG. 7 is a bar graph showing the effect of cationic polyamine B3 in preventing CHIKV infection in the 293T cells that express the TIM-1 receptor. The EC50 was 1.26 mg/L and the selectivity index (CC50/EC50) was >794.
Figure 8:
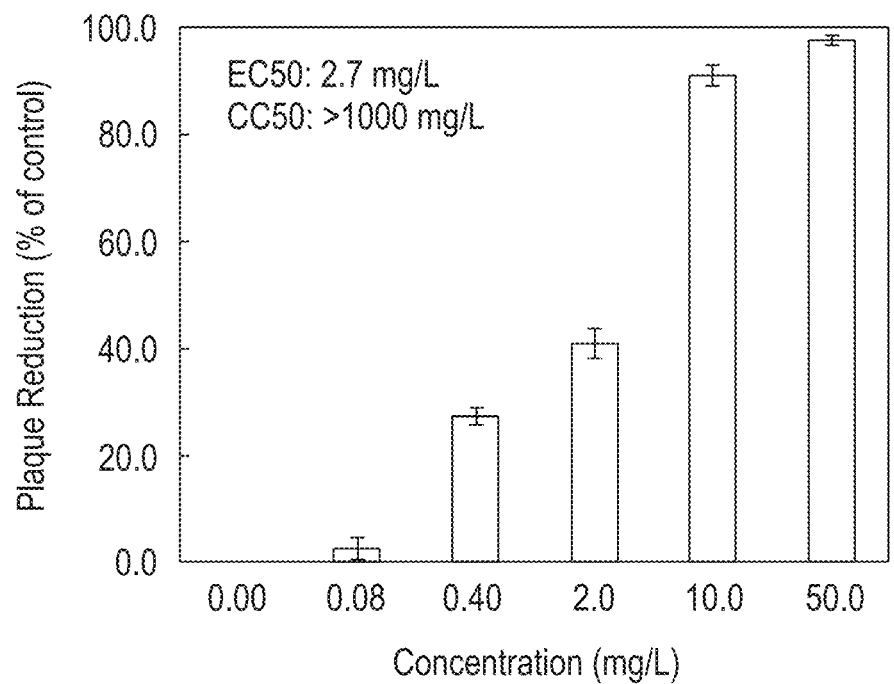
FIG. 8 is a bar graph showing the effect of cationic polyamine B3 in preventing CHIKV infection in the 293T cells that express the TIM-3 receptor. The EC50 was 0.68 mg/L and the selectivity index (CC50/EC50) was >1471.

Expression of TIM-1 and TIM-3 receptors in 293T cells significantly enhanced CHIK infection (FIG. 5, bar graph, TIM1-293T and TIM3-293T versus empty vector-293T cells). FIG. 6 is a bar graph showing the effect of B3 in preventing CHIKV infection of the empty vector 293T cells (i.e., that do not express the TIM-1 or TIM-3 receptor), where the EC50 was 2.6 mg/L. FIG. 7 is a bar graph showing the effect of B3 in preventing CHIKV infection in the TIM1-293T cells, where the EC50 was 2.9 mg/L. FIG. 8 is a bar graph showing the effect of B3 in preventing CHIKV infection in the TIM3-293T cells, where the EC50 was 2.7 mg/L. The selectivity (CC50/EC50) towards preventing CHIKV infection in TIM-1 and TIM-3 expressing cells was high (>345 and >370, respectively).

Figure 9:
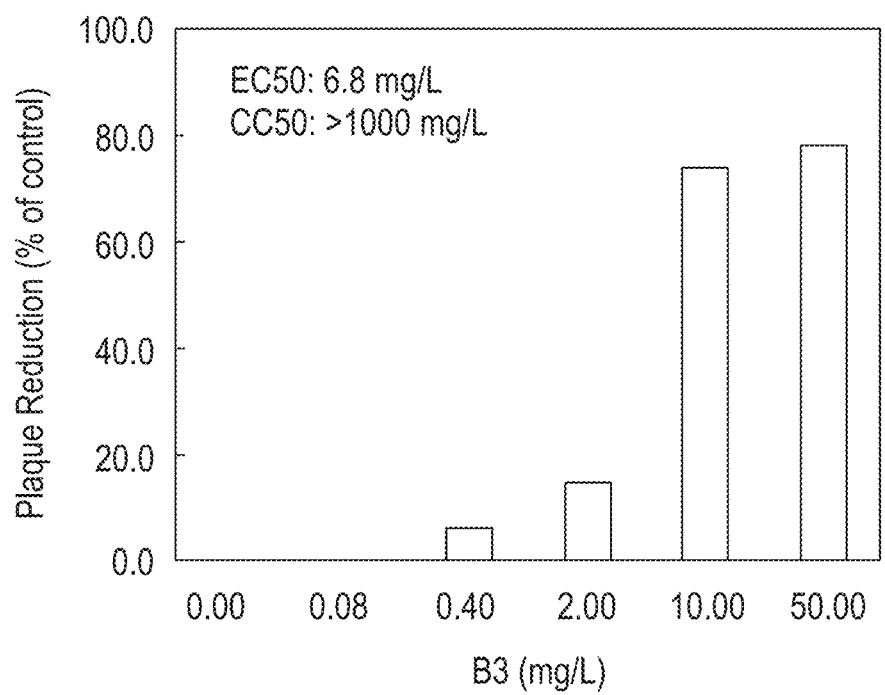
FIG. 9 is a bar graph showing the effect of cationic polyamine B3 in preventing DENV-2 infection of A549 cells that naturally express TIM-1 receptor. The EC50 was 6.8 mg/L, the CC50 was >1000 mg/L, and the selectivity index was >147.

B3 also effectively inhibited DENV-2 infection of A549 cells that naturally express the TIM-1 receptor (FIG. 9, bar graph). In this instance the EC50 was 6.8 mg/L, CC50 was >1000 mg/L, and the selectivity index was >147, measured by plaque reduction assay. These findings suggest that the polymer is capable of inhibiting the phosphatidyl-serine (PS)/TIM receptor binding possibly by hydrogen-bonding interactions between polymer and TIM-1/TIM-3 receptors (see below FIGS. 34-37) and/or electrostatic interaction between the cationic charges on the polymer and the negative charges on the PS, hence preventing viral infection of cells with TIM-1 or TIM-3 receptor expression.

Anti-Viral Mechanism

Inhibition of Viral Entry

Viral particles infect cells by specific interactions of their surface proteins with receptors including proteins, mannose receptors (also targeted by immune cells), heparan sulfate proteoglycans (targeted by DENV, HSV, EV 71, SARS-CoV) and sialic acid (influenza virus, EV 71) on the cell membrane, followed by endocytosis internalization. Viruses spread viral genome and infection from cell to cell. To study if the polymer exerts its anti-viral effect at an early or late stage of virus life cycle, the effect of the macromolecule on the replication of DENV-2 subgenomic replicon, encoding only non-structural viral proteins, was studied in luciferase-replicon transfected A459 cells.

Replicon luciferase assay. A549 cells (human male lung carcinoma) containing a luciferase-reporting replicon of DENV-2 were seeded at a cell density of 25×10⁴ cells/well in 6-well plates. The cells were treated with 50 mg/L of B3 polymer c, 100 mg/L of NITD008, or medium with DMSO. NITD008 was not water soluble, and a small amount of DMSO (dimethylsulfoxide) was used to promote its dissolution in the cell culture medium. After incubation for 48 hours, luciferase activity was measured using the *Renilla* luciferase assay system (Promega, Madison, Wis.). Results were normalized by protein quantity.

Figure 10:
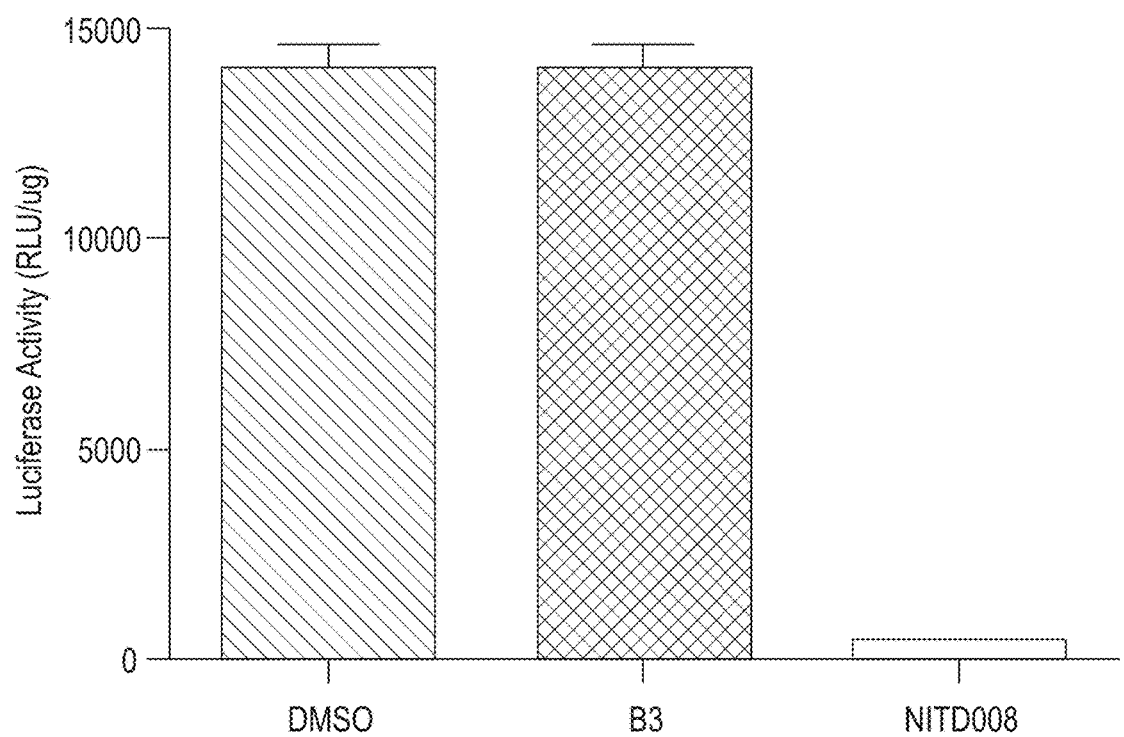
FIG. 10 is a bar graph comparing the luciferase activity of the cells with cationic polyamine B3, without B3 (labeled DMSO), and with a potent anti-viral adenosine nucleoside analogue NITD008 (2R,3R,4R,5R)-2-(4-aminopyrrolo[2,3-d]pyrimidin-7-yl)-3-ethynyl-5-(hydroxy-methyl)oxolane-3,4-diol. This finding demonstrated that anti-viral polymer B3 did not function at a late stage of the DENV-2 cell entry and replication cycle.

FIG. 10 is a bar graph comparing the luciferase activity of the A459 cells without B3 (labeled DMSO), with B3, and a with a potent anti-viral adenosine nucleoside analogue NITD008, (2R,3R,4R,5R)-2-(4-aminopyrrolo[2,3-d]pyrimidin-7-yl)-3-ethynyl-5-(hydroxymethyl)oxolane-3,4-diol.

The results show that NITD008 was effective and B3 was not effective in inhibiting replication of the DENV-2 subgenomic replicon. This finding demonstrated that the antiviral polymer did not function at a late stage of the DENV-2 life cycle.

Figure 11:
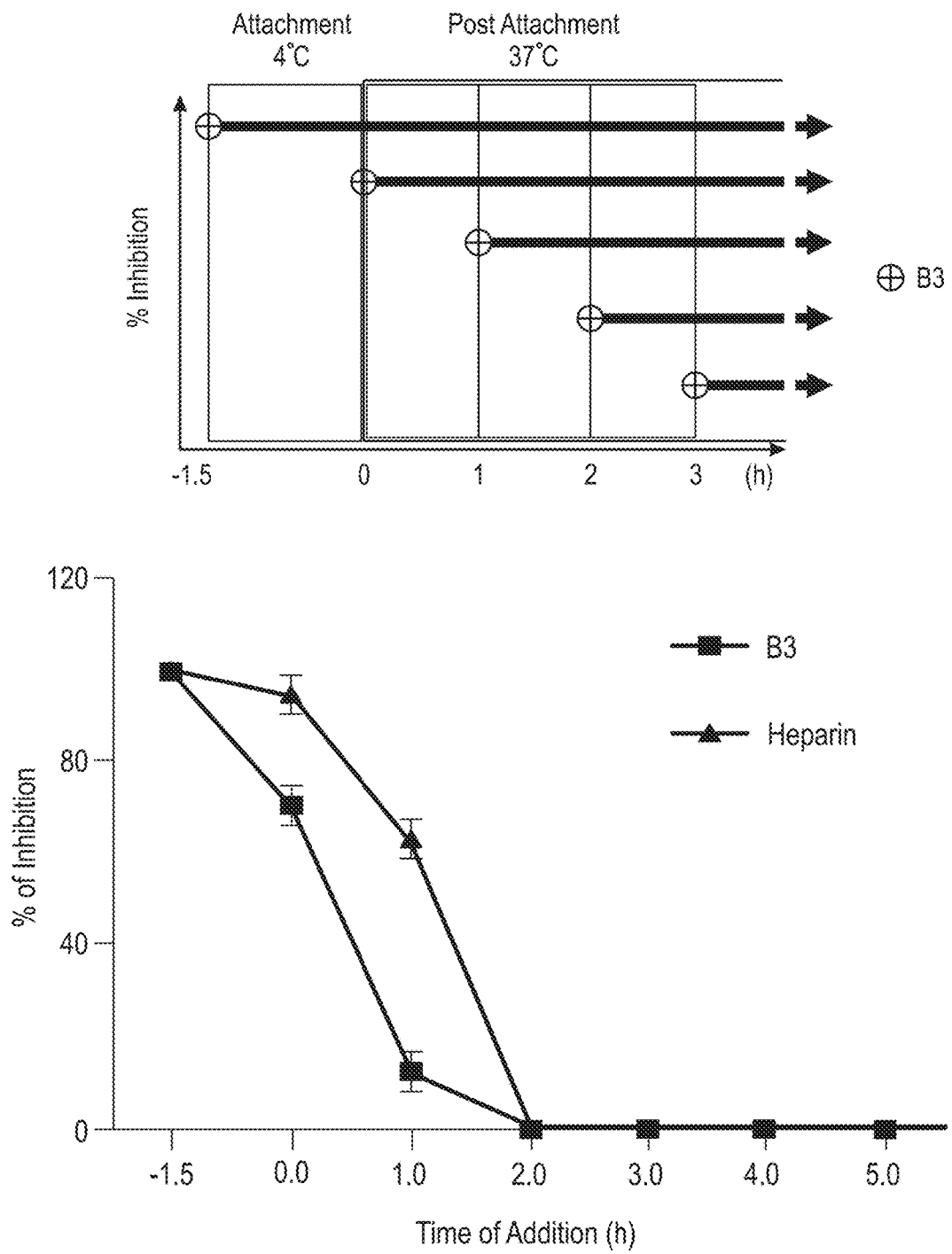
FIG. 11 is a set of graphs showing the effect of time of addition of cationic polyamine B3 (and heparin) on the inhibition of DENV-2 in LLC-MK2 cells. For time=−1.5 hours, the virus and B3 were added together to the cells at 4° C. For all other times, B3 was added after the virus and cells were incubated at 4° C. for 1.5 hours and warmed to 37° C. The results show B3 was effective in preventing viral infection when added during the viral attachment step or early post-attachment step (0-1 hours), but was not effective thereafter.

To examine if the polymer blocked the initial attachment step in the LLC-MK2 cells or a downstream event in the viral entry process, B3 was added together with DENV-2 to the cells for 90 minutes at 4° C. Unbound polymer molecules were then removed by PBS wash (3 times) before the cells were incubated for 5 days at 37° C. The B3 polymer inhibited DENV-2 infection completely at this time of addition (−1.5 hours). Other times of addition were evaluated. FIG. 11 is set of graphs showing the effect of time of addition of B3 (and heparin) on the inhibition of DENV-2 in LLC-MK2 cells. The top graph shows the time of addition of B3 and heparin. The bottom graph depicts the % inhibition obtained for each time of addition. Only at time −1.5 hours were the virus and polymer B3 (or heparin) added together to the cells. At all other times, the virus and cells were incubated initially at 4° C. without the polymer B3 or heparin, followed by warming to 37° C., followed by addition of B3 or heparin at the indicated times. The results show that the viral infection was effectively prevented when the polymer was added to the cells just after the cells and virus were incubated at 4° C. for 90 minutes and warmed to a 37° C. (corresponding to Time=0 hours). However, when the polymer was added to the cells after the cells and DENV-2 were incubated for 1 hour at 37° C., inhibition was significantly reduced. No considerable inhibition was observed when the polymer was introduced after the cells were infected with the virus for 2-5 hours at 37° C. These results demonstrated that the polymer was effective in preventing viral infection when added during the viral attachment step or early post-attachment step, confirming the point of action at DENV entry/membrane fusion.

Figure 12:
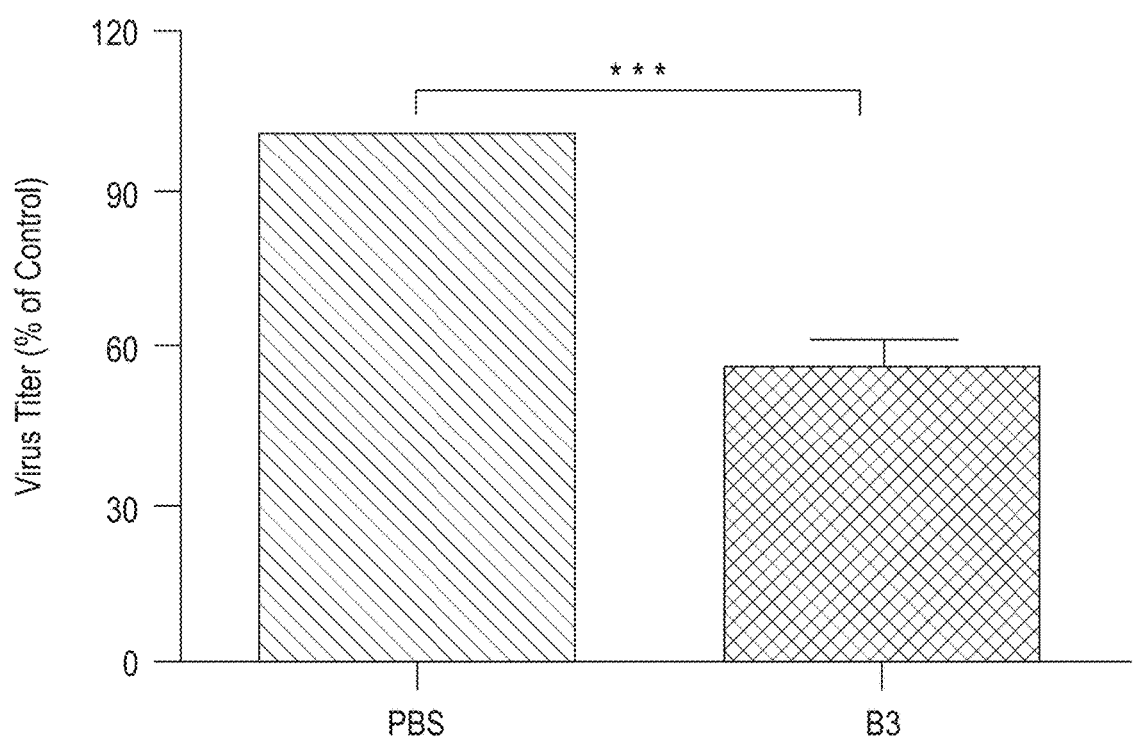
FIG. 12 is a bar graph showing the effect of combining the DENV-2 virus and cationic polyamine B3 one hour at 4° C. before the addition of LLC-MK2 cells. A 40% reduction in virus titer was obtained, indicating B3 binding to the virus inhibited viral infection.

To further understand the anti-viral mechanism, DENV-2 was incubated with 50 mg/L B3 for one hour at 4° C. for binding before performing a plaque assay to measure virus titers. Virus binding with the polymer lowered virus titers by more than 40%, indicating that the polymer bound the virus, and prevented infection (FIG. 12, bar graph). In the cell culture medium (pH 7.4), the majority of primary and secondary amines are protonated, making the polymer highly charged.

In addition to the specific viral protein/polymer interaction, the cationic charges of the polymer might interact with the anionic charges on the envelope of virus through electrostatic interaction. This might mask the virus, preventing the cells from viral infection.

Figure 13:
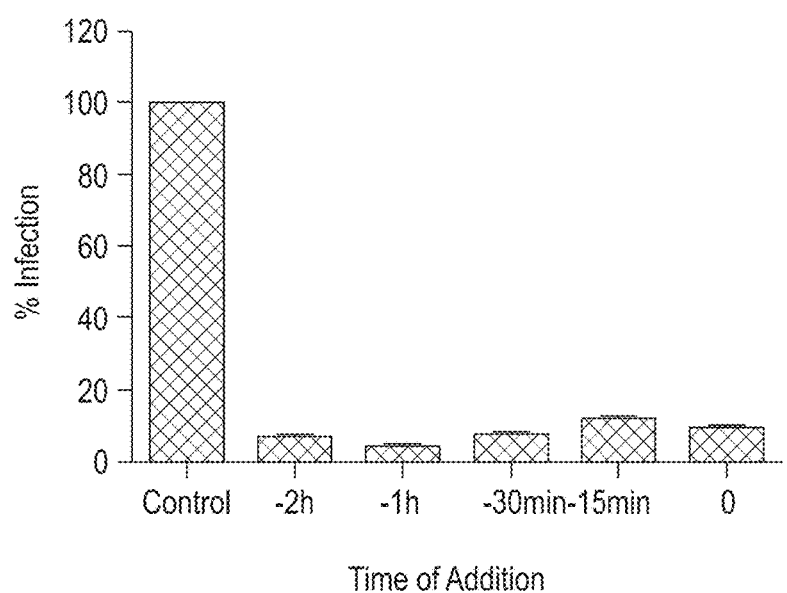
FIG. 13 is a bar graph showing the effect of pretreating LLC-MK2 cells with cationic polyamine B3 for 15 minutes to 2 hours at 37° C. before the addition of DENV-2 virus. The EC50 value was 8.7 mg/L, indicating B3 binding to the cell membrane was a factor in inhibiting infection by DENV-2 virus.

On the other hand, at 50 mg/L, the polymer B3 yielded complete inhibition of viral infection when it was added to the cells together with the virus. The incomplete inhibition of virus titers after polymer binding at the same concentration implied that there were other factors such as binding between the polymer and anionic components on the cell membrane (anionic heparin sulfate proteoglycans) and neutralization of the endosomal pH, which contributed to the inhibition of viral infection. Although all primary amine groups were substituted by mannose groups, B3 carries cationic charges at pH 7.4 as the majority of secondary amine groups (pKa: 8.6) and ~50% tertiary amines (pKa: 7.5) can be protonated. Indeed, the pretreatment of the cells using 50 mg/L B3 at 2 hours or even 15 minutes effectively prevented DENV-2 infection (FIG. 13, bar graph). The EC50 value of B3 against DENV-2 infection was 6.0 mg/L when the cells were pre-incubated with B3 for one hour before the virus was added. This value was higher than when the polymer, cell and virus were incubated at the same time (EC50: 0.30 mg/L, Table 4). The pretreatment of Vero and RD cells was also highly effective against CHIKV, HSV-1 and EV 71 at EC50 values of 23.5, 1.8 and 0.80 mg/L, respectively. These findings indicate that binding of B3 onto the cell membranes was an important factor in blocking viral entry.

Figure 14:
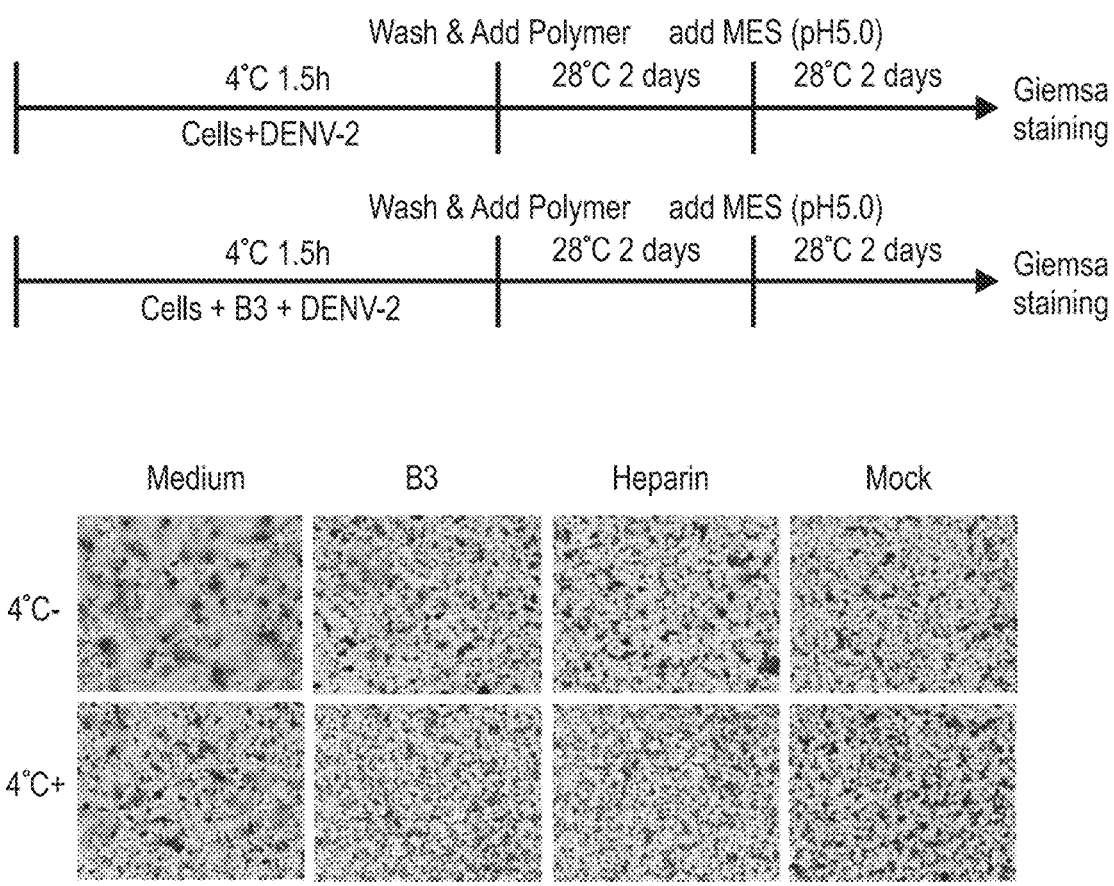
FIG. 14 is a set of photomicrographs and corresponding procedure diagrams showing the effect of cationic polyamine B3 and heparin on virus-infected cell fusion. *Aedes albopictus* C6/36 cells were treated with DENV-2 virus. The anti-viral agent was added at 4° C. (images labeled "4° C.+") or at 28° C. (images labeled "4° C.−"). The samples labeled "Medium" contained only cells and virus (no anti-viral agent). The samples labeled "Mock" contained only cells (no virus or anti-viral agent). No fused cells were found in the samples containing B3.

In addition, the unprotonated secondary and tertiary amines of PEI polymers are capable of being protonated in the endosomal environment (pH 5.0-6.5), thus neutralizing the endosomal pH. Neutralization of the endosomal pH is known to inhibit pH-dependent viral infections such as DENV, CHIKV, influenza virus, HSV, and EV 71. To prove that the polymer is able to inhibit low pH-induced virus-cell membrane fusion, prevention of low pH-induced virus-infected cell fusion was investigated. Virus-infected cell fusion was reported to be due to fusogenic viral proteins that are expressed on the cell surface after infection. C6/36 *Aedes albopictus* cells were incubated with DENV-2 for 90 minutes at 4° C. with and without B3 (50 mg/L), followed by incubation at 28° C. for 2 days to allow infection and for another 2 days after acidification to pH 5.0 with MES (2-(N-morpholino)ethanesulfonic acid). FIG. 14 is a set of photomicrographs and corresponding procedure diagrams showing the effect of B3 and heparin on virus-infected cell fusion of the C6/36 cells. The anti-viral agent was added at 4° C. (images labeled "4° C.+") or at 28° C. (images labeled "4° C.−"). The samples labeled "Medium" contained only cells and virus (no anti-viral agent). The samples labeled "Mock" contained only cells (no virus or anti-viral agent). No fused cells were found in the samples containing B3. Unlike the control group without any treatment, no fused cells were found in the samples containing B3. The polymer inhibited syncytia formation even when it was added at the point of viral infection (i.e., incubation at 28° C.), suggesting that the polymer was indeed capable of preventing low pH-induced virus-cell membrane fusion and viral infection.

Summarizing, in general with the treatment of DENV, cationic polymers with higher levels of mannose had lower capacity to neutralize the endosomal pH and less cationic charge, which diminished anti-viral activity. Without being bound by theory, polymer-virus binding, polymer-cell membrane interaction and neutralization of the endosomal pH acting together may explain prevention of viral infection.

Prevention of Drug Resistance.

Although there are anti-viral drugs available for some viral infections such as influenza, viruses are able to develop drug resistance via mutations. For example, adamantane resistance (e.g., resistance to M2 protein inhibitors) has been frequently found in circulating influenza strains since 2003. Oseltamivir and zanamivir (neuraminidase inhibitors), which are effective against adamantane-resistant influenza viruses and recommended by the Center for Disease Control, USA (CDC) for treatment and prophylaxis of influenza infections, have also seen reduced effectiveness in a small number of influenza viruses. Resistance is associated with a single amino acid change in M2 or neuraminidase protein. In order to investigate if the antiviral activity mediated by the polymers through multiple mechanisms adequately prevents drug resistance development, DENV-2 exposed to a sub-lethal dose of B3 (0.31 mg/L) was passaged and used to determine EC50 values up to 5 passages. EC50 values remained similar (0.31-0.35 mg/L). In addition, after passage 5, the virus was treated with the polymer at 100 mg/L, which completely inhibited DENV-2 infection. These results indicate that repeated treatment with B3 did not mediate resistance in DENV-2.

In Vivo Toxicity

To demonstrate the potential of the cationic polyamines for in vivo applications, the in vivo toxicity levels of B2 and B3 were investigated. The LD50 values (lethal dose at which half the mice are killed in a two week period) via intravenous injection of B2 and B3 were determined to be 313 mg/kg and 463 mg/kg, respectively, indicating that the cationic polyamines have low toxicity.

To evaluate the acute toxicity of B3 towards major organs (the liver and kidney) and the blood, alanine transaminase (ALT), aspartate transaminase (AST), total bilirubin (TBIL), creatinine, urea nitrogen, sodium ion, and potassium ions levels were measured in blood samples taken from B3-treated mice 48 hours after intravenous injection. Table 6 lists the results. The data are expressed as mean+standard deviation, based on values obtained from 10 mice (n=10). Statistical analysis was performed using Student's t-test. Differences are considered statistically significant with probability P<0.05. The following abbreviations are used: ALT=alanine transaminase; AST=aspartate transaminase; TBIL=total bilirubin; Units=international units.

TABLE 6

| Treatment | ALT (Units/L) | AST (Units/L) | TBIL | Creatinine (micromol/L) | Urea nitrogen (mmol/L) | $K^+$ (mmol/L) | $Na^+$ (mmol/L) |
|---|---|---|---|---|---|---|---|
| w/o treatment | 21.0 ± 4.9 (n = 10) | 58.2 ± 13.2 (n = 10) | 2.0 ± 0.0 (n = 10) | 10.8 ± 1.7 (n = 10) | 6.9 ± 0.9 (n = 10) | 4.7 ± 0.3 (n = 10) | 147.7 ± 1.9 (n = 10) |
| 48 hours post-treatment | 23.3 ± 3.6 (n = 10) $p = 0.40 > 0.05$ | 65.0 ± 23.8 (n = 10) $p = 0.21 > 0.05$ | 2.1 ± 0.3 (n = 10) $p = 0.34 > 0.05$ | 11.4 ± 1.0 (n = 10) $p = 1.0 > 0.05$ | 6.0 ± 0.4 (n = 10) $p = 0.55 > 0.05$ | 4.8 ± 0.2 (n = 10) $p = 0.47 > 0.05$ | 143.9 ± 2.4 (n = 10) $p = 0.43 > 0.05$ |
| 14 days post-treatment | 21.9 ± 1.8 (n = 10) $p = 0.60 > 0.05$ | 64.8 ± 20.4 (n = 10) $p = 0.45 > 0.05$ | 2.0 ± 0.0 (n = 10) $p = 1.0 > 0.05$ | 10.7 ± 0.8 (n = 10) $p = 1.0 > 0.05$ | 7.5 ± 0.6 (n = 10) $p = 0.44 > 0.05$ | 4.6 ± 0.3 (n = 10) $p = 0.27 > 0.05$ | 145.5 ± 1.1 (n = 10) $p = 0.31 > 0.05$ |

There was no significant difference in any of the measured parameters between the control group and the group receiving intravenous injection of B3 at a concentration well above its effective concentration (dose: 60 mg/kg; estimated concentration in the blood: 1200 mg/L, assuming that the blood volume of the mouse is ~1 mL), indicating that the polymer treatment did not lead to any acute liver or kidney damage, nor interfere with the electrolyte balance of the blood. In addition, even at 14 days post-injection, the liver and kidney functions, potassium and sodium ion concentrations remained unchanged as compared to the control. Moreover, the polymer treatment did not induce any abnormal color change in the serum or urine samples, or cause lethality in mice. These results prove that the polymer treatment was not toxic in mice during the period of testing.

Blind Docking Study of Modified and Unmodified PEI with Viral Proteins

Blind docking study provides insight into binding interactions between polymer and viral proteins.

Figure 15:
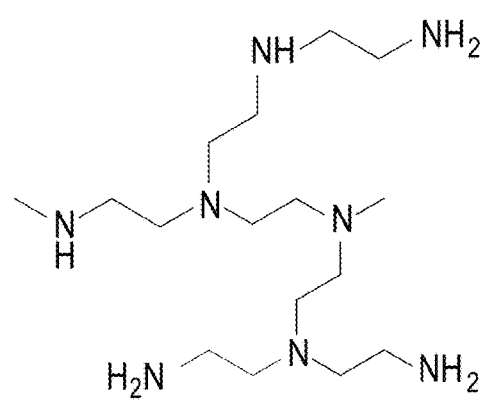
FIG. 15 is a two dimensional structure of a model macromolecule of model branched PEI built using Marvin Sketch software. The model branched BPEI was not intended to represent the complete structure of the branched PEI used in the examples.

The crystal structure of DENV-2 E glycoprotein was retrieved from the Protein Data Bank (PDB ID: 1OKE). The crystal structure details E protein in its dimeric pre-fusion conformation. The crystal structures of DENV-3 (PDB ID: 1UZG), HSV-1 (PDB ID: 1JMA), HSV-2 (PDB ID: 4MYW), influenza virus (PDB ID: 4KVN) and TIM1 (PDB ID: 2OR8) were also retrieved from PDB. The amino acid sequence for CHIKV (ID: ACT35081.1) and EV 71 (ID: ACS12925) were downloaded from National Center for Biotechnology Information (NCBI, USA) and the protein structures were modelled using the I-Tasser online server. The two dimensional structure of a model macromolecule of branched PEI (FIG. 15) was built using Marvin Sketch software and converted into three dimensional structure using OpenBabel software. The model branched PEI and a model cationic polyamines B3 and B2 that were used in the docking study were not intended to represent the complete structures of the branched PEI and B3 materials of the above examples. The model B3 material had 3 mannose groups, and the model B2 material had 2 mannose groups. MVD (Molegro Virtual Docker) was used to identify the potential binding sites of B3 and non-modified branched PEI in the viral proteins in order to perform the molecular docking analysis. A cavity detection algorithm was used to detect cavities in order to narrow down the binding sites. The structures of protein and ligand (one unit of macromolecule of model branched PEI or model cationic polyamine B3) were prepared by MVD. Bonds, hydrogens, and bond orders were assigned if missing. The charges and flexible torsions in the ligand were assigned. The grid-based MolDock scoring function was used to define the energy terms to rank the potential binding sites. Grids of 30 Å radius were used as search space on the proteins. The MolDock Simplex evolution algorithm was chosen with a population size of 100. The simplex minimization procedure was performed and the energy threshold was set to 100 for pose generation.

The protein-polymer interaction was analyzed through the flexible ligand docking study. Interaction between a ligand and a protein is defined as specific when the ligand binds to the protein at a specific binding site with the least energy, while interaction is defined as non-specific when the ligand binds to the protein at various sites in the same range of energy. Five binding poses in each grid were obtained from the flexible docking, and by ranking Moldock and rerank scores of the poses, the one with the least score was considered to be the best docking pose. The best pose is predicted to be present in one of the five cavities detected by the MVD software.

Figure 16:
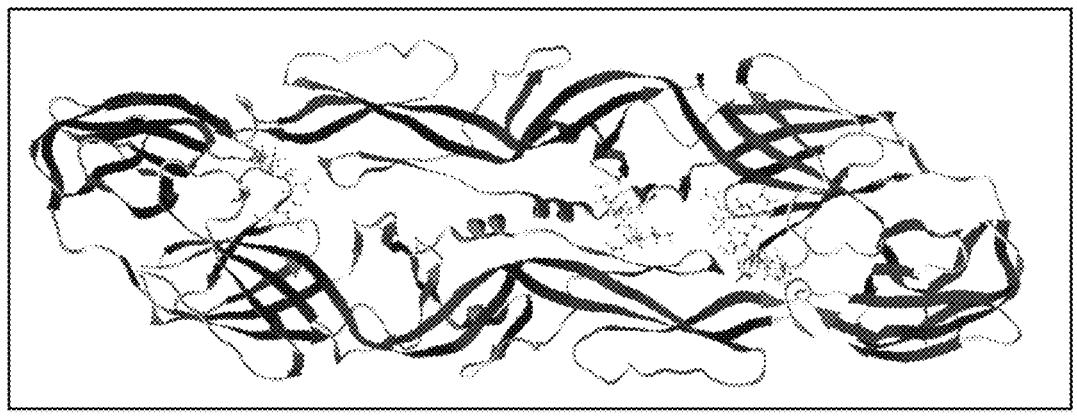
FIG. 16 is a 3-dimensional computer drawing using MVD (Molegro Virtual Docker) software of the DENV-2 E protein (envelope protein), with highlighted speckled areas representing 4 poses of the model branched PEI bound with equal binding energy in 4 docking grids.

The DENV-2 E protein (envelope protein) has 5 cavities. The MVD docking studies of the DENV-2 E protein were performed utilizing 4 grids. FIG. 16 is an MVD 3-dimensional computer drawing of the DENV-2 E protein, in which the highlighted speckled areas represent 4 poses of the model branched PEI bound with equal binding energy in the 4 grids. The hydrogen bonds were estimated.

Figure 17:
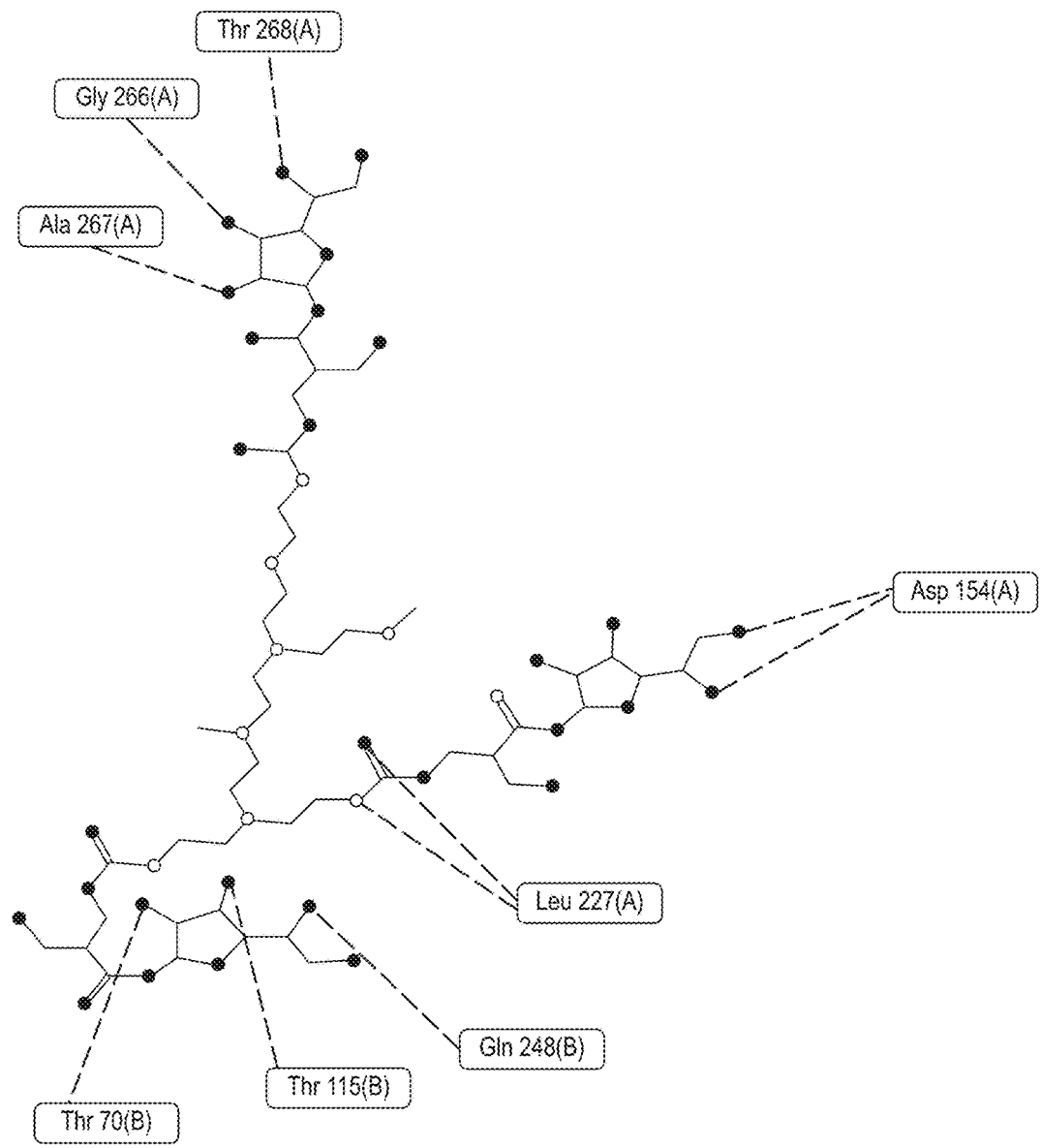
FIG. 17 is a computer drawing using MVD software showing the 8 amino acid residues of the DENV-2 E protein that form hydrogen bonds with a model cationic polyamine B3 structure: Thr 268(A), Gly 266(A), Ala 267(A), Thr 70(B), Thr 115(B), Gln 248(B), Leu 277(A), and Asp 154(A). The model cationic polyamine B3 structure was not intended to represent the complete structure of B3 prepared in the examples. The model B3 material had 3 mannose groups.
Figure 18:
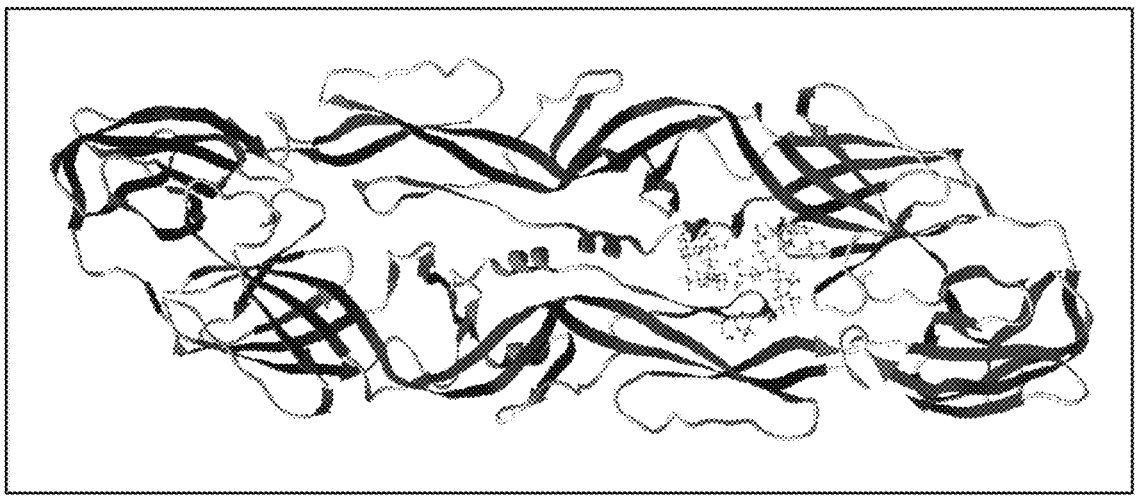
FIG. 18 is a 3-dimensional computer drawing using MVD software of the favored binding interaction of the model cationic polyamine B3 with the DENV-2 E protein.

The specific binding site of the model cationic polyamine B3 to the DENV-2 E protein was predicted to be at the interface of the domain II and domain III of the E protein dimer and near the fusion loop of the E protein monomer. FIG. 17 is a computer drawing showing the 8 amino acid groups of the DENV-2 E protein (envelope protein) that form hydrogen bonds with a model cationic polyamine B3 structure: Thr 70, Thr 115, Asp 154, Gln 248, Gly 266, Ala 267, Thr 268 and Leu 277. FIG. 18 is a 3-dimensional computer drawing of the most favored binding of the model cationic polyamine B3 to the DENV-2 E protein. The binding site is also located in a pocket above the flexible 'kl' loop lining the hydrophobic cavity called the BOG binding pocket by previous studies.

Figure 19:
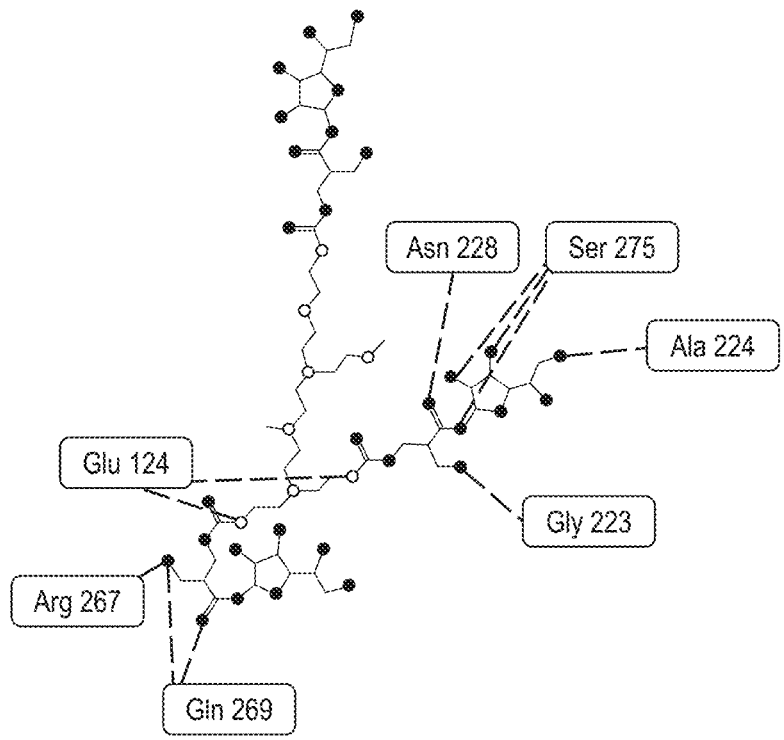
FIG. 19 is a computer drawing using MVD software showing the 7 amino acid groups of EV 71 VP1 protein that form hydrogen bonds with the model cationic polyamine B3: Gln 269, Arg 267, Glu 124, Asn 228, Ser 275, Ala 224, and Gly 223.

FIG. 19 is a computer drawing using MVD software showing the 7 amino acid groups of EV 71 VP1 protein that form hydrogen bonds with the model cationic polyamine B3: Gln 269, Arg 267, Glu 124, Asn 228, Ser 275, Ala 224, and Gly 223.

Figure 20:
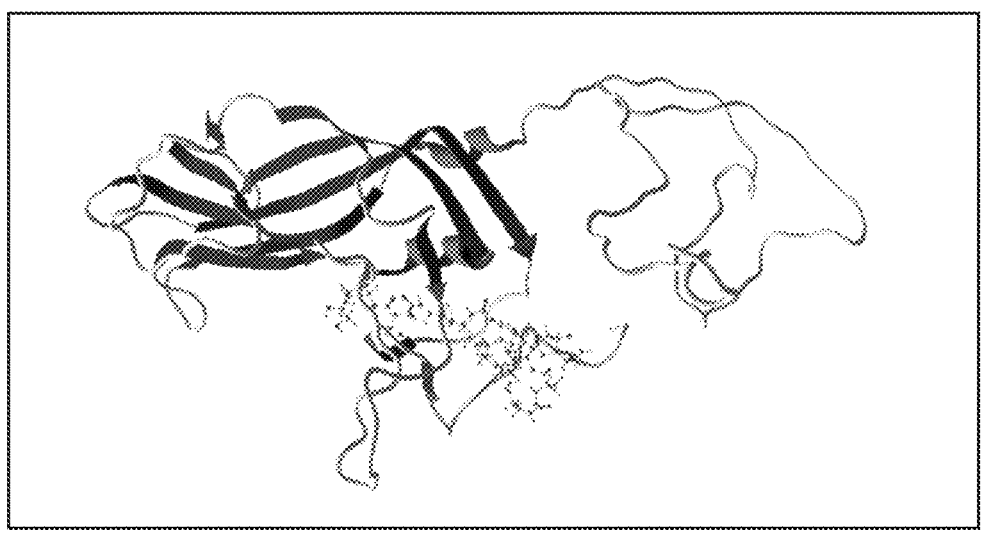
FIG. 20 is a 3-dimensional computer drawing using MVD software showing the favored binding interaction of the model cationic polyamine B3 with the EV 71 VP1 protein.

FIG. 20 is a 3-dimensional computer drawing using MVD software showing the most favored binding of the model cationic polyamine B3 with the EV 71 VP1 protein.

Figure 21:
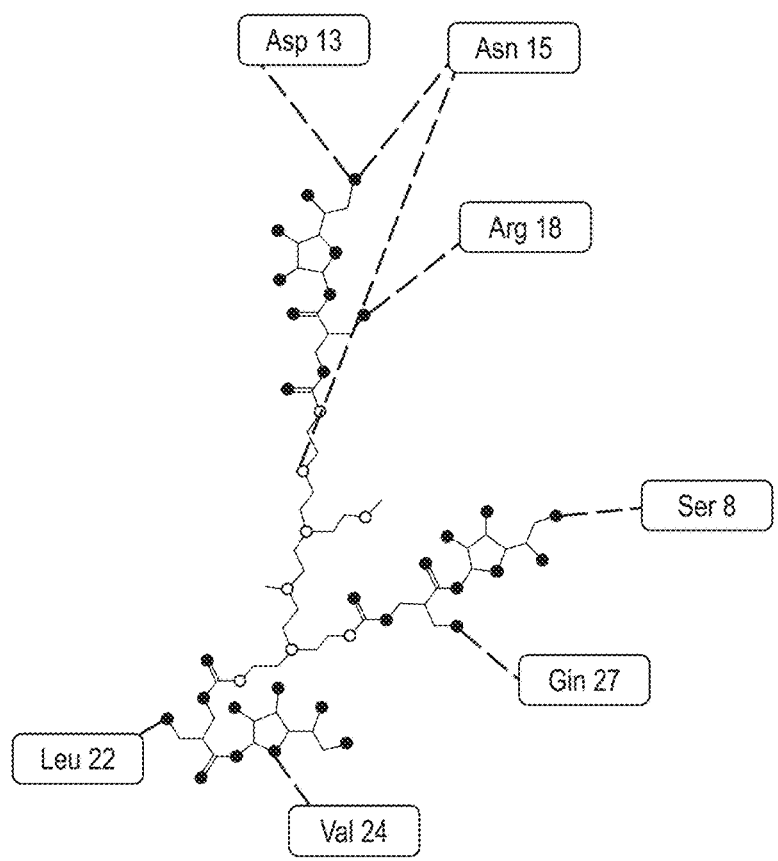
FIG. 21 is a computer drawing using MVD software showing the 7 amino acid groups of HSV-1 GD protein that form hydrogen bonds with the model cationic polyamine B3: Asp 13, Asn 15, Arg 18, Leu 22, Val 24, Gln 27, Ser 8.

FIG. 21 is a computer drawing using MVD software showing the 7 amino acid groups of HSV-1 GD protein that form hydrogen bonds with the model cationic polyamine B3: Asp 13, Asn 15, Arg 18, Leu 22, Val 24, Gln 27, Ser 8.

Figure 22:
FIG. 22 is a 3-dimensional computer drawing using MVD software showing the most favored binding interaction of the model cationic polyamine B3 with the HSV-1 GD protein.

FIG. 22 is a 3-dimensional computer drawing using MVD software showing the most favored binding interaction of the model cationic polyamine B3 with the HSV-1 GD protein.

Figure 23:
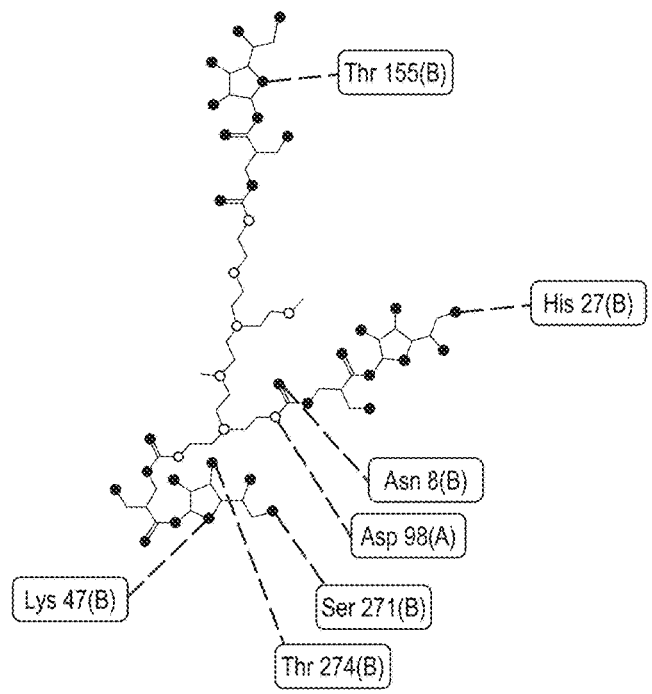
FIG. 23 is a computer drawing using MVD software showing the 7 amino acid residues of DENV-3 E protein that form hydrogen bonds with the model cationic polyamine B3: Thr 155(B), Lys 47(B), Thr 274(B), Ser 271(B), Asn 8(B), and Asp 98(A), His 27(B)
Figure 24:
FIG. 24 is a 3-dimensional computer drawing using MVD software of 5 cavities in the DENV-3 E protein.

FIG. 23 is a computer drawing using MVD software showing the 7 amino acid residues of DENV-3 E protein that form hydrogen bonds with the model cationic polyamine B3: Thr 155(B), Lys 47(B), Thr 274(B), Ser 271(B), Asn 8(B), and Asp 98(A), His 27(B), The DENV-3 E protein has 5 cavities detected by MVD software. FIG. 24 is a 3-dimensional computer drawing using MVD software of 5 cavities in the DENV-3 E protein.

Figure 25:
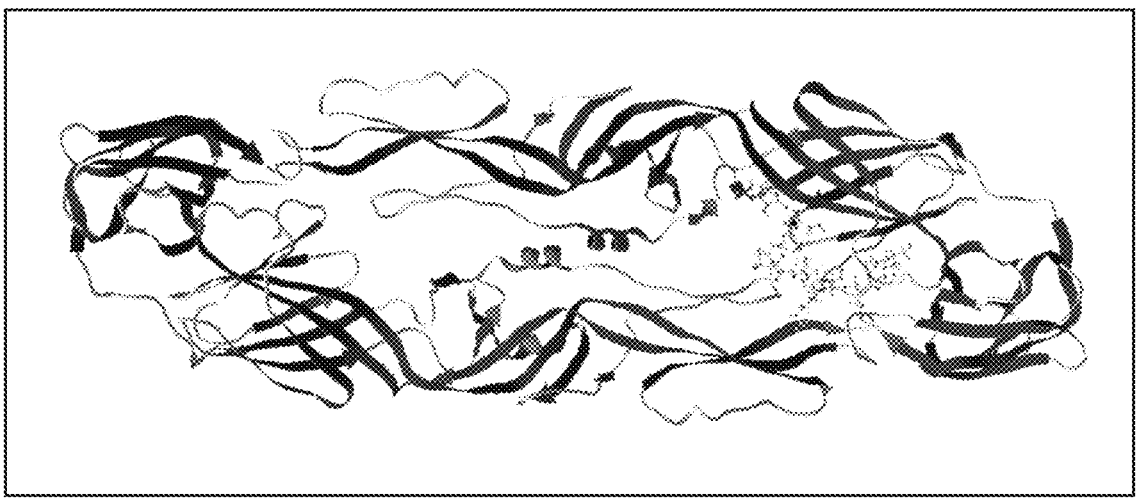
FIG. 25 is a 3-dimensional computer drawing using MVD software showing the most favored binding interaction of the model cationic polyamine B3 with the DENV-3 E protein.

FIG. 25 is a 3-dimensional computer drawing using MVD software showing the most favored binding interaction of the model cationic polyamine B3 with the DENV-3 E protein.

Figure 26:
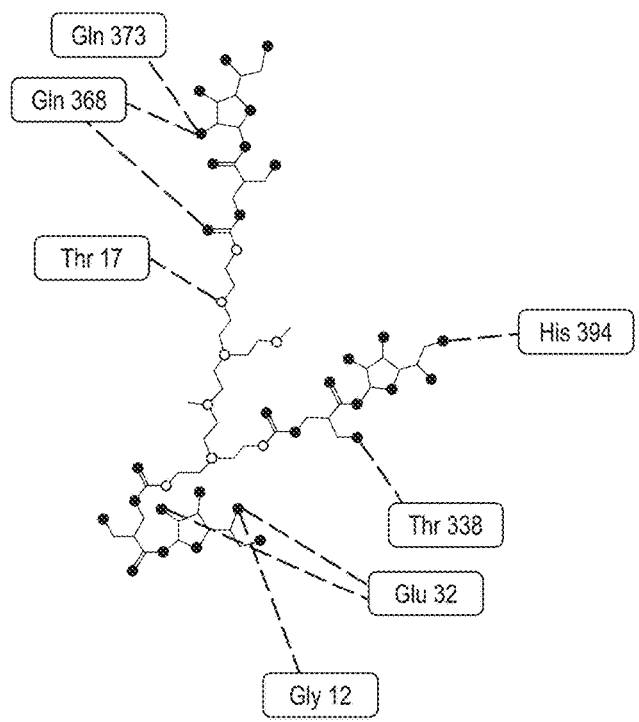
FIG. 26 is a computer drawing using MVD software showing the 7 amino acid residues of the CHIKV E1 protein that interact by hydrogen bonding with the model cationic polyamine B3: Gln 373, Gln 368, Thr 17, Gly 12, Glu 32, Thr 338, and His 394.

FIG. 26 is a computer drawing using MVD software showing the 7 amino acid residues of the CHIKV E1 protein that interact by hydrogen bonding with the model cationic polyamine B3: Gln 373, Gln 368, Thr 17, Gly 12, Glu 32, Thr 338, and His 394.

Figure 27:
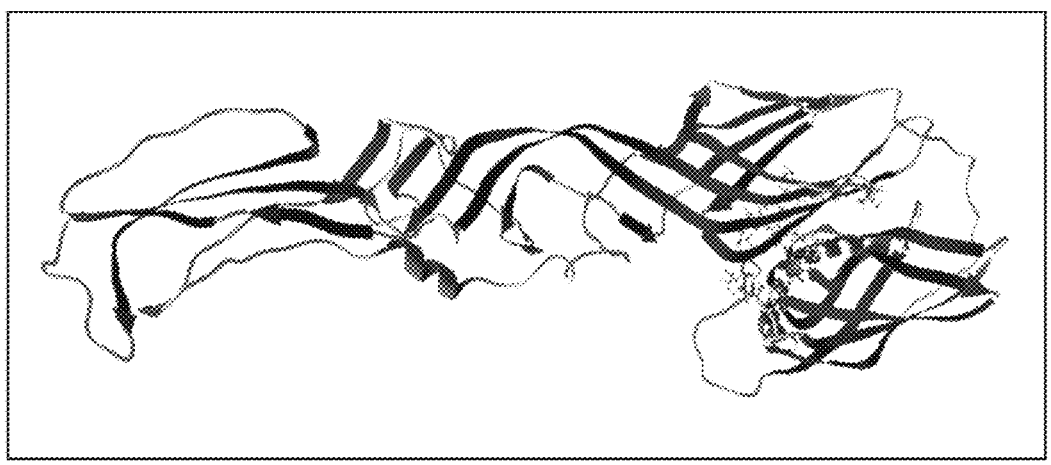
FIG. 27 is a 3-dimensional computer drawing using MVD software of the most favored binding interaction of the model cationic polyamine B3 with the CHIKV E1 protein.

FIG. 27 is a 3-dimensional computer drawing using MVD software of the most favored binding interaction of the model cationic polyamine B3 with the CHIKV E1 protein.

Figure 28:
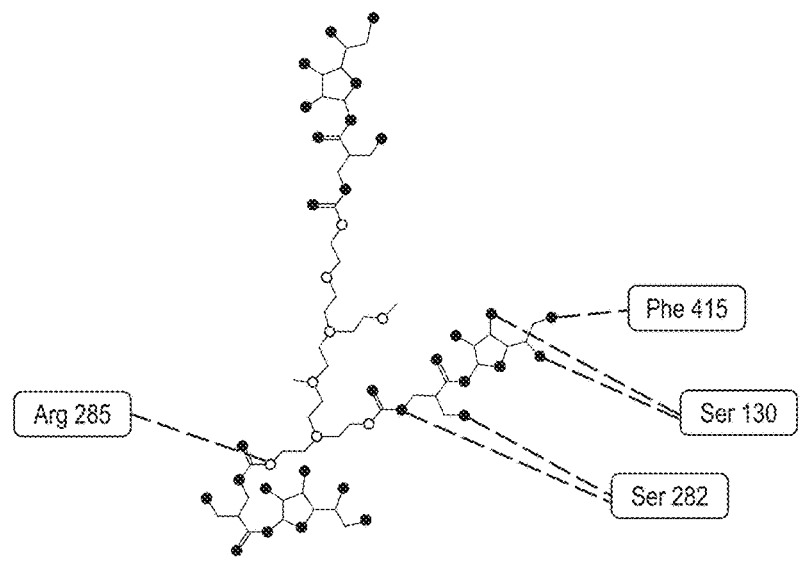
FIG. 28 is a computer drawing using MVD software showing the 4 amino acid residues of influenza virus HA protein that form hydrogen bonds with the model cationic polyamine B3: Arg 285, Ser 282, Ser 130, and Phe 415.

FIG. 28 is a computer drawing using MVD software showing the 4 amino acid residues of influenza virus HA protein that form hydrogen bonds with the model cationic polyamine B3: Arg 285, Ser 282, Ser 130, and Phe 415.

Figure 29:
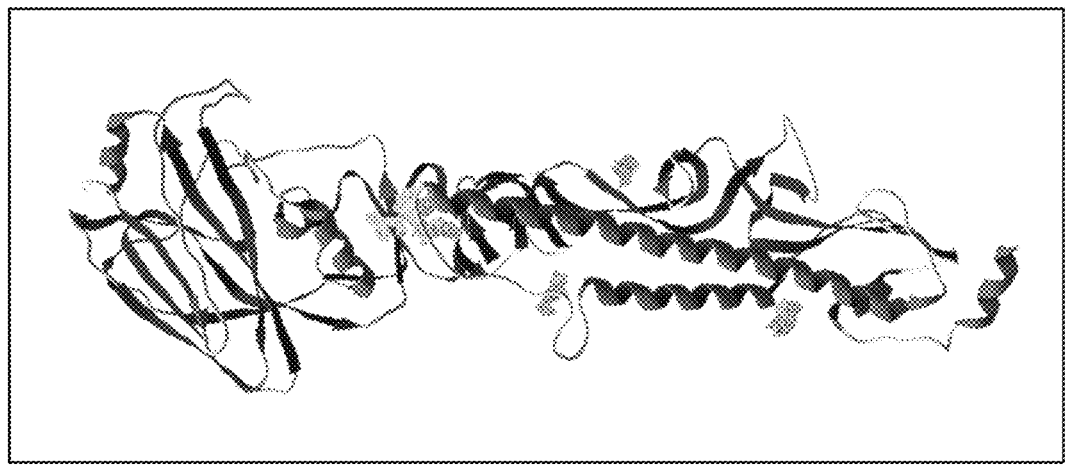
FIG. 29 is a 3-dimensional computer drawing using MVD software of the 4 cavities in the HA protein.

FIG. 29 is a 3-dimensional computer drawing using MVD software of the 4 cavities in the HA protein.

Figure 30:
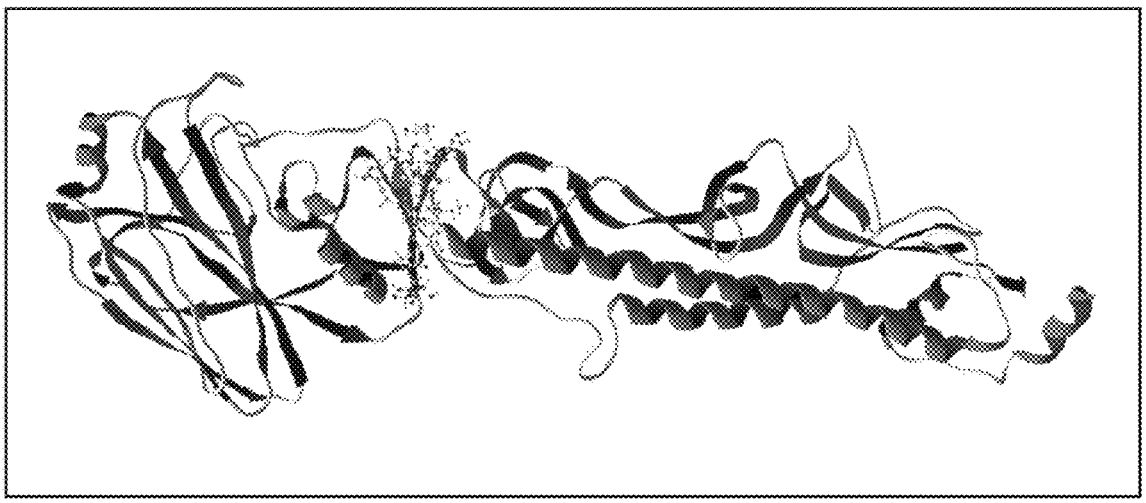
FIG. 30 is a 3-dimensional computer drawing using MVD software showing the most favored binding of the model cationic polyamine B3 to the HA protein.

FIG. 30 is a 3-dimensional computer drawing using MVD software showing the most favored binding of the model cationic polyamine B3 to the HA protein.

Figure 31:
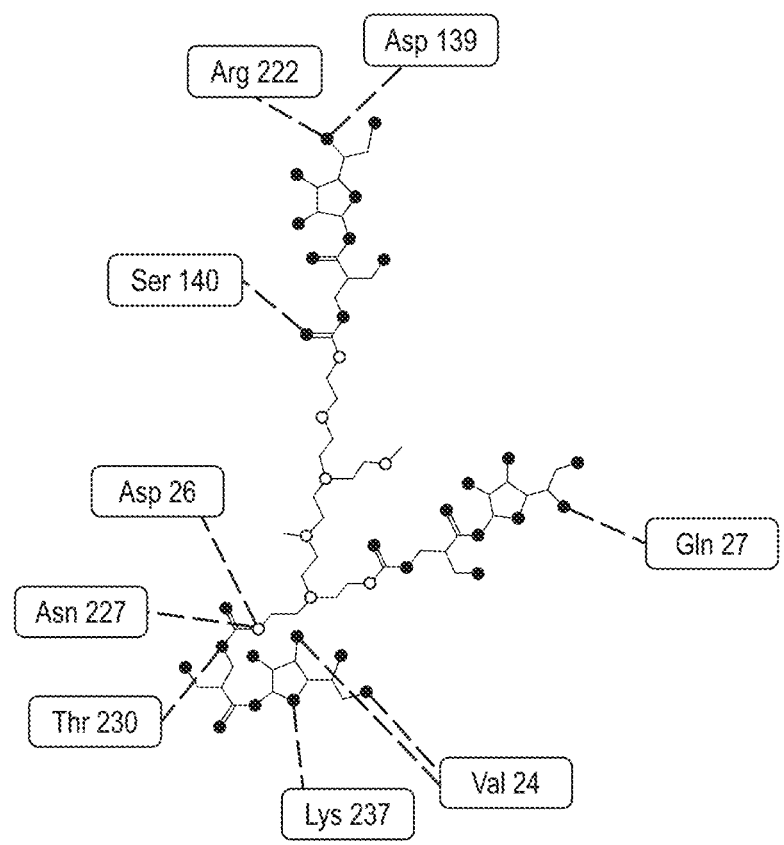
FIG. 31 is a computer drawing using MVD software showing the 9 amino acid residues of HSV-2 GD protein that form hydrogen bonds with the model cationic polyamine B3: Asp 139, Arg 222, Ser 140, Asp 26, Asn 227, Thr 230, Lys 237, Val 24, and Gln 27.

FIG. 31 is a computer drawing using MVD software showing the 9 amino acid residues of HSV-2 GD protein that form hydrogen bonds with the model cationic polyamine B3: Asp 139, Arg 222, Ser 140, Asp 26, Asn 227, Thr 230, Lys 237, Val 24, and Gln 27.

Figure 32:
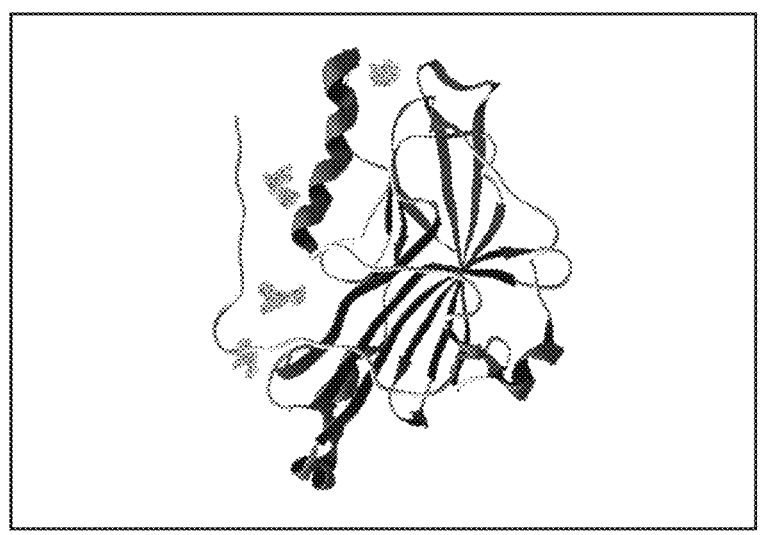
FIG. 32 is a 3-dimensional computer drawing using MVD software of 4 cavities in the GD protein.

FIG. 32 is a 3-dimensional computer drawing using MVD software of 4 cavities in the GD protein.

Figure 33:
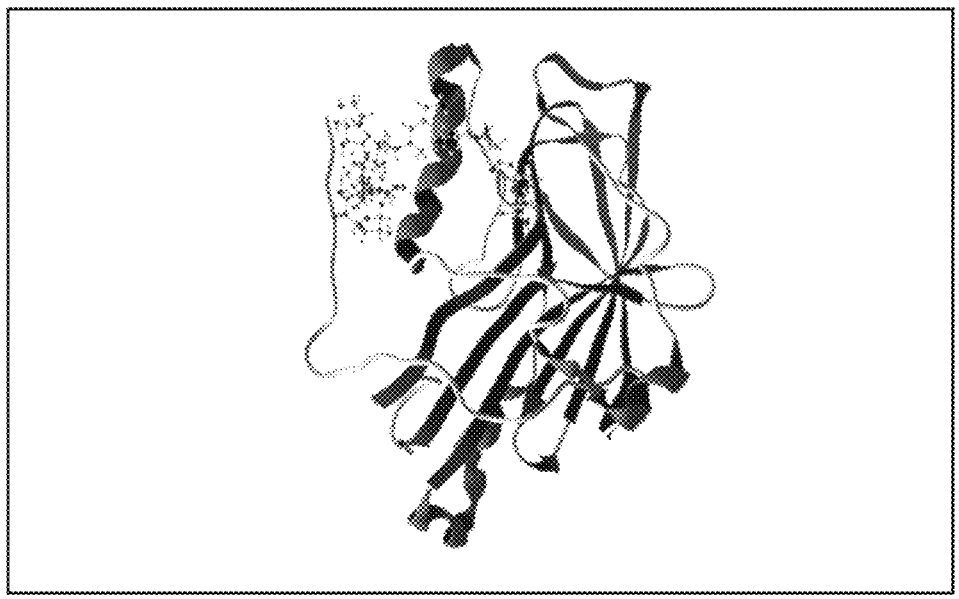
FIG. 33 is a 3-dimensional computer drawing using MVD software showing the most favored binding interaction of the model cationic polyamine B3 to the GD protein.

FIG. 33 is a 3-dimensional computer drawing using MVD software showing the most favored binding interaction of the model cationic polyamine B3 to the GD protein.

Figure 34:
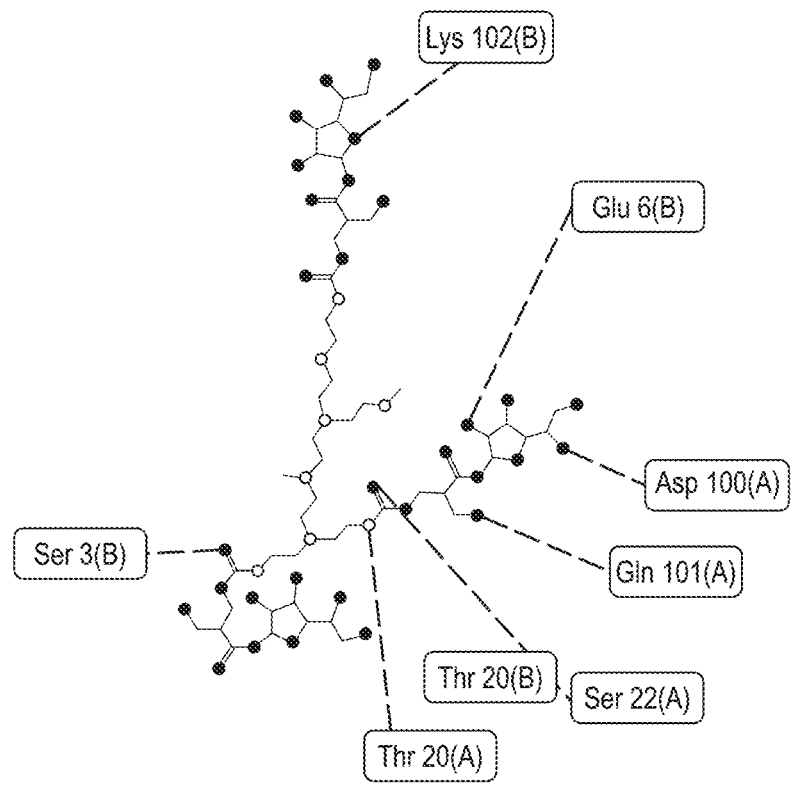
FIG. 34 is a computer drawing using MVD software showing the 8 amino acid residues of the TIM-1 protein that form hydrogen bonds with the model cationic polyamine B3: Lys 102(B), Ser 3(B), Thr 20(A), Thr 20(B), Ser 22(A), Gln 101 (A), Asp 100(A), and Glu 6(B).

FIG. 34 is a computer drawing using MVD software showing the 8 amino acid residues of the TIM-1 protein that form hydrogen bonds with the model cationic polyamine B3: Lys 102(B), Ser 3(B), Thr 20(A), Thr 20(B), Ser 22(A), Gln 101 (A), Asp 100(A), and Glu 6(B).

Figure 35:
FIG. 35 is a 3-dimensional computer drawing using MVD software showing the most favored binding interaction of the model cationic polyamine B3 to the TIM-1 protein.

FIG. 35 is a 3-dimensional computer drawing using MVD software showing the most favored binding interaction of the model cationic polyamine B3 to the TIM-1 protein.

Figure 36:
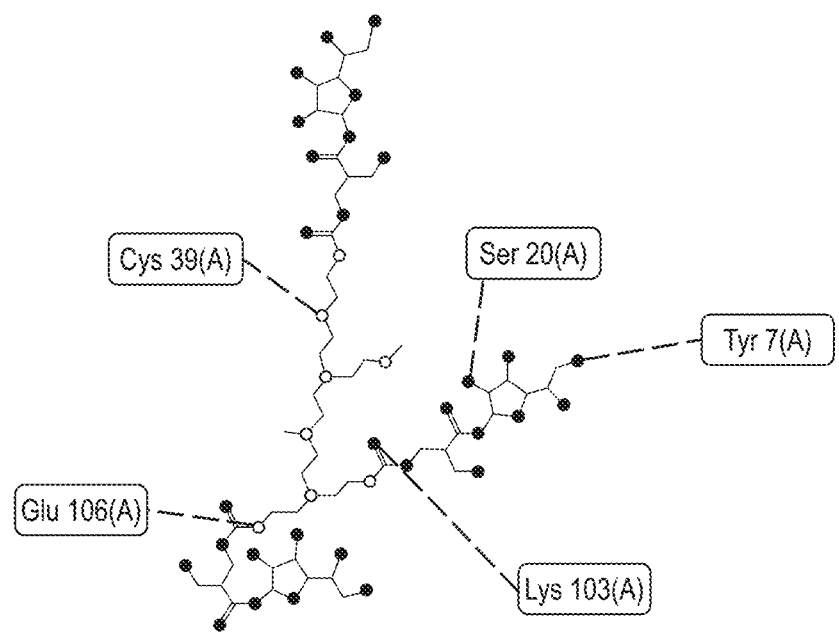
FIG. 36 is a computer drawing using MVD software showing the 5 amino acid residues of TIM-3 protein that form hydrogen bonds with the model cationic polyamine B3: Glu 106(A), Cys 39(A), Lys 103(A), Ser 20(A), and Tyr 7(A).

FIG. 36 is a computer drawing using MVD software showing the 5 amino acid residues of TIM-3 protein that form hydrogen bonds with the model cationic polyamine B3: Glu 106(A), Cys 39(A), Lys 103(A), Ser 20(A), and Tyr 7(A).

Figure 37:
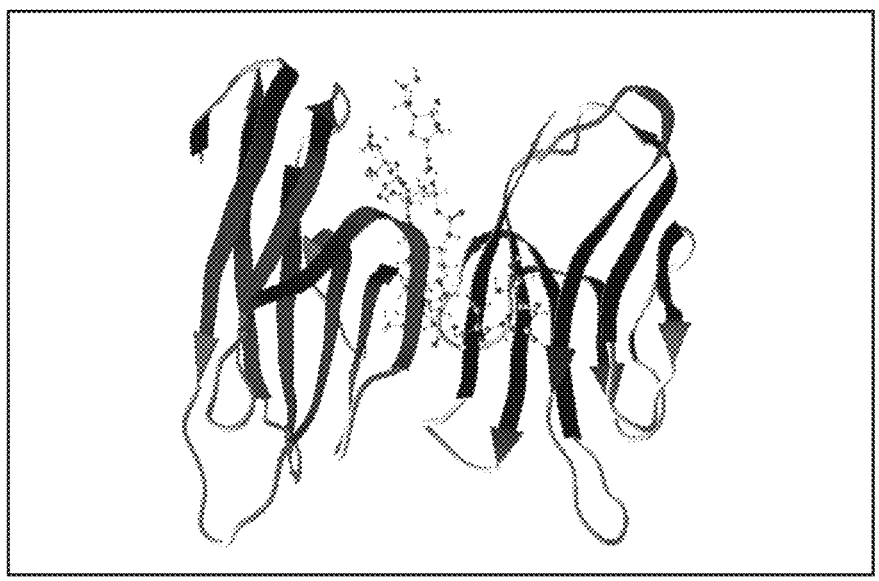
FIG. 37 is a 3-dimensional computer drawing using MVD software showing the most favored binding of the model cationic polyamine B3 to TIM-3.

FIG. 37 is a 3-dimensional computer drawing using MVD software showing the most favored binding of the model cationic polyamine B3 to TIM-3.

Figure 38:
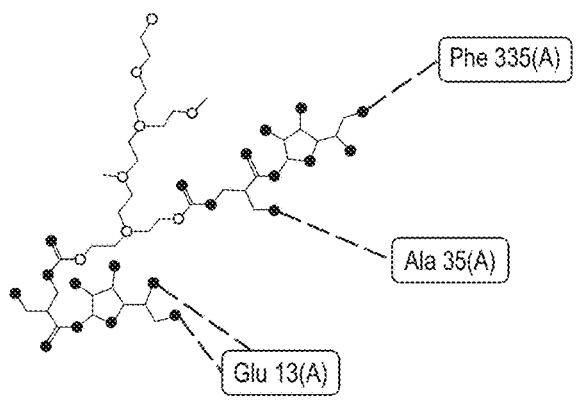
FIG. 38 is a computer drawing using MVD software showing the 3 amino acid residues of the DENV-3 E protein that form hydrogen bonds with the model cationic polyamine B3 structure: Glu 13(A), Ala 35(A), and Phe 335(A).

FIG. 38 is a computer drawing using MVD software showing the 3 amino acid residues of the DENV-3 E protein that form hydrogen bonds with the model cationic polyamine B3 structure: Glu 13(A), Ala 35(A), and Phe 335(A).

Figure 39:
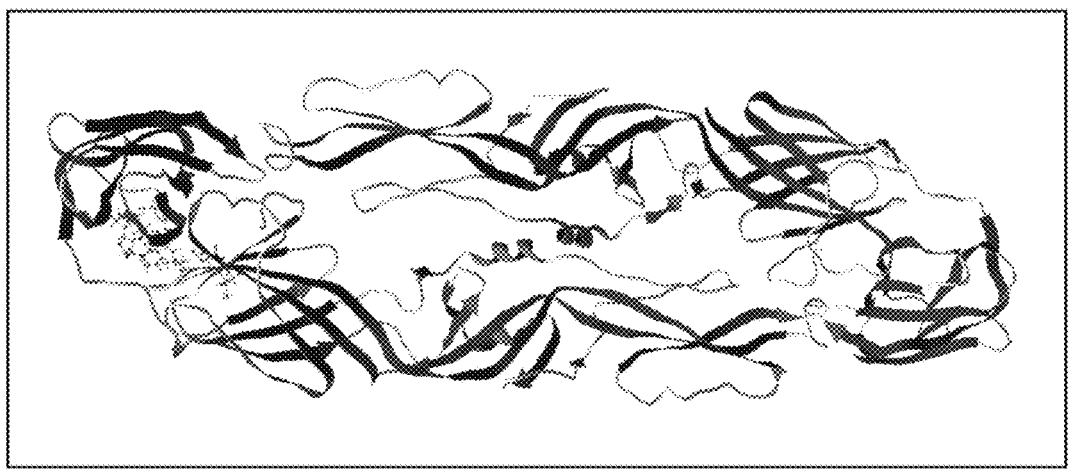
FIG. 39 is a 3-dimensional computer drawing using MVD software showing the most favored binding interaction of the model cationic polyamine B3 to the DENV-3 E protein.

FIG. 39 is a 3-dimensional computer drawing using MVD software showing the most favored binding interaction of the model cationic polyamine B3 to the DENV-3 E protein.

Figure 40:
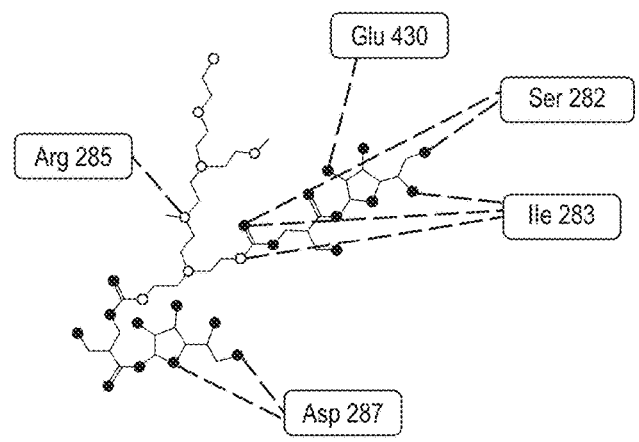
FIG. 40 is a computer drawing using MVD software showing the 5 amino acid residues of the Influenza HA protein that form hydrogen bonds with the model cationic polyamine B2: Arg 285, Glu 430, Ser 282, Ile 283, and Asp 287. The model B2 material had 2 mannose groups.

FIG. 40 is a computer drawing using MVD software showing the 5 amino acid residues of the Influenza HA protein that form hydrogen bonds with the model cationic polyamine B2: Arg 285, Glu 430, Ser 282, Ile 283, and Asp 287.

Figure 41:
FIG. 41 is a 3-dimensional computer drawing using MVD software showing the most favored binding of the model cationic polyamine B2 to the Influenza HA protein.

FIG. 41 is a 3-dimensional computer drawing using MVD software showing the most favored binding of the model cationic polyamine B2 to the Influenza HA protein.

In addition, docking results showed that the non-modified PEI-viral protein interaction was non-specific.

Table 7 summarizes the Moldock score, Rerank score, and calculated number of interacting amino acids forming hydrogen bonds with model cationic polyamine B3 with various viral proteins, obtained using the MVD software.

TABLE 7

| Virus | Type | Protein | Interaction | Moldock Score | Rerank Score | No. of interacting amino acids |
|---|---|---|---|---|---|---|
| DENV-2 | RNA | E | Specific | −192.45 | −95.43 | 8 |
| DENV-3 | RNA | E | Specific | −140.82 | −94.98 | 7 |
| CHIKV | RNA | E1 | Specific | −144.06 | −59.43 | 7 |
| EV 71 | RNA | VP1 | Specific | −146.60 | −60.07 | 7 |
| Influenza virus (A/H3N2) | RNA | HA | Specific | −97.30 | −31.09 | 4 |
| HSV-1 | DNA | GB | Specific | −56.88 | 104.77 | 7 |
| HSV-2 | DNA | GB | Specific | −95.34 | −26.45 | 9 |
|  |  | TIM-1 | Specific | −158.36 | −93.36 | 8 |
|  |  | TIM-3 | Specific | −117.11 | 18.62 | 5 |

Table 8 summarizes the Moldock score, Rerank score, and calculated number of interacting amino acids forming hydrogen bonds by model cationic polyamine B2 with DENV-3 E protein and Influenza HA protein using MVD software.

TABLE 8

| Virus | Type | Protein | Interaction | Moldock Score | Rerank Score | No. of interacting amino acids |
|---|---|---|---|---|---|---|
| DENV-3 | RNA | E | Specific | −152.30 | −97.81 | 3 |
| Influenza virus (A/H3N2) | RNA | HA | Specific | −148.77 | −75.59 | 5 |

CONCLUSION

Linear and branched PEI were modified in a rapid and facile nucleophilic addition reaction with a mannose-functionalized cyclic carbonate monomer. The resulting cationic polyamines display strong anti-viral activity, negligible toxicity and high selectivity towards virus particles over mammalian cells. The above data shows that anti-viral activity decreased (EC50 increased) with increasing mannose content of the modified BPEI25 (Table 5, B1-B6). Offsetting this trend in EC50 was a more rapidly decreasing cytotoxicity (increasing CC50) resulting in increasing selectivity (increasing CC50) with increasing mannose content (Table 5, B1-B6). The incorporation of mannose residues lowers PEI toxicity and allows targeting of the mannose receptor on the immune cells. The mannose-modified PEI specifically binds to viral surface proteins. The modified polymers have broad-spectrum anti-viral activity, effective against DNA, RNA, enveloped and non-enveloped viral infections, including DENY, HSV-1, HSV-2, CHIKV, SARS Co-V and EV 71. The cationic polyamines prevent viral infection by binding with viral and cell surfaces, inhibiting virus entry/membrane fusion and neutralizing the endosomal pH (mitigating membrane fusion). The cationic polyamines are also effective against viral infection of cells expressing TIM-1 or TIM-3. Importantly, by targeting both viral proteins and host-virus interactions, the antiviral polymers can mitigate drug resistance. Mannose-carbamate modified PEI has broad-spectrum anti-viral activity and no in vivo toxicity at its effective concentration, resulting in great potential for the prevention and treatment of a variety of viral infections.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method, comprising:

treating a virus with a cationic polyamine, the virus comprising DNA and/or RNA, the virus capable of causing a viral disease in mammals, thereby forming a treated virus comprising the cationic polyamine bound by non-covalent interactions to the virus; wherein:

i) the treated virus is less capable of entering a living mammalian cell and/or undergoing replication within a living mammalian cell compared to the virus before said treating, ii) the cationic polyamine comprises:

a plurality of non-charged N-acylated ethylenimine units of formula (1):

(1)

wherein each K' comprises at least one carbon and at least one alcohol hydroxyl group, and a plurality of positive-charged secondary ethylenimine units of formula (3a):

(3a)

wherein the starred bond of the nitrogen is linked to a carbon and $X^{\ominus}$ is a negative-charged counterion bound by non-covalent association with the positive charged nitrogen, and iii) the cationic polyamine comprises the N-acylated ethylenimine units and the secondary ethylenimine units arranged in a random distribution and linked covalently head-to-tail, wherein nitrogen 1 of a given ethylenimine unit is linked to carbon 3 of a different ethylenimine unit.

2. The method of claim 1, wherein each K' comprises a monovalent monosaccharide moiety.

3. The method of claim 2, wherein the monosaccharide moiety is selected from the group consisting of glucosyl groups, galactosyl groups, and mannosyl groups.

4. The method of claim 2, wherein the monosaccharide moiety is selected from the group consisting of 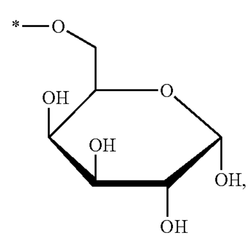 (alpha-D-Galactopyranosyl)

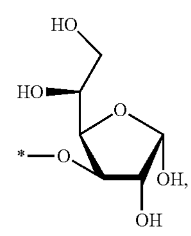

(alpha-D-Glucofuranosyl)

and (alpha-D-Mannofuranosyl)

5. The method of claim 1, wherein each K' comprises a catechol group.

6. The method of claim 1, wherein each *—C(=O)K' of the cationic polyamine is an independent monovalent radical selected from the group consisting of:

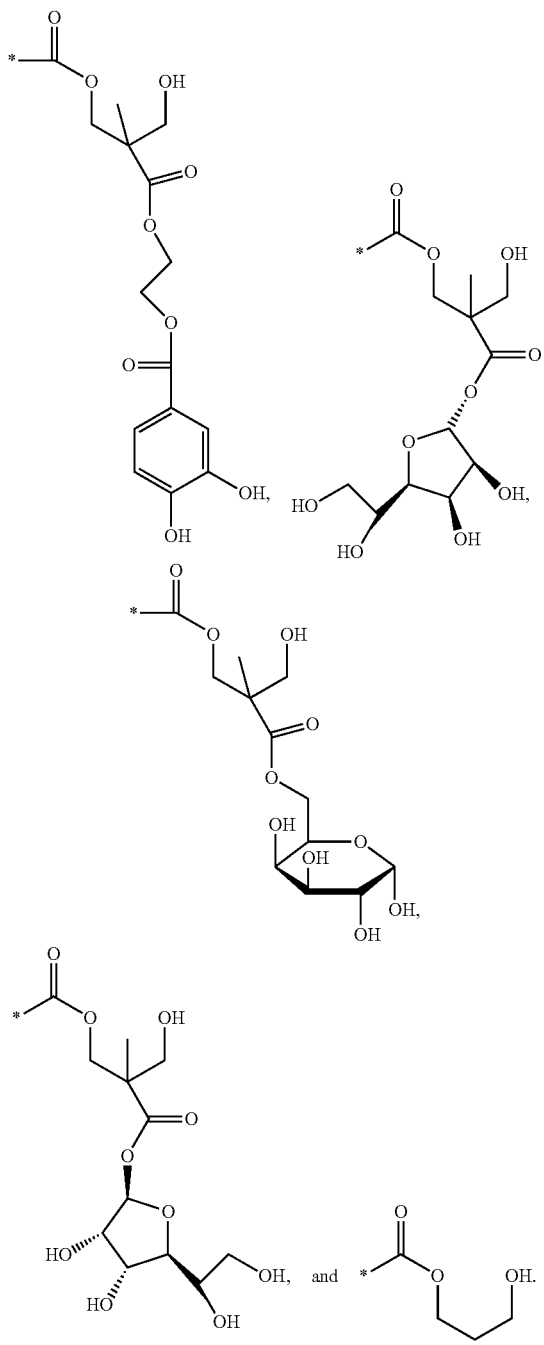

7. The method of claim 1, wherein the cationic polyamine has one polymer branch consisting essentially of the N-acylated ethylenimine units, the secondary ethylenimine units, and polymer chain end groups.

8. The method of claim 1, wherein the cationic polyamine further comprises an oxidized ethylenimine unit having the structure:

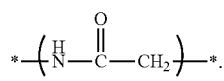

9. The method of claim 1, wherein the virus is a dengue virus.

10. The method of claim 1, wherein the cationic polyamine has a plurality of polymer branches comprising the N-acylated ethylenimine units, the secondary ethylenimine units, and tertiary ethylenimine unit having the structure

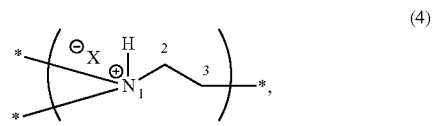

wherein $X^\ominus$ is a negative-charged counterion bound by non-covalent association with the positive charged nitrogen.

11. The method of claim 10, wherein the cationic polyamine is formed in a process comprising treating a branched polyethylenimine with an acylating agent comprising K' and/or a protected form of K'.

12. The method of claim 11, wherein the branched polyethylenimine has a number average molecular weight (Mn) greater than 1000.

13. A method, comprising:
treating a living mammalian cell with a cationic polyamine, the cell comprising a cell membrane, thereby forming a treated cell comprising the cationic polyamine bound by non-covalent interactions to the cell membrane; wherein:
i) the treated cell has more resistance to a virus entering the treated cell and/or replicating within the treated cell compared to the cell before said treating, the virus comprising DNA and/or RNA, the virus capable of causing a viral disease in mammals,
ii) the cationic polyamine comprises:
a plurality of non-charged N-acylated ethylenimine units of formula (1):

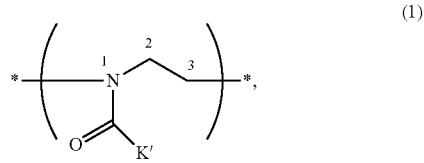

wherein each K' comprises at least one carbon and at least one alcohol hydroxyl group, and
a plurality of positive-charged secondary ethylenimine units of formula (3a):

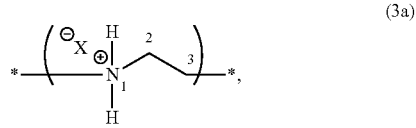

wherein the starred bond of the nitrogen is linked to a carbon, and $X^\ominus$ is a negative-charged counterion bound by non-covalent association with the positive charged nitrogen, and
iii) the cationic polyamine comprises the N-acylated ethylenimine units and the secondary ethylenimine units arranged in a random distribution and linked covalently head-to-tail, wherein nitrogen 1 of a given ethylenimine unit is linked to carbon 3 of a different ethylenimine unit.

14. The method of claim 13, wherein the virus is selected from the group consisting of dengue fever viruses, SARS corona viruses, Chikungunya viruses, enteroviruses, influenza viruses, herpes simplex viruses, and combinations thereof.

15. The method of claim 13, wherein the cationic polyamine inhibits entry of the virus into the mammalian cell by disrupting endosomal release of the virus.

16. The method of claim 13, wherein the mammalian cell is selected from the group consisting of blood cells, liver cells, nasal cells, lung cells, and cervical cells.

17. A method, comprising:
administering to a patient infected with a virus a therapeutically effective amount of a cationic polyamine, thereby inhibiting and/or preventing replication of the virus, the virus comprising DNA and/or RNA, the virus capable of causing a viral disease in mammals, the cationic polyamine bound by non-covalent interactions to the virus;
wherein:
i) the cationic polyamine comprises:
a plurality of non-charged N-acylated ethylenimine units of formula (1):

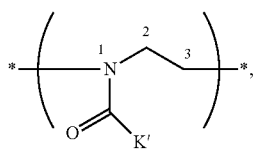  (1)

wherein each K' comprises at least one carbon and at least one alcohol hydroxyl group, and
a plurality of positive-charged secondary ethylenimine units of formula (3a):

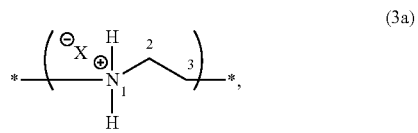  (3a)

wherein the starred bond of the nitrogen is linked to a carbon, and $X^{\ominus}$ is a negative-charged counterion bound by non-covalent association with the positive charged nitrogen, and
ii) the cationic polyamine comprises the N-acylated ethylenimine units and the secondary ethylenimine units arranged in a random distribution and linked covalently head-to-tail, wherein nitrogen 1 of a given ethylenimine unit is linked to carbon 3 of a different ethylenimine unit.

18. The method of claim 17, wherein the cationic polyamine is administered as an aqueous mixture.

19. The method of claim 18, wherein the aqueous mixture is administered by injection.

20. The method of claim 17, wherein the cationic polyamine binds non-covalently to the virus, thereby impeding entry of the virus into cells of the patient.

21. The method of claim 17, wherein the cationic polyamine binds non-covalently to cells of the patient, thereby impeding entry of the virus into the cells of the patient.

22. The method of claim 17, wherein the cationic polyamine is non-cytotoxic at the therapeutically effective dose.

* * * * *